(12) United States Patent
Matsuda et al.

(10) Patent No.: US 9,103,790 B2
(45) Date of Patent: Aug. 11, 2015

(54) LINKER FOR UNIMOLECULAR FRET BIOSENSOR BASED ON PRINCIPLE OF FLUORESCENCE RESONANCE ENERGY TRANSFER

(71) Applicant: KYOTO UNIVERSITY, Kyoto (JP)

(72) Inventors: Michiyuki Matsuda, Kyoto (JP); Naoki Komatsu, Kyoto (JP); Kazuhiro Aoki, Kyoto (JP); Yuji Kamioka, Kyoto (JP); Hiroko Yukinaga, Kyoto (JP); Yoshie Inaoka, Kyoto (JP); Atsuro Sakurai, Kyoto (JP); Etsuko Kiyokawa, Kyoto (JP); Kenta Sumiyama, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 13/837,535

(22) Filed: Mar. 15, 2013

(65) Prior Publication Data

US 2013/0227718 A1    Aug. 29, 2013

Related U.S. Application Data

(63) Continuation of application No. PCT/JP2011/071891, filed on Sep. 26, 2011.

(30) Foreign Application Priority Data

Sep. 27, 2010  (JP) .................. 2010-215738

(51) Int. Cl.
| | |
|---|---|
| *G01N 21/64* | (2006.01) |
| *A61K 8/64* | (2006.01) |
| *A61K 51/08* | (2006.01) |
| *G01N 33/52* | (2006.01) |
| *C12Q 1/48* | (2006.01) |
| *C07K 14/00* | (2006.01) |
| *C07K 14/435* | (2006.01) |
| *A01K 67/027* | (2006.01) |
| *G01N 33/542* | (2006.01) |

(52) U.S. Cl.
CPC ........ *G01N 21/6486* (2013.01); *A01K 67/0275* (2013.01); *C07K 14/00* (2013.01); *C07K 14/43595* (2013.01); *C12Q 1/485* (2013.01); *A01K 2217/052* (2013.01); *A01K 2227/105* (2013.01); *A01K 2267/0393* (2013.01); *G01N 33/542* (2013.01); *G01N 2333/4719* (2013.01); *G01N 2500/04* (2013.01)

(58) Field of Classification Search
None
See application file for complete search history.

(56) References Cited

U.S. PATENT DOCUMENTS

2006/0265764 A1 * 11/2006  Umezawa et al. ............. 800/8
2007/0275428 A1 * 11/2007  Gambhir et al. ............ 435/8

FOREIGN PATENT DOCUMENTS

| GB | 2375538 A | 11/2002 |
|---|---|---|
| JP | 2004/187544 A | 7/2004 |
| WO | 02/14373 A1 | 2/2002 |
| WO | 2009/151948 A2 | 12/2009 |
| WO | 2009/151948 A3 | 12/2009 |

OTHER PUBLICATIONS

Frommer et al., Genetically encoded biosensors based on engineered fluorescent protein. Chem. Soc. Rev., 2009, 38, 2833-2841.*
Wriggers et al., Control of Protein Functional Dynamics by Peptide Linkers. Biopolymers (Peptide Science), vol. 80, 736-746 (2005).*
Shaner et al., Advances in fluorescent protein technology. Dec. 15, 2007 J Cell Sci 120, 4247-4260.*
Aoki, K. and M. Matsuda: Visualization of small GTPase activity with fluorescence resonance energy transfer-based biosensors, Nature Protocol, 2009, 4:1623-1631.
Giepmans, B. N., S. R. Adams, M. H. Ellisman, and R. Y. Tsien: The fluorescent Toolbox for Assessing Protein Location and Function, Science, Apr. 14, 2006, 312:217-224.
Jares-Erijman, E. A., and T. M. Jovin: Imaging molecular interactions in living cells by FRET microscopy, Curr. Opin. Chem. Biol., 2006, 10:409-416.
Kiyokawa, E., S. Hara, T. Nakamura, and M. Matsuda: Fluorescence (Forster) resonance energy transfer imaging of oncogene activity in living cells, Cancer Sci. Jan. 2006, 97:8-15.
Itoh, R. E., K. Kurokawa, Y. Ohba, H. Yoshizaki, N. Mochizuki, and M. Matsuda: Activation of Rac and Cdc42 video-imaged by FRET-based single-molecule probes in the membrane of living cells, Mol. Cell. Biol., 2002, 22:6582-6591.
Harvey, C. D., A. G. Erhardt, C. Cellurale, H. Zhong, R. Yasuda, R. J. Davis, and K. Svoboda: A genetically encoded fluorescent sensor of ERK activity, Proc. Natl. Acad. Sci. U. S. A., Dec. 9, 2008, 105:19264-19269.
Naoki Komatsu et al.: "Development of FRET-based probes monitoring protein phosphorylation in a living cell", Journal of Japanese Biochemical Society, 25 Acad. Sci. U.S.A., Sep. 25, 2009, 105:19264-19269.
Etsuko Kiyokawa et al.: "FRET live imaging of cancer", Surgery Frontier, Mar. 1, 2011, vol. 18(1), pp. 9-18.
International Search Report, dated Nov. 15, 2011, for corresponding International Patent Application No. PCT/JP2011/071891.
Database UniProt [Online], "SubName: Full =Uncharacterized protein;", XP002719531, retrieved from EBI accession No. UniProt:D3BJC0 Database accession No. D3BJC0, Mar. 23, 2010.

(Continued)

*Primary Examiner* — Scott Long
*Assistant Examiner* — Arthur S Leonard
(74) *Attorney, Agent, or Firm* — Pergament Gilman & Cepeda LLP; Milagros A. Cepeda; Edward D. Pergament

(57) ABSTRACT

A linker for a unimolecular FRET biosensor based on a principle of fluorescence resonance energy transfer, the linker including: a polypeptide containing 52 to 400 amino acids residues, wherein at least 45% of a total number of the amino acid residues are glycine, alanine, or both thereof, and at least 10% of the total number of the amino acid residues are alanine.

3 Claims, 21 Drawing Sheets
(1 of 21 Drawing Sheet(s) Filed in Color)

(56) References Cited

OTHER PUBLICATIONS

Database UniProt [Online], "SubNanne: Full =Merozoite surface protein 2; Flags: Fragment;", XP002719532, retrieved from EBI accession No. UniProt:Q9BJP8 Database accession No. Q9BJP8, Jun. 1, 2001.

Atsushi Miyawaki, "Visualization of the Spatial and Temporal Dynamics of Intracellular Signaling", Review, Developmental Press, Mar. 2003, pp. 295-305, vol. 4, Cell Press.

N. Komatsu et al., "Development of an optimized backbone of FRET biosensors for kinases and GTPases", Article, Molecular Biology of the Cell, Dec. 1, 2011, pp. 4647-4656, vol. 22.

N. Komatsu et al., "Development of an optimized backbone of FRET biosensors for kinases and GTPases", Supplemental Information, Molecular Biology of the Cell, Dec. 1, 2011.

Extended European Search Report dated Feb. 18, 2014, for corresponding European Patent Application No. EP 11 82 9031.

* cited by examiner

LINKER FOR UNIMOLECULAR FRET BIOSENSOR BASED ON PRINCIPLE OF FLUORESCENCE RESONANCE ENERGY TRANSFER

CROSS-REFERENCE TO RELATED APPLICATION

This is a continuation application of PCT/JP2011/071891, filed on Sep. 26, 2011, which claims priority to Japanese Patent Application No. 2010-215738, filed on Sep. 27, 2010, all of which are hereby incorporated by reference in their entirety.

BACKGROUND OF THE INVENTION

1. Field of the Invention

The present invention relates to a linker for optimizing a unimolecular FRET biosensor based on the principle of fluorescence resonance energy transfer; a biosensor containing the linker; a gene encoding for the linker or the unimolecular FRET biosensor; an expression vector containing the linker or the unimolecular FRET biosensor; a transformed cell and a transgenic non-human animal harboring the expression vector; and a measurement method using the biosensor.

2. Description of the Related Art

Biosensors utilizing the principle of fluorescence resonance energy transfer (hereinafter may be referred to as "FRET") and fluorescent proteins have been increasingly used in the field of life science (see Aoki, K. and M. Matsuda. 2009. Visualization of small GTPase activity with fluorescence resonance energy transfer-based biosensors. Nature Protocol 4:1623-1631, Giepmans, B. N., S. R. Adams, M. H. Ellisman, and R. Y. Tsien. 2006. The fluorescent toolbox for assessing protein location and function. Science 312:217-224, Jares-Erijman, E. A. and T. M. Jovin. Imaging molecular interactions in living cells by FRET microscopy. 2006. Curr. Opin. Chem. Biol. 10:409-416, and Kiyokawa, E., S. Hara, T. Nakamura, and M. Matsuda. 2006. Fluorescence (Forster) resonance energy transfer imaging of oncogene activity in living cells. Cancer Sci. 97:8-15).

The FRET is a phenomenon of excitation energy transfer from an excited fluorescent molecule (donor: energy donor) to a fluorescent molecules in the close vicinity of the donor (acceptor: energy acceptor). A development and improvement of Green fluorescent protein (GFP) mutants of different colors have greatly contributed to the spread of the biosensors utilizing the FRET. Nowadays, CFP (cyan fluorescent protein) and YFP (yellow fluorescent protein), which both are GFP mutants, have often been used as donor and acceptor fluorescent proteins.

FRET biosensor systems utilizing the fluorescent proteins are classified into two types: bimolecular FRET biosensors (see FIG. 1) and unimolecular FRET biosensors (see FIG. 2). The bimolecular FRET biosensors detect intermolecular interactions, whereas the unimolecular FRET biosensors detect conformational changes in molecules (see Aoki, K. and M. Matsuda. 2009. Visualization of small GTPase activity with fluorescence resonance energy transfer-based biosensors. Nature Protocol 4:1623-1631, Giepmans, B. N., S. R. Adams, M. H. Ellisman, and R. Y. Tsien. 2006. The fluorescent toolbox for assessing protein location and function. Science 312:217-224, Jares-Erijman, E. A. and T. M. Jovin. Imaging molecular interactions in living cells by FRET microscopy. 2006. Curr. Opin. Chem. Biol. 10:409-416, and Kiyokawa, E., S. Hara, T. Nakamura, and M. Matsuda. 2006. Fluorescence (Forster) resonance energy transfer imaging of oncogene activity in living cells. Cancer Sci. 97:8-15).

Among them, there have been developed the unimolecular biosensors (unimolecular FRET biosensors) for quantifying small molecules such as ions, saccharides and lipids or for measuring activities of low molecular weight GTP-binding proteins or kinases (see Kiyokawa, E., S. Hara, T. Nakamura, and M. Matsuda. 2006. Fluorescence (Forster) resonance energy transfer imaging of oncogene activity in living cells. Cancer Sci. 97:8-15).

However, in order to create the biosensors, at least 3, often 4 or more protein domains are required to be connected. Unimolecular FRET biosensors having a satisfactory sensitivity usually cannot be achieved simply by connecting the protein domains to each other. That is, in order to create such unimolecular FRET biosensors, the following three factors should be taken into account: (i) an overlap of emission spectra of donor fluorescent proteins and absorption spectra of acceptor fluorescent proteins, (ii) a distance between the donor fluorescent proteins and the acceptor fluorescent proteins, and (iii) an orientation of emission moments of the donor fluorescent proteins and the absorption moments of acceptor fluorescent proteins. The fluorescent proteins may be fused with other proteins, which may apply stress to the fluorescent proteins to thereby cause misfoldings in the fluorescent proteins. As a result, the fluorescent proteins may form fluorophores inefficiently to thereby be nonfluorescent, which also should be taken into account. As described above, the FRET between the donor fluorescent proteins and the acceptor fluorescent proteins can be excellently achieved only when strict conditions are met. However, no requirement regarding, for example, an arrangement of the donor fluorescent proteins and the acceptor fluorescent proteins has been established. Therefore, for each unimolecular FRET biosensor to be created, optimizations have been performed by varying lengths of the protein domains or sequences of linkers connecting the domains, which needs a lot of trial and error and complex and advanced experiments. Accordingly, unimolecular FRET biosensors having a satisfactory sensitivity have been very hard to be developed.

Some linkers for connecting the domains have been reported such as a 9-amino acid linker consisting of glycine, serine and threonine (see Itoh, R. E., K. Kurokawa, Y. Ohba, H. Yoshizaki, N. Mochizuki, and M. Matsuda. 2002. Activation of Rac and Cdc42 video-imaged by FRET-based single-molecule probes in the membrane of living cells. Mol. Cell. Biol. 22:6582-6591) and a 72-amino acid glycine linker (see Harvey, C. D., A. G. Ehrhardt, C. Cellurale, H. Zhong, R. Yasuda, R. J. Davis, and K. Svoboda. 2008. A genetically encoded fluorescent sensor of ERK activity. Proc. Natl. Acad. Sci. U.S.A. 105:19264-19269), which linkers have not been sufficiently optimized. Additionally, the above-described linkers could not be optimized in common with many types of unimolecular FRET biosensors.

SUMMARY OF THE INVENTION

The present invention aims to solve the above existing problems and achieve the following objects. That is, the present invention aims to provide a linker which is capable of being widely used for optimizing a unimolecular FRET biosensor based on the principle of fluorescence resonance energy transfer to thereby achieve a high-sensitive unimolecular FRET biosensor (hereinafter, the linker of the present invention may be referred to as "EV (enhanced visualization) linker"); a biosensor containing the linker; a gene encoding for the linker or the biosensor; an expression vector containing the linker or the biosensor; a transformed cell and a transgenic non-human animal harboring the expression vector; and a measurement method using the unimolecular FRET biosensor suitable for measuring a serine-threonine kinase activity, a tyrosine kinase activity and a low molecular weight GTP-binding protein activity by means of the biosensor containing the linker.

The present inventors conducted extensive studies to achieve the above objects, and have found that a linker having a certain length or longer can solve the above objects and be a linker which is capable of being widely used for optimizing a unimolecular FRET biosensor based on the principle of fluorescence resonance energy transfer to thereby achieve a high-sensitive unimolecular FRET biosensor. Additionally, the present inventors have also been found that a linker containing certain amino acids at a certain percentage or certain repeated amino acid sequences has an improved optimization effect.

That is, the present invention is based on a finding that a linker having a certain length or longer can significantly reduce a FRET at a basal state which is a cause of a decrease in a gain of a unimolecular FRET biosensor. The present invention can be widely used for creating unimolecular FRET biosensors. The linker of the present invention has been developed for the purpose of increasing a gain of a unimolecular FRET biosensor, which is very technically valuable.

Means for solving the above problems are as follows.

The present invention provides a linker for a unimolecular FRET biosensor based on a principle of fluorescence resonance energy transfer, the linker including: a polypeptide containing 52 to 400 amino acids residues, wherein at least 45% of a total number of the amino acid residues are glycine, alanine, or both thereof, and at least 10% of the total number of the amino acid residues are alanine.

In an object the present invention provides a linker according to the present invention wherein the polypeptide contains 84 or more amino acid residues.

In an object the present invention provides a linker according to the present invention wherein at least 10% of the total number of the amino acid residues are serine, threonine, or both thereof.

In an object the present invention provides a linker according to the present invention wherein at least 95% of the total number of the amino acid residues are glycine, serine, threonine and alanine, 35% to 65% of the total number of the amino acid residues are glycine, 10% to 40% of the total number of the amino acid residues are serine, threonine, or both thereof, and 10% to 40% of the total number of the amino acid residues are alanine.

In an object the present invention provides a linker according to the present invention wherein at least 95% of the total number of the amino acid residues are repeats of an amino acid sequence of SAGG or GGAS, and wherein the number of the repeats of the amino acid sequence of SAGG or GGAS is 13 to 100.

In an object the present invention provides a linker according to the present invention wherein at least 10% of the total number of the amino acid residues are arginine, glutamic acid, or both thereof.

In an object the present invention provides a linker according to the present invention wherein at least 95% of the total number of the amino acid residues are glycine, arginine, glutamic acid and alanine, 4% to 30% of the total number of the amino acid residues are glycine, 5% to 30% of the total number of the amino acid residues are arginine, 5% to 30% of the total number of the amino acid residues are glutamic acid, and 30% to 60% of the total number of the amino acid residues are alanine.

The present invention provides a gene, wherein the gene encodes the linker according to the present invention.

The present invention provides an expression vector, including a gene encoding the linker according to the present invention.

The present invention provides a transformed cell, including an expression vector according to the present invention.

The present invention provides a transgenic non-human animal, including an expression vector according to the present invention.

The present invention provides a unimolecular FRET biosensor based on a principle of fluorescence resonance energy transfer, the unimolecular FRET biosensor including: a fused protein, which includes a sensor domain, a ligand domain, an acceptor fluorescent protein domain, a donor fluorescent protein domain, and a linker domain which links the sensor domain with the ligand domain, wherein the linker domain includes the linker of the present invention.

An object of the present invention provides an unimolecular FRET biosensor according to the present invention, wherein the donor fluorescent protein is YPet.

An object of the present invention provides a gene, wherein the gene encodes the unimolecular FRET biosensor according to the present invention.

An object of the present invention provides an expression vector, including a gene according to the present invention.

An object of the present invention provides a transformed cell, including the expression vector according to the present invention.

An object of the present invention provides a transgenic non-human animal, including the expression vector according to the present invention.

The present invention provides a method for measuring a serine-threonine kinase activity, a tyrosine kinase activity, or a low molecular weight GTP-binding protein activity, the method including: detecting FRET with the unimolecular FRET biosensor according to the present invention.

The present invention provides a method for measuring a serine-threonine kinase activity, a tyrosine kinase activity, or a low molecular weight GTP-binding protein activity, the method including: detecting FRET with the transformed cell according to the present invention or the transgenic non-human animal according to the present invention.

The present invention provides a method for screening a regulator of a serine-threonine kinase activity, a tyrosine kinase activity, or a low molecular weight GTP-binding protein activity, the method including: (a) contacting a test substance with the transformed cell according to the present invention; and (b) detecting FRET to thereby detect a change in the serine-threonine kinase activity, the tyrosine kinase activity, or the low molecular weight GTP-binding protein activity.

The linker of the present invention can optimize a unimolecular FRET biosensor based on the principle of fluorescence resonance energy transfer to thereby achieve a high-sensitive unimolecular FRET biosensor. In addition, the unimolecular FRET biosensor of the present invention enables non-invasive measurements of a serine-threonine kinase activity, a tyrosine kinase activity and a low molecular weight GTP-binding protein activity

BRIEF DESCRIPTION OF THE DRAWINGS

The patent or application file contains at least one drawing executed in color. Copies of this patent application publication with color drawing(s) will be provided by the Office upon request and payment of the necessary fee.

FIG. 7A illustrates measurement results of fluorescence intensities at various wavelengths when Eevee-PKA-52-expressing HeLa cells were observed by a confocal laser scanning microscope FV1000 upon excitation at 438 nm.

FIG. 11A illustrates a graph in which FRET/CFP fluorescence ratios (measured values) are plotted on Y-axis when Eevee-ERK (3560 NES) containing the EV116 linker was expressed in HeLa cells and stimulated with 10 ng/mL EGF.

FIG. 18A illustrates results of DMSO controls.

DETAILED DESCRIPTION OF THE INVENTION

There will be explained embodiments of the present invention.

A linker of the present invention (referred to as "EV linker") is a linker for a unimolecular FRET biosensor based on the principle of fluorescence resonance energy transfer (FRET). The linker is a polypeptide containing 52 to 400 amino acids residues in which at least 45% of the total number of amino acid residues are glycine and/or alanine and which contains alanine in a percentage of at least 10% of the total number of amino acid residues.

The linker of the present invention is an element of the unimolecular FRET biosensor based on the principle of fluorescence resonance energy transfer (FRET), i.e., the unimolecular FRET biosensor, and is used by connecting with other elements. The FRET is a phenomenon of excitation energy transfer from an excited fluorescent molecule (donor: energy donor) to a fluorescent molecules in the close vicinity of the donor (acceptor: energy acceptor). The unimolecular FRET biosensor generally contains the following four domains: a donor fluorescent protein, an acceptor fluorescent protein, a sensor domain, and a ligand domain. The linker connects two domains of the above domains.

Figure 1:
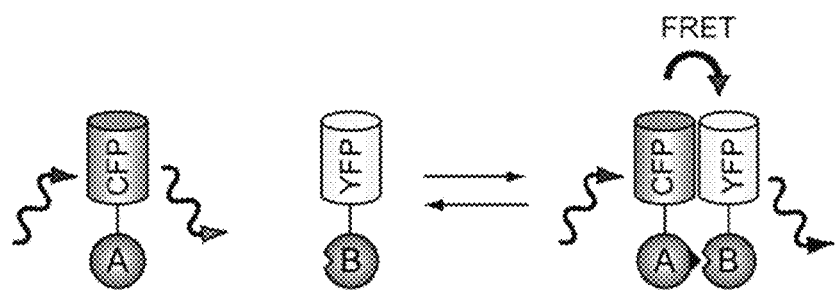
FIG. 1 illustrates a basic structure and a mode of action of a bimolecular FRET biosensor. In order to detect an intermolecular interaction escent protein (in this figure, CFP), and the B has been fused with a FRET between molecules A and B, the A has been fused with a ceptor fluorescent protein. As a result, FRET occurs and fluorescence can beFRET donor fluor acceptor fluorescent protein (in this figure, YFP). When the A binds to the B, the FRET donor fluorescent protein approaches the FRET ac detected from the FRET acceptor fluorescent protein. In this figure, wavy arrows denote excitation light and fluorescence, respectively.
Figure 2:
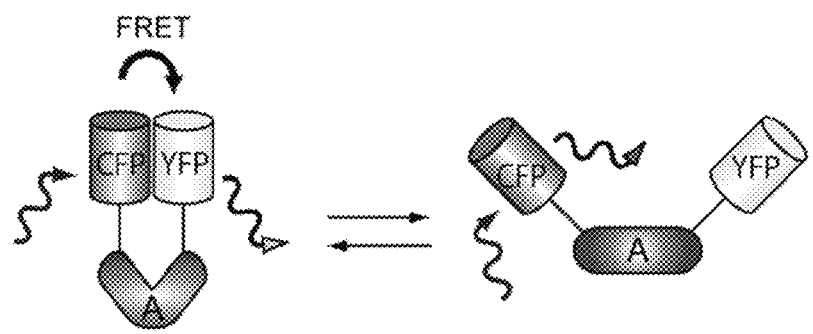
FIG. 2 illustrates a basic structure and a mode of action of a unimolecular FRET biosensor. When a molecule A is known to be conformationally changed, a FRET donor fluorescent protein (in this figure, CFP) and a FRET acceptor fluorescent protein (in this figure, YFP) are fused with the A at different sites. A conformational change of the molecule A changes FRET efficiency. In this figure, wavy arrows denote excitation light and fluorescence, respectively
Figure 3:
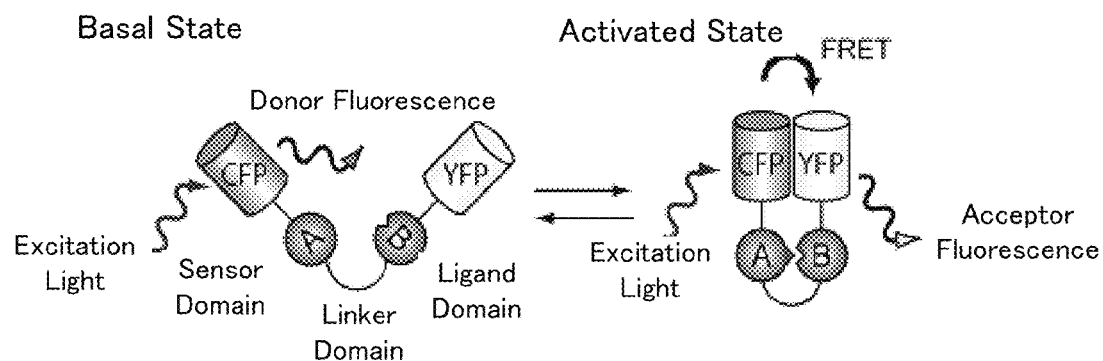
FIG. 3 illustrates a principle of a unimolecular FRET biosensor containing a sensor domain and a ligand domain based on FRET. Between a FRET donor fluorescent protein (in this figure, CFP) and a FRET acceptor fluorescent protein (in this figure, YFP), the sensor domain and the ligand domain are connected via a linker sequence. The sensor domain contains a region of which conformation changes in response to various intracellular environmental changes such as activations of a kinase or a GTP exchange factor. The ligand domain is a domain to be bound to the sensor domain in response to the conformational change of the sensor domain. When the sensor domain conformationally changes, the ligand domain binds to the sensor domain. Thus, the FRET donor fluorescent protein approaches the FRET acceptor fluorescent protein. As a result, the FRET occurs and fluorescence can be detected from the FRET acceptor fluorescent protein.

FIG. 3 exemplifies the linker of the present invention used in the unimolecular FRET biosensor. The present invention will be specifically explained using CFP as an example of the donor fluorescent protein and YFP as an example of the acceptor fluorescent protein. However, as described below, the donor fluorescent protein and the acceptor fluorescent protein are not limited thereto. The sensor domain and the ligand domain are spatially spaced apart from each other in a basal state. In this state, the donor fluorescent protein and the acceptor fluorescent protein are also spatially spaced apart from each other. Therefore, FRET efficiency is low in the basal state. In the activated state, the ligand domain "B" consisting of a conformation recognition domain recognizes a conformational change of the sensor domain "A" induced by various signals such as a phosphorylation or a GTP-binding. As a result, the ligand domain "B" binds to the sensor domain "A," so that the donor approaches the acceptor, which increases the FRET efficiency.

The FRET efficiency is defined as a decrease rate of the fluorescent intensity resulting from the excited donor fluorescent protein in the presence of the acceptor fluorescent protein. However, for convenience, the FRET efficiency as used herein refers to a ratio of the fluorescent intensity of the donor fluorescent protein and the fluorescent intensity of the acceptor fluorescent protein (fluorescent intensity ratio) when the unimolecular FRET biosensor are irradiated at an excitation wavelength of the donor fluorescent protein (see Aoki, K. and M. Matsuda. 2009. Visualization of small GTPase activity with fluorescence resonance energy transfer-based biosensors. Nature Protocol 4:1623-1631, Giepmans, B. N., S. R. Adams, M. H. Ellisman, and R. Y. Tsien. 2006. The fluorescent toolbox for assessing protein location and function. Science 312:217-224, Jares-Erijman, E. A. and T. M. Jovin. Imaging molecular interactions in living cells by FRET microscopy. 2006. Curr. Opin. Chem. Biol. 10:409-416). All references described herein are incorporated by reference in their entirety.

The EV linker according to the present invention has at least 52 to 400 amino acids in length and is a polypeptide which does not form a stable tertiary structure. When the EV linker has less than 52 amino acids, the FRET efficiency in the basal state increases, leading to a decreased gain. When the EV linker has more than 400 amino acids, the FRET biosensor is increased in molecular weight, leading to a low expression level. From the viewpoint of increasing the gain, the EV linker has more preferably 84 or more amino acids, particularly preferably 116 or more amino acids. From the viewpoint of decreasing the molecular weight, the EV linker has more preferably 244 or less amino acids. Therefore, the EV linker has particularly preferably 84 to 244 amino acids in length.

The EV linker of the present invention is a polypeptide which does not form the stable tertiary structure. The EV linker is a linker in which at least 45% of the total number of amino acid residues are glycine and/or alanine (i.e., the sum of the number of glycine residues and the number of alanine residues accounts for at least 45% of the total number of amino acid residues), and which contains alanine in a percentage of at least 10% of the total number of amino acid residues. It is important from the viewpoint of flexibility of the polypeptide that at least 45% of the total number of amino acid residues are glycine and/or alanine. The presence of alanine in a percentage of at least 10% of the total number of amino acid residues enables to achieve a higher gain than that of a linker containing only glycine residues. The EV linker may contain amino acids other than glycine and alanine as long as it does not form the stable tertiary structure. From the viewpoint of obtaining the polypeptide which does not form the stable tertiary structure, for example, serine, threonine, arginine and glutamic acid are particularly preferably contained.

For example, preferred is a polypeptide which contains, besides alanine and glycine, serine and/or threonine in a percentage of at least 10% of the total number of amino acid residues. Example of such polypeptide includes a polypeptide in which at least 95% of the total number of amino acid residues are Gly, Ser, Thr and Ala, and which contains 35% to 65% of Gly, 10% to 40% of Ser and/or Thr, and 10% to 40% of Ala. These amino acid residues are preferably uniformly distributed over a full-length. In particular, preferred is a sequence repeatedly containing Ser-Ala-Gly-Gly, an inverted sequence thereof (i.e., Gly-Gly-Ala-Ser), or Gly-Ala-Gly-Ser. Preferred example thereof includes a sequence which contains repeated units such as Ser-Ala-Gly-Gly, Gly-Gly-Ala-Ser or Gly-Ala-Gly-Ser in a percentage of 95% or more of the total number of amino acid residues, and in which, besides the above described basic sequences (i.e., repeated units), for example, Gly, Ser, Ala or Thr are inserted between the basic sequences in a percentage of less than 5%. Also preferred is a sequence in which Ser is replaced by Thr, which is an amino acid having very similar properties as Ser, in the above described sequence. In the sequence, 13 to 100 repeated units are preferably contained. Specific examples of such linkers include the followings:

EV52 linker
(SEQ ID NO: 12)
SAGGSAGGSAGGSAGGSAGGSGSAGGSAGGSTSAGGSAGGSAGGSAGGS

AGG

EV84 linker
(SEQ ID NO: 15)
SAGGSAGGSAGGSAGGSAGGSGSAGGSAGGSTSAGGSAGGSAGGSAGGS

AGGSGSAGGSAGGSTSAGGSAGGSAGGSAGGSAGG

EV116 linker
(SEQ ID NO: 18)
SAGGSAGGSAGGSAGGSAGGSGSAGGSAGGSTSAGGSAGGSAGGSAGGS

AGGSGSAGGSAGGSTSAGGSAGGSAGGSAGGSAGGSGSAGGSAGGSTSA

GGSAGGSAGGSAGGSAGG

EV180 linker
(SEQ ID NO: 23)
SAGGSAGGSAGGSAGGSAGGSGSAGGSAGGSTSAGGSAGGSAGGSAGGS

AGGSGSAGGSAGGSTSAGGSAGGSAGGSAGGSAGGSGSAGGSAGGSTSA

GGSAGGSAGGSAGGSAGGSGSAGGSAGGSTSAGGSAGGSAGGSAGGSAG

GSGSAGGSAGGSTSAGGSAGGSAGGSAGGSAGG

EV244 linker
(SEQ ID NO: 26)
SAGGSAGGSAGGSAGGSAGGSGSAGGSAGGSTSAGGSAGGSAGGSAGGS

AGGSGSAGGSAGGSTSAGGSAGGSAGGSAGGSAGGSGSAGGSAGGSTSA

GGSAGGSAGGSAGGSAGGSGSAGGSAGGSTSAGGSAGGSAGGSAGGSAG

GSGSAGGSAGGSTSAGGSAGGSAGGSAGGSAGGSGSAGGSAGGSTSAGG

SAGGSAGGSAGGSAGGSGSAGGSAGGSTSAGGSAGGSAGGSAGGSAGG

Also preferred is a polypeptide which contains, besides alanine and glycine, arginine and/or glutamic acid in a percentage of at least 10% of the total number of amino acid residues. Example of such polypeptide includes a polypeptide in which at least 95% of the total number of amino acid residues are glycine, arginine, glutamic acid and alanine, and which contains 4% to 30% of glycine, 5% to 30% of arginine, 5% to 30% of glutamic acid and 30% to 60% of alanine. These amino acid residues are preferably uniformly distributed over a full-length. Examples thereof include the followings:

EV3x8 linker
(SEQ ID NO: 45)
EAAAREAAAREAAARGGEAAAREAAAREAAARGGEAAAREAAAREAAAR

GGEAAAREAAAREAAARGGEAAAREAAAREAAARGGEAAAREAAAREAA

ARGGEAAAREAAAREAAARGGEAAAREAAAREAAAR

-continued

EV6x4 linker (SEQ ID NO: 46)
EAAAREAAAREAAAREAAAREAAAREAAARGGEAAAREAAAREAAAREA

AAREAAAREAAARGGEAAAREAAAREAAAREAAAREAAAREAAARGGEA

AAREAAAREAAARAAREAAAREAAAR

The EV3x8 linker is a polypeptide of 134 amino acid residues in which 8 sequence units of 15 amino acid residues (3 repeats of a sequence EAAAR) are connected via GG sequences. Of the total 134 amino acid residues, there are 72 alanine residues (53.7%), 14 glycine residues (10.4%), 24 glutamic acid residues (17.9%), and 24 arginine residues (17.9%). The sum of the percentage of alanine and glycine is 64.1%. The EV6x4 linker is a polypeptide of 124 amino acid residues. Of the total 124 amino acid residues, there are 71 alanine residues (57.3%), 6 glycine residues (4.8%), 23 glutamic acid residues (18.5%) and 24 arginine residues (19.4%). The sum of the percentage of alanine and glycine is 62.1%.

The EV linker of the present invention increases the gain of the unimolecular FRET biosensor. An insertion site of the EV linker in the unimolecular FRET biosensor may be appropriately selected depending on an increase of a difference in the FRET efficiency between the basal state and the activated state, i.e., the gain. That is, the EV linker may connect any two domains selected from the donor fluorescent protein, the acceptor fluorescent protein, the sensor domain and the ligand domain in the unimolecular FRET biosensor. The EV linker may be inserted between any domains described above. For example, as shown in FIG. 3, the EV linker may be used for connecting between the sensor domain and the ligand domain.

The unimolecular FRET biosensor according to the present invention is a unimolecular FRET biosensor based on the principle of fluorescence resonance energy transfer and is a fused protein containing a sensor domain, a ligand domain, an acceptor fluorescent protein domain, a donor fluorescent protein, and a linker domain which links the sensor domain with the ligand domain. The linker domain consists of the linker of the present invention. Preferred aspects of the unimolecular FRET biosensor according to the present invention includes (1) a biosensor which contains at least one each of the following 5 domains: the donor fluorescent protein domain, the acceptor fluorescent protein domain, the sensor domain, the ligand domain and the linker, and which contains, from the amino-terminus, the donor (or acceptor) fluorescent protein, the sensor (or ligand) domain, the EV linker, the ligand (or sensor) domain and the acceptor (or donor) fluorescent protein; (2) a biosensor which contains at least one each of the following 5 domains: the donor fluorescent protein domain, the acceptor fluorescent protein domain, the sensor domain, the ligand domain and the linker, and which contains, from the amino-terminus, the sensor (or ligand) domain, the donor (or acceptor) fluorescent protein, the EV linker, the acceptor (or donor) fluorescent protein and the ligand (or sensor) domain; (3) a biosensor which contains at least one each of the following 5 domains: the donor fluorescent protein domain, the acceptor fluorescent protein domain, the sensor domain, the ligand domain and the linker, and which contains, from the amino-terminus, the donor (or acceptor) fluorescent protein, the sensor (or ligand) domain, the EV linker, the acceptor (or donor) fluorescent protein and the ligand (or sensor) domain; and (4) a biosensor which contains at least one each of the following 5 domains: the donor fluorescent protein domain, the acceptor fluorescent protein domain, the sensor domain, the ligand domain and the linker, and which contains, from the amino-terminus, the sensor (or ligand) domain, the donor (or acceptor) fluorescent protein, the EV linker, the acceptor (or donor) fluorescent protein and the ligand (or sensor) domain.

When the sensor domain contains a low molecular weight GTP-binding protein or a peptide to be phosphorylated, the aspect (1) is preferred. Thus, the EV linker is preferably present between the ligand domain and the sensor domain in the unimolecular FRET biosensor. Notably, the unimolecular FRET biosensor may not necessarily contain each one of the donor fluorescent protein, the acceptor fluorescent protein, the ligand domain, the acceptor domain and the EV linker, and may contain a plurality of each of the above domains.

The donor fluorescent protein contained in the donor fluorescent protein domain is not particularly limited as long as it can retain the ability to form a FRET pair. From the viewpoint of its function, preferred is CFP or TFP (Teal Fluorescence Protein). On the other hand, the acceptor fluorescent protein contained in the acceptor fluorescent protein domain is also not particularly limited as long as it can retain the ability to form a FRET pair. From the viewpoint of its function, YFP is preferred. The ability to form a FRET pair as used herein means that excitation energy can transfer from an excited donor fluorescent protein to an acceptor fluorescent protein in the close vicinity of the donor fluorescent protein, and the excitation energy transfer can be detected.

The donor fluorescent protein and/or the acceptor fluorescent protein may be a partial protein, that is, may not necessarily be a whole (full-length) protein as long as they can retain the ability to form a FRET pair. When the carboxyl-terminus of an amino acid sequence thereof is shortened, the difference in the FRET efficiency is often increased. Examples of a partial donor fluorescent protein and/or a partial acceptor fluorescent protein include those having preferably at least one, more preferably 1 to 11 deletions at the carboxyl-terminal region in amino acid sequences thereof. Notably, any amino acids in the carboxyl-terminal region region may be deleted. In the case of YFP, preferred are those having preferably at least one, more preferably 1 to 11, further preferably 11 amino acid deletions at the carboxyl-terminal region in amino acid sequences thereof. In the case of CFP, preferred are those having preferably at least one, more preferably 1 to 11, further preferably 11 amino acid deletions at the carboxyl-terminal region in amino acid sequences thereof.

The carboxyl-terminal region as used herein refers to a region consisting of, from the carboxyl-terminus, preferably 1 to 20 amino acids, more preferably 11 or less amino acids in amino acid sequences of GFP-related proteins used in the present invention. Whether the ability to form a FRET pair is retained can be examined as follows. A pair of protein molecules expected to form a FRET pair is co-produced in *E. coli* according to known methods. Cell extract containing the pair of protein molecules is measured for fluorescence intensities at expected excitation wavelengths of each of the pair of protein molecules.

The acceptor fluorescent protein and/or the donor fluorescent protein may have a mutation. The mutation may be introduced into any positions in amino acid sequences of the acceptor fluorescent protein and/or the donor fluorescent protein as long as the ability to form a FRET pair can be retained. Example of the mutation includes a multiple amino acid substitution. Specific examples of the amino acid substitution include Leu65Phe, Phe47Leu or Thr66Ser in a GFP mutant. Such mutations are preferred from the viewpoint of increasing the efficiency in fluorophore formation and increasing the FRET efficiency. The mutations can be introduced according to known methods such as a PCR (polymerase chain reaction). Examples of YFP mutants include Ypet (yellow fluorescent protein for energy transfer) [Nguyen A. W., and P. S. Daugherty. Evolutionary optimization of fluorescent proteins for intracellular FRET. 2005. Nat. Biotechnol. 23:355-360], EYFP (product of Clontech Laboratories, Inc.), and Venus [Nagai, T., K. Ibata, E. S. Park, M. Kubota, K. Mikoshiba, and A. Miyawaki. A variant of yellow fluorescent protein with fast and efficient maturation for cell-biological applications. 2002. Nat. Biotechnol. 20:87-90.] Examples of CFP mutants include CyPet [Nguyen A. W., and P. S. Daugherty. Evolutionary optimization of fluorescent proteins for intracellular FRET. 2005. Nat. Biotechnol. 23:355-360], ECFP (product of Clontech Laboratories, Inc.), SECFP (see PNL 5), and Turquoise (Goedhart, J., L. an Weeren, M. A. Hink, N. 0. Vischer, K. Jalink, and T. W. Gadella, Jr. Bright cyan fluorescent protein variants identified by fluorescence lifetime screening. 2010. Nat. Methods 7:137-139.) Suitable examples of a combination of the acceptor fluorescent protein with the donor fluorescent protein include Venus and ECFP, YPet and ECFP, Venus and Turquoise, and YPet and Turquoise.

A combination of a sensor protein contained in the sensor domain with a ligand contained in the ligand domain is not particularly limited. However, suitable examples thereof include a combination which enables a measurement of a serine-threonine kinase activity, a tyrosine kinase activity, and a low molecular weight GTP-binding protein activity. Examples of the combination for measuring the serine-threonine kinase activity include a combination of a Forkhead-associated (hereinafter referred to as FHA1) domain, a WW (Trp-Trp) domain or a BRCT (BRCA1-C terminal) domain with a peptide sequence containing serine or threonine. Examples of the combination for measuring the tyrosine kinase activity include a combination of a SH2 (Src homology 2) domain or a PTB (phosphotyrosine-binding) domain with a peptide sequence containing tyrosine. Examples of the combination for measuring the low molecular weight GTP-binding protein activity include a combination of a low molecular weight GTP-binding protein belonging to a Ras-family, a Rho-family, a Rab-family, an Arf-family or a Ran-family with a target protein thereof.

From the viewpoint of effectivity, specificity and sensitivity, examples of an elements in the unimolecular FRET biosensor of the present invention and a particularly preferably combination thereof include the followings: a combination in which the sensor domain is the low molecular weight GTP-binding protein Ras, the ligand domain is Raf which is a target protein of the Ras, the donor fluorescent protein is CFP and the acceptor fluorescent protein is YFP; or a combination in which the sensor domain is the low molecular weight GTP-binding protein Rac1, the ligand domain is Pak which is a target protein of the Rac1, the donor fluorescent protein is CFP and the acceptor fluorescent protein is YFP; or a combination in which the sensor domain is the low molecular weight GTP-binding protein Cdc42, the ligand domain is Pak which is a target protein of the Cdc42, the donor fluorescent protein is CFP and the acceptor fluorescent protein is YFP; or a combination in which the sensor domain is a peptide to be phosphorylated by Protein kinase A (A kinase, hereinafter referred to as PKA), the ligand domain is the FHA1 domain, the donor fluorescent protein is CFP and the acceptor fluorescent protein is YFP; or a combination in which the sensor domain is a peptide to be phosphorylated by Extracellular Signal-regulated Kinase (hereinafter referred to as ERK), the ligand domain is the WW domain, the donor fluorescent protein is CFP and the acceptor fluorescent protein is YFP; or a combination in which the sensor domain is a peptide to be phosphorylated by the tyrosine kinase, the ligand domain is the SH2 domain in Crk protein, the donor fluorescent protein is CFP and the acceptor fluorescent protein is YFP.

From the viewpoint a increase in the gain, the acceptor (or donor) fluorescent protein, the ligand (or sensor) domain, the low molecular weight GTP-binding protein and the target protein are, in the unimolecular FRET biosensor containing the EV linker of the present invention, preferably connected in the following orders from the amino-terminus: YFP-FHA1-EV linker-PKA substrate peptide-CFP, YFP-FHA1-EV linker-ERK substrate peptide-CFP, YFP-Raf-EV linker-Ras-CFP, YFP-Rac1-EV linker-Pak-CFP, YFP-Cdc42-EV linker-Pak-CFP, or YFP-CRK SH2 domain-EV linker-tyrosine kinase substrate peptide-CFP. Also, positions of YFP and CFP may be exchanged with each other. Alternatively, various YFP and CFP mutants may be suitably used such as Ypet, CyPet, EYFP (product of Clontech Laboratories, Inc.), ECFP (product of Clontech Laboratories, Inc.), SECFP and Venus.

The unimolecular FRET biosensor of the present invention suitably usable contains, for example, a peptide tag, other fluorescent proteins, an intracellular localization signal, or a protein-protein interaction regulating domain at the N-terminus, the C-terminus or internally as long as it contains the above-described five domains in order to alter an intracellular distribution depending on the intended purpose or to allow the unimolecular FRET biosensor to be easily purified.

Notably, whether the EV linker of the present invention exhibits a desired effect can be evaluated according to the method of Example 1 described below.

The present invention also provides a gene (DNA) encoding the EV linker according to the present invention and a gene (DNA) encoding the unimolecular FRET biosensor according to the present invention. The gene of the EV linker can be chemically synthesized. Component proteins other than the EV linker in the unimolecular FRET biosensor can be each produced according to conventional methods. For example, their gene sequences can be available from, for example, GenBank. Based on thus obtained gene sequences, known PCR amplifications, restriction enzyme cleavages, and ligations are performed.

The present invention also provides an expression vector containing the gene. Such vector can be constructed by inserting the gene encoding the EV linker or the unimolecular FRET biosensor of the present invention into a known prokaryotic expression vector (e.g., pGEX-2T; product of GE Healthcare), a known eukaryotic expression vector (e.g., pCAGGS [Niwa, H., K. Yamamura, and J. Miyazaki. 1991. Efficient selection for high-expression transfectants with a novel eukaryotic vector. Gene 108:193-200.]) or a known viral vector (e.g., pCX4 [Iwahara, T., T. Akagi, Y. Fujitsuka, and H. Hanafusa. 2004. CrkII regulates focal adhesion kinase activation by making a complex with Crk-associated substrate, p 130 Cas. Proc. Natl. Acad. Sci. U.S. A 101:17693-17698]) according to known methods.

The present invention also provides a transformed cell and a transgenic non-human animal harboring the expression vector. Such transformed cell can be obtained by introducing the expression vector into an intended cell. A method for introducing the expression vector into the cell is not particularly limited, and may be any known transfection methods or viral infection methods. Examples thereof include a calcium phosphate method, a lipofection method, an electroporation method or a transposon-based method. The cell is not particularly limited, and may be any prokaryotic or eukaryotic cells. Examples of the eukaryotic cell include HeLa cells derived from human cancer, HEK293T cells derived from human embryonic kidney, MDCK cells derived from canine kidney, COS7 cells derived from monkey kidney, rat C6 glioma cells and yeast. Example of the prokaryotic cell includes *E. coli*. Additionally, other various cells may be used.

Meanwhile, the transgenic non-human animal can be generated by directly introducing the expression vector into an individual (e.g., mouse) using known methods such as a method for microinjecting a plasmid DNA into a nucleus of a fertilized mouse egg or a Tol2 transposase-mediated method [Sumiyama, K., K. Kawakami, and K. Yagita. 2010. A simple and highly efficient transgenesis method in mice with the Tol2 transposon system and cytoplasmic microinjection. Genomics 95:306-311.]. The transgenic non-human animal is not particularly limited as long as it is not human. Examples thereof include mouse, rat, pig, zebrafish and *C. elegans*. Preferred is mouse from the viewpoint of an application in the pharmaceutical industry.

The present invention also provides a method for measuring a serine-threonine kinase activity, a tyrosine kinase activity, or a low molecular weight GTP-binding protein activity, the method including detecting FRET with the unimolecular FRET biosensor of the present invention. Examples of a method for detecting FRET with the unimolecular FRET biosensor of the present invention include a method in which a unimolecular FRET biosensor-expressing cell line is observed under a fluorescence microscope, followed by a time-lapse imaging and a method in which a unimolecular FRET biosensor-expressing cell line is analyzed with a flow cytometer. Such methods enable the serine-threonine kinase activity, the tyrosine kinase activity and the low molecular weight GTP-binding protein activity to be measured by detecting FRET occurred with the unimolecular FRET biosensor according to the present invention.

The present invention also provides a measurement method for measuring a serine-threonine kinase activity, a tyrosine kinase activity, or a low molecular weight GTP-binding protein activity including detecting FRET using the transformed cell and the transgenic non-human animal according to the present invention. The serine-threonine kinase activity, the tyrosine kinase activity and the low molecular weight GTP-binding protein activity can be measured using the unimolecular FRET biosensor containing a sensor domain and a ligand domain which domains may be used for measuring the serine-threonine kinase activity, the tyrosine kinase activity, or the low molecular weight GTP-binding protein activity. A method for detecting FRET is not particularly limited as long as it can detect excitation energy transfer due to FRET. For example, a microscope, a flow cytometer, a spectrophotometer or a fluorescent ELISA reader can be used for the FRET. Using the measurement method, the serine-threonine kinase activity, the tyrosine kinase activity and the low molecular weight GTP-binding protein activity can be directly measured in the cell or animal by detecting FRET. In such a case, a calibration curve may be separately generated as follows: a phosphorylation rate is calculated using a phosphorylation-specific antibody, and thus the corresponding FRET efficiency is determined; or a GTP/GDP ratio (or GTP/(GDP+GTP) ratio) (both in molar ratio) is calculated by measuring a GTP-bound form of the low molecular weight GTP-binding protein and a GDP-bound form of the low molecular weight GTP-binding protein resulting from a release of an inorganic phosphate from GTP, and thus the corresponding FRET efficiency is determined. Such calibration curve enables the phosphorylation rate or the GTP/GDP ratio to be calculated based on the FRET efficiency in the cell or animal.

For example, the following method is specifically exemplified.

The unimolecular FRET biosensor-expressing transformed cell or transgenic non-human animal of the present invention is observed under a fluorescence microscope to thereby directly detect a change in the FRET efficiency before and after a conformational change of the sensor domain, which can be performed according to Aoki, K. and M. Matsuda. 2009. Visualization of small GTPase activity with fluorescence resonance energy transfer-based biosensors. Nature Protocol 4:1623-1631. In the case of the transgenic non-human animal, a body part which can be easily fixed (e.g., external ear) is preferably observed.

The fluorescence microscope to be used is not particularly limited. However, an inverted fluorescence microscope (IX81, product of Olympus Corporation) equipped with a known xenon light source, a fluorescence excitation filter wheel, a fluorescence emission filter wheel, and a high sensitive cooled CCD camera. The filters and camera images can desirably be controlled and analyzed with Meta Morph image analysis software (product of Molecular Devices, LLC).

The cell or animal is irradiated with excitation light of the donor fluorescent protein. At a fluorescence wavelength of the donor fluorescent protein, an image is taken by the CCD camera. Then, a fluorescence wavelength of the acceptor fluorescent protein, an image is taken by the CCD camera. A ratio of fluorescence intensities in both images is determined to thereby calculate the FRET efficiency at each measuring points.

According to the present invention, there are provided a unimolecular FRET biosensor containing the EV linker according to the present invention and allowing the serine-threonine kinase activity, the tyrosine kinase activity and the low molecular weight GTP-binding protein activity to be non-invasively measured; and a gene encoding the unimolecular FRET biosensor. The biosensor is excited with light in a visible light region, which is a reason why the activities can be non-invasively measured. There are also provided a transformed cell and a transgenic non-human animal harboring the expression vector which is useful to express the unimolecular FRET biosensor and to non-invasively measure the serine-threonine kinase activity, the tyrosine kinase activity and the low molecular weight GTP-binding protein activity; and a measurement method for measuring the serine-threonine kinase activity, the tyrosine kinase activity and the low molecular weight GTP-binding protein activity by means of the unimolecular FRET biosensor containing the EV linker (hereinafter may be referred to as "EV linker containing-unimolecular FRET biosensor"). Thus, the serine-threonine kinase activity, the tyrosine kinase activity and the low molecular weight GTP-binding protein activity can be non-invasively determined in cells or individuals, which can provide great advantages in understanding of biological phenomena as well as in drug developments (e.g., therapeutic agents or prophylactic agents for cancers, autoimmune diseases and allergic diseases).

A further aspect of the present invention is a method for screening a regulator of the serine-threonine kinase activity, the tyrosine kinase activity and the low molecular weight GTP-binding protein activity. That is, the above method is a method for screening a regulator of the serine-threonine kinase activity, the tyrosine kinase activity, or the low molecular weight GTP-binding protein activity including (a) contacting a test substance with the transformed cell of the present invention; and (b) detecting FRET to thereby detect a change in the serine-threonine kinase activity, the tyrosine kinase activity, or the low molecular weight GTP-binding protein activity. The transformed cell of the present invention is a transformed cell harboring expression vector which contains a gene of the EV linker containing-unimolecular FRET biosensor and which expresses the unimolecular FRET biosensor of the present invention. According to the screening method of the present invention, substances and salt thereof can be efficiently screened which regulate the serine-threonine kinase activity, the tyrosine kinase activity and the low molecular weight GTP-binding protein activity (i.e., regulators of the serine-threonine kinase activity, the tyrosine kinase activity and the low molecular weight GTP-binding protein activity) by constructing a cell which expresses the EV linker containing-unimolecular FRET biosensor of the present invention and using a bioassay system. The test substance used in the method is not particularly limited. Examples thereof include a peptide, a protein, a non-peptidic substance, a synthetic substance and a fermentation product.

EXAMPLES

The present invention will be explained with reference to the following Examples. However, a scope of the present invention is not limited thereto.

Example 1

Measurement of Serine-Threonine Kinase A (PKA) Enzyme Activity with Eevee-PKAs (1) Construction of Gene Encoding EV Linker Containing-Unimolecular FRET Biosensor for Measurement of PKA Enzyme Activity (i) Construction of Platform Eevee-PKA-G72 (3520 NES) Gene for Insertion of EV Linker Gene A unimolecular FRET biosensor Eevee-PKA-G72 (3520 NES) gene was constructed using known methods (e.g., PCR) (see FIG. 3). The unimolecular FRET biosensor contains, from the amino-terminus, YFP, a linker, a ligand domain (herein, FHA1 domain which specifically binds to a phosphorylated threonine), a linker, a substrate sequence to be phosphorylated by PKA, a linker, and a CFP donor fluorescent protein. There will be described a nucleotide sequence (SEQ ID NO: 1) of the resultant Eevee-PKA-G72 and a predicted amino acid sequence thereof (SEQ ID NO: 2).
nt 1-714: Aequorea YFP (YPet)
nt 715-720: linker (Leu-Glu)
nt 721-1143: FHA1 domain of yeast Rad53 gene
nt 1144-1149: linker (Gly-Thr)
nt 1150-1392: glycine linker
nt 1393-1437: PKA substrate sequence
nt 1438-1446: linker (Gly-Gly-Arg)
nt 1447-2163: Aequorea CFP (ECFP)
nt 2164-2169: linker (Ser-Arg)
nt 2170-2205: nuclear export signal (NES)
nt 2206-2208: stop codon
(ii) Synthesis of EV20 Linker and Construction of Eevee-PKA-20 Gene (3532 NES)
A sense-primer F_20 a.a_linker (SEQ ID NO: 3) was annealed with an antisense-primer R_20 a.a_linker (SEQ ID NO: 4). The resultant annealed product was inserted into a restriction enzyme Asp718I/Aor13HI cleavage site in 3520 NES. A 20 a.a. linker encoded by the inserted nucleotides is referred to as "EV20 linker" (SEQ ID NO: 5). Then, YPet was replaced by Venus in the above unimolecular FRET biosensor. The resultant unimolecular FRET biosensor was designated as "Eevee-PKA-20 (3532 NES)". There will be described a nucleotide sequence (SEQ ID NO: 6) of the Eevee-PKA-20 and a predicted amino acid sequence thereof (SEQ ID NO: 7).
nt 1-714: Aequorea YFP (Venus)
nt 715-720: linker (Leu-Glu)
nt 721-1143: FHA1 domain of yeast Rad53 gene
nt 1143-1149: linker (Gly-Thr)
nt 1150-1209: EV20linker (SEQ ID NO: 5)
nt 1210-1215: linker (Ser-Gly)
nt 1216-1239: PKA substrate sequence
nt 1239-1248: linker (Gly-Gly-Arg)
nt 1249-1965: Aequorea CFP (ECFP)
nt 1966-1971: linker (Ser-Arg)
nt 1972-2007: nuclear export signal (NES)
nt 2008-2010: stop codon
(iii) Construction of Eevee-PKA-52 (3535 NES)
A pEevee-PKA-20, which was a mammalian cell expression vector of the Eevee-PKA-20, was cleaved with restriction enzymes EcoRI and Asp718I. The resultant larger cleavage product was used to prepare a vector. The pEevee-PKA-20 fragment was ligated with a linker-containing fragment which is a cleavage product with EcoRI/Aor13HI and a DNA fragment which was obtained by annealing a sense-primer F_10 a.a_linker (SEQ ID NO: 8) with an antisense-primer R_10 a.a_linker (SEQ ID NO: 9), resulting in a pEevee-PKA-52. There will be described a nucleotide sequence (SEQ ID NO: 10) of the Eevee-PKA-52 and a predicted amino acid sequence thereof (SEQ ID NO: 11).
nt 1-714: Aequorea YFP (Venus)
nt 715-720: linker (Leu-Glu)
nt 721-1143: FHA1 domain of yeast Rad53 gene
nt 1144-1149: linker (Gly-Thr)
nt 1150-1305: EV52 linker (SEQ ID NO: 12)
nt 1306-1311: linker (Ser-Gly)
nt 1312-1335: PKA substrate sequence
nt 1336-1344: linker (Gly-Gly-Arg)
nt 1345-2061: Aequorea CFP (ECFP)
nt 2062-2067: linker (Ser-Arg)
nt 2068-2103: nuclear export signal (NES)
nt 2104-2106: stop codon
(iv) Construction of pEevee-PKA-84 (3537 NES)
The pEevee-PKA-20, which was a mammalian cell expression vector of the Eevee-PKA-20, was cleaved with restriction enzymes EcoRI and Asp718I. The resultant larger cleavage product was used to prepare a vector. The pEevee-PKA-20 fragment was ligated with a linker-containing fragment which is a cleavage product with EcoRI/Aor13HI and a DNA fragment which was obtained by annealing a sense-primer F_10 a.a_linker (SEQ ID NO: 8) with an antisense-primer R_10 a.a_linker (SEQ ID NO: 9), resulting in an Eevee-PKA-84. There will be described a nucleotide sequence (SEQ ID NO: 13) of the Eevee-PKA-84 and a predicted amino acid sequence thereof (SEQ ID NO: 14).
nt 1-714: Aequorea YFP (YPet)
nt 715-720: linker (Leu-Glu)
nt 721-1143: FHA1 domain of yeast Rad53 gene
nt 1144-1149: linker (Gly-Thr)
nt 1150-1401: EV84 linker (SEQ ID NO: 15)
nt 1402-1407: linker (Ser-Gly)
nt 1408-1431: PKA substrate sequence
nt 1432-1440: linker (Gly-Gly-Arg)
nt 1441-2157: Aequorea CFP (ECFP)
nt 2158-2163: linker (Ser-Arg)
nt 2164-2199: nuclear export signal (NES)
nt 2200-2202: stop codon (v) Construction of Eevee-PKA-116 (3536 NES)

The pEevee-PKA-20, which was a mammalian cell expression vector of the Eevee-PKA-52, was cleaved with restriction enzymes EcoRI and Asp718I. The resultant larger cleavage product was used to prepare a vector. The pEevee-PKA-52 fragment was ligated with a linker-containing fragment which is a cleavage product with EcoRI/Aor13HI and a DNA fragment which was obtained by annealing a sense-primer F_10 a.a_linker (SEQ ID NO: 8) with an antisense-primer R_10 a.a_linker (SEQ ID NO: 9), resulting in an Eevee-PKA-116. There will be described a nucleotide sequence (SEQ ID NO: 16) of the Eevee-PKA-116 and a predicted amino acid sequence thereof (SEQ ID NO: 17).

nt 1-714: Aequorea YFP (YPet)
nt 715-720: linker (Leu-Glu)
nt 721-1143: FHA1 domain of yeast Rad53 gene
nt 1144-1149: linker (Gly-Thr)
nt 1150-1497: EV116 linker (SEQ ID NO: 18)
nt 1498-1503: linker (Ser-Gly)
nt 1504-1527: PKA substrate sequence
nt 1528-1536: linker (Gly-Gly-Arg)
nt 1537-2247: Aequorea CFP (ECFP)
nt 2248-2253: linker (Ser-Arg)
nt 2254-2289: nuclear export signal (NES)
nt 2290-2292: stop codon (vi) Construction of pEevee-PKA-5 (3522 NES)

A unimolecular FRET biosensor pEevee-PKA-5 was constructed using known methods (e.g., PCR). There will be described a nucleotide sequence (SEQ ID NO: 19) of the pEevee-PKA-5 and a predicted amino acid sequence thereof (SEQ ID NO: 20).

nt 1-714: Aequorea YFP (Venus)
nt 715-720: linker (Leu-Glu)
nt 721-1143: FHA1 domain of yeast Rad53 gene
nt 1144-1170: linker (Gly-Thr-Gly-Gly-Ser-Gly-Gly-Ser-Gly)
nt 1171-1194: PKA substrate sequence
nt 1195-1203: linker (Gly-Gly-Arg)
nt 1204-1920: Aequorea CFP (ECFP)
nt 1921-1926: linker (Ser-Arg)
nt 1927-1962: nuclear export signal (NES)
nt 1963-1965: stop codon (vii) Construction of pEevee-PKA-180 (3597 NES)

The pEevee-PKA-116, was cleaved with restriction enzymes EcoRI and Asp718I. The resultant larger cleavage product was used to prepare a vector. The pEevee-PKA-116 fragment was ligated with a linker-containing fragment which is a cleavage product with EcoRI/Aor13HI and a DNA fragment which was obtained by annealing a sense-primer F_10 a.a_linker (SEQ ID NO: 8) with an antisense-primer R_10 a.a_linker (SEQ ID NO: 9), resulting in an Eevee-PKA-180. Then, Venus was replaced by YPet in the above unimolecular FRET biosensor. There will be described a nucleotide sequence (SEQ ID NO: 21) of the Eevee-PKA-180 and a predicted amino acid sequence thereof (SEQ ID NO: 22).

nt 1-714: Aequorea YFP (YPet)
nt 715-720: linker (Leu-Glu)
nt 721-1143: FHA1 domain of yeast Rad53 gene
nt 1144-1149: linker (Gly-Thr)
nt 1150-1689: EV180 linker (SEQ ID NO: 23)
nt 1690-1695: linker (Ser-Gly)
nt 1696-1719: PKA substrate sequence
nt 1720-1728: linker (Gly-Gly-Arg)
nt 1729-2439: Aequorea CFP (ECFP)
nt 2440-2445: linker (Ser-Arg)
nt 2446-2481: nuclear export signal (NES)
nt 2482-2484: stop codon (vii) Construction of pEevee-PKA-244 (3598 NES)

The pEevee-PKA-116 was cleaved with restriction enzymes EcoRI and Asp718I. The resultant larger cleavage product was used to prepare a vector. The pEevee-PKA-116 fragment was ligated with a linker-containing fragment which is a cleavage product with EcoRI/Aor13HI and a DNA fragment which was obtained by annealing a sense-primer F_10 a.a_linker (SEQ ID NO: 8) with an antisense-primer R_10 a.a_linker (SEQ ID NO: 9), resulting in a pEevee-PKA-244. There will be described a nucleotide sequence (SEQ ID NO: 24) of the pEevee-PKA-244 and a predicted amino acid sequence thereof (SEQ ID NO: 25).

nt 1-714: Aequorea YFP (YPet)
nt 715-720: linker (Leu-Glu)
nt 721-1143: FHA1 domain of yeast Rad53 gene
nt 1144-1149: linker (Gly-Thr)
nt 1150-1881: EV244 linker (SEQ ID NO: 26)
nt 1882-1887: linker (Ser-Gly)
nt 1888-1911: PKA substrate sequence
nt 1912-1920: linker (Gly-Gly-Arg)
nt 1921-2631: Aequorea CFP (ECFP)
nt 2632-2637: linker (Ser-Arg)
nt 2638-2673: nuclear export signal (NES)
nt 2674-2676: stop codon (2) Expression of EV Linker Containing-Unimolecular FRET Biosensor (EeVee-PKA) in Mammalian Cell and Time-Lapse Fluorescence Microscopy Analysis Here, PKA-biosensors containing various lengths of the EV-linkers and mammalian cell expression vectors thereof are collectively referred to as "EeVee-PKAs" and "pEevee-PKAs", respectively. As the mammalian cell expression vectors, pCAGGS [Niwa, H., K. Yamamura, and J. Miyazaki. 1991. Efficient selection for high-expression transfectants with a novel eukaryotic vector. Gene 108:193-200.] may be optimally used. HeLa cells derived from cervical cancer were cultured in a DMEM medium (product of INVITROGEN) supplemented with 10% fetal bovine serum. The pEeVee-PKAs obtained in the step (1) were transfected into the HeLa cells by 293 fectin (product of INVITROGEN) according to the protocol supplied with the reagent. Post-transfected HeLa cells were cultured in the DMEM medium (product of INVITROGEN) supplemented with 10% fetal bovine serum to thereby express Eevee-PKA proteins. Twenty-four hours after transfection, the cultured cells were observed under a time-lapse fluorescence microscope.

The microscope was the inverted fluorescence microscope (IX81, product of Olympus Corporation) equipped with a xenon light source, a fluorescence excitation filter wheel device and a fluorescence emission filter wheel device (product of Ludl Electronic Products Ltd.), and a high sensitive cooled CCD camera (CoolSNAP-HQ, product of NIPPON ROPER K.K.) Upon observation, Meta Morph image analysis software (product of Molecular Devices, LLC) was used to control the microscope and to analyse observation results. A fluorescence excitation filter, a fluorescence emission filter and a dichroic mirror were purchased from Omega SA.

The cultured cells were irradiated with excitation light at 440 nm. An image was taken by the CCD camera at a fluorescence wavelength of the CFP donor, i.e., 480 nm. Then, an image was taken by the CCD camera at a fluorescence wavelength of the YFP acceptor, i.e., 530 nm. Based on the both image data, a ratio between fluorescence intensities in both images was determined to thereby use as an index of the FRET efficiency at each measuring points.

Figure 4:
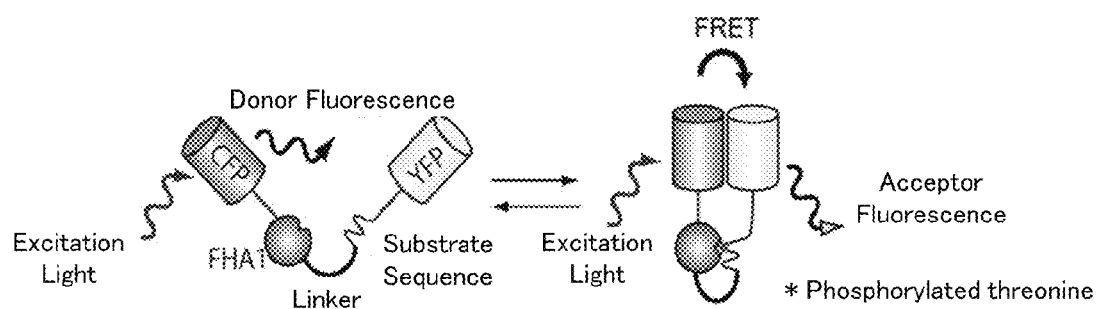
FIG. 4 illustrates a role of a linker domain in a unimolecular FRET biosensor containing a sensor domain and a ligand domain based on FRET. In this figure, a biosensor for PKA, Eevee-PKA, is shown by way of example. The sensor domain contains a substrate sequence to be specifically phosphorylated by PKA. The ligand domain is a FHA1 domain of Rad1 protein which is known to bind to the phosphorylated peptide. When the substrate sequence in the sensor domain is phosphorylated by PKA, the ligand domain binds to the phosphorylated sensor domain. Thus, a FRET donor fluorescent protein (CFP) approaches a FRET acceptor fluorescent protein (YFP). As a result, FRET occurs and fluorescence can be detected from the FRET acceptor fluorescent protein.
Figure 5:
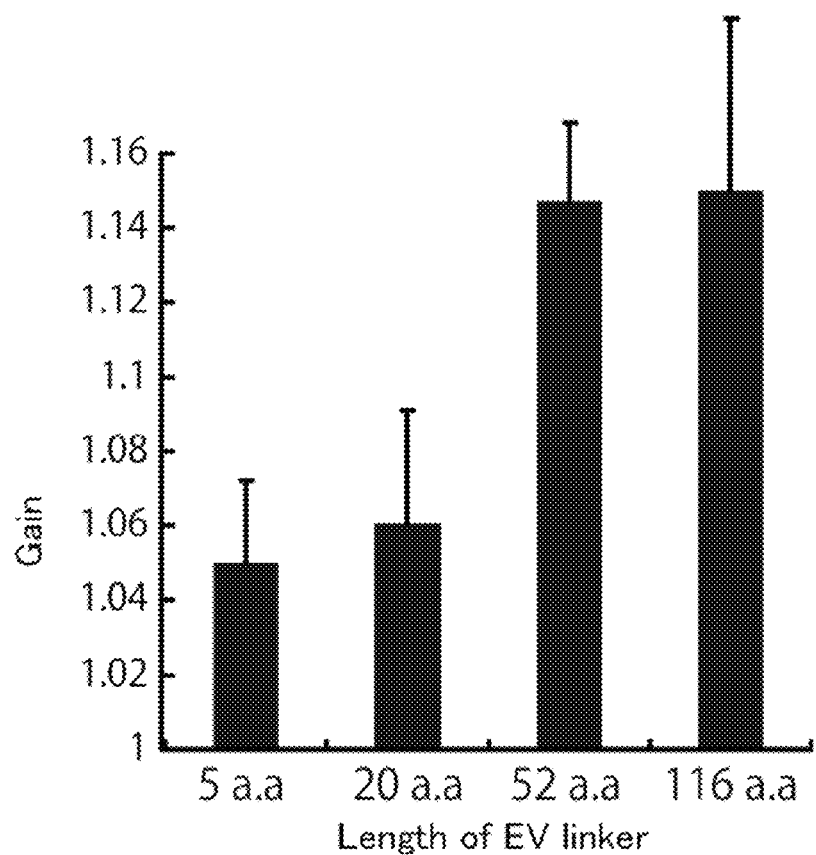
FIG. 5 illustrates a relationship between lengths of EV linkers and gains. Eevee-PKAs having various lengths were expressed in HeLa cells. After 24 hours, PKAs were activated with 1 mM dibutyryl-cAMP. FRET/CFP fluorescence ratios were measured before and 30 min after stimulation. The "gain" is defined as a percentage of increase of the FRET/CFP fluorescence ratio relative to that of before stimulation.

The gain of the Eevee-PKAs can be determined by comparing the FRET efficiencies before and after stimulation with 1 mM dibutyryl cAMP which is an activating agent of PKA. As can be seen from FIG. 4, the EV linkers having 52 a.a. or more have markedly increased gains due to the activation of PKA.

Figure 6:
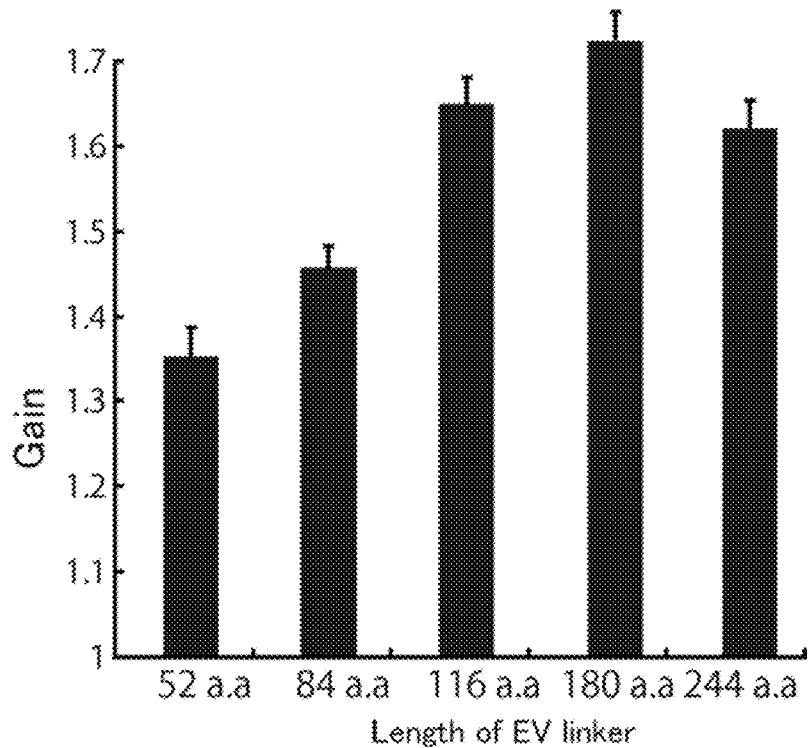
FIG. 6 demonstrates that the EV linkers can exhibit more significant effect when a YPet mutant is used as the YFP acceptor protein. Eevee-PKAs having the YPets and varying lengths of EV linkers were constructed. Then, these Eevee-PKAs were expressed in HeLa cells. After 24 hours, PKAs were activated with 1 mM dibutyryl-cAMP. FRET/CFP fluorescence ratios were measured before and 30 min after stimulation. The "gain" is defined as a percentage of increase of the FRET/CFP fluorescence ratio relative to that of before stimulation.

Additionally, when the YFP donor protein was replaced by, for example, YPet, which has been optimized for the FRET, the gains were more significantly increased (see FIG. 6). However, the increasing effect reached a zenith at 116 a.a, and the gain cannot be significantly increased even when having longer linkers.

Figure 7A:
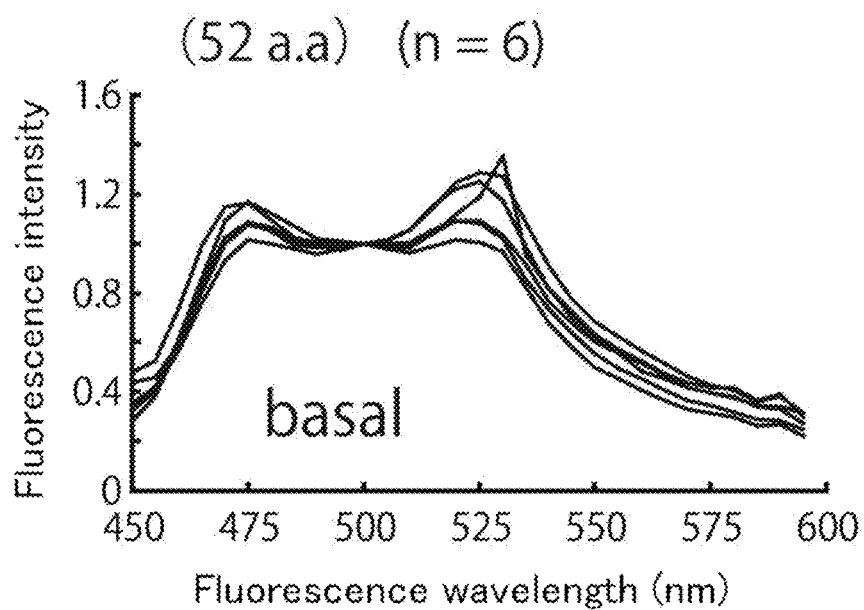
FIG. 7A demonstrates that an effect of the EV linker results from a reduction of FRET at the basal state.
Figure 7B:
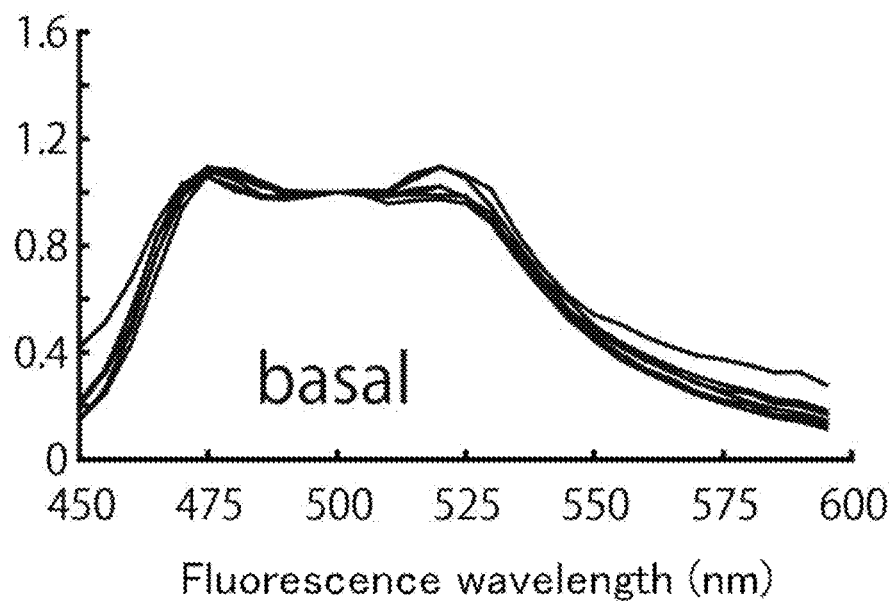
FIG. 7B illustrates measurement results of Eevee-PKA-84 measured in the same manner as in FIG. 7A.
Figure 7C:
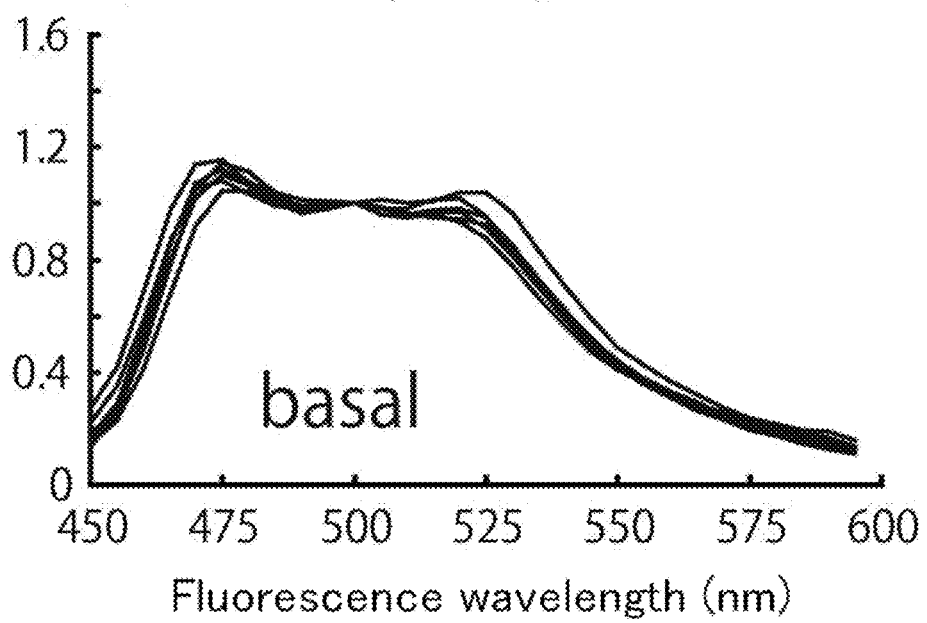
FIG. 7C illustrates measurement results of Eevee-PKA-116 measured in the same manner as in FIG. 7A. As can be seen from these figures, as the EV linkers become longer, then fluorescence intensities at 530 nm, which indicate FRET at the basal state, are significantly reduced.

In order to examine a cause of the increase in the gain, fluorescent profiles at the basal state were determined (see FIGS. 7A, 7B and 7C). It has been found that the longer the EV linker is, the lower fluorescence of the YFP donor protein at the basal state is. That is, it has been found that the EV linker increases the gain by reducing the FRET at the basal state. This effect could be achieved with linkers having up to 244 a.a.

(3) Immunoblotting Analysis of Phosphorylation Levels of Eevee-PKAs

Figure 8A:
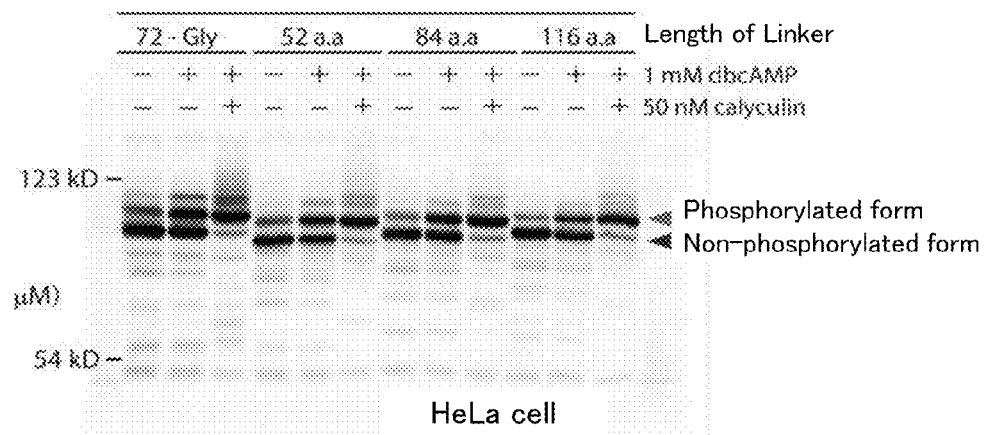
FIG. 8A demonstrates that a reduction of FRET efficiency at the basal state by the EV linker results from a reduction of phosphorylations. The Eevee-PKAs were expressed in HeLa cells in the same manner as in FIG. 7A. Untreated cells, cells treated with 1 mM dibutyryl-cAMP for 15 min, and cells treated with 1 mM dibutyryl-cAMP and 50 nM Calyculin for 15 min were separated with a 6% SDS polyacrylamide gels containing 50 µM Phos-tag. Then, the samples were subjected to an immunoblotting analysis with anti-GFP antibodies and mouse monoclonal antibodies. As can be seen from this figure, as the EV linkers become shorter, then phosphorylation levels at the basal state are reduced.
Figure 8B:
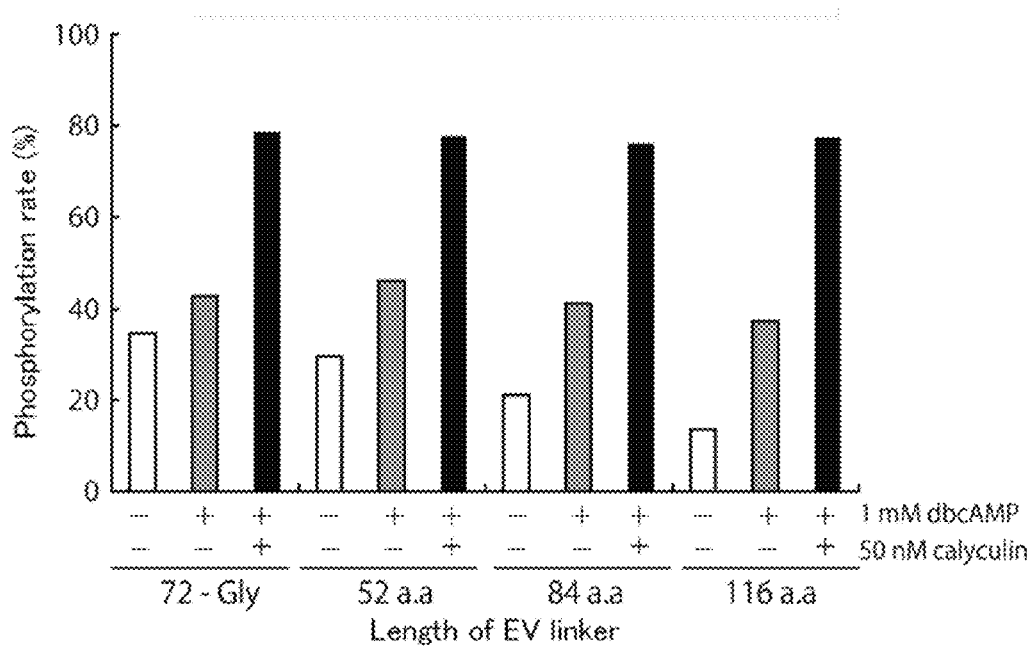
FIG. 8B illustrates a graph representing phosphorylation levels in FIG. 8A.

As described above, the Eevee-PKAs were expressed in HeLa cells. After 24 hours, the cells were treated with 1 mM dibutyryl-cAMP and 50 nM Calyculin. Thereafter, the cells were solubilized according to known methods, followed by separation with SDS-PAGE. Proteins were separated using a 6% polyacrylamide gel containing 50 μM Phos-tag (product of Phos-tag Consortium). The gel was transferred to a PVDF membrane (product of Millipore) and sequentially reacted with anti-GFP antibodies (in-house) and IR Dye 800 CW-labeled anti-rabbit antibodies (product of LI-COR Biosciences) to thereby detect the Eevee-PKA proteins. Fluorescence labeled antibodies bound to the Eevee-PKA proteins were quantified by Odyssey Fluorescence Analyzer (product of LI-COR Biosciences). As can be seen from FIGS. 8A and 8B, the EV linkers significantly reduce phosphorylation levels at the basal state. That is, the ligand domain generally binds to the sensor domain to thereby inhibit the activated sensor domain from returning to the basal state. The EV linkers suppress the inhibitory effect to thereby reduce FRET at the basal state, which increases the gain.

Example 2

Figure 9A:
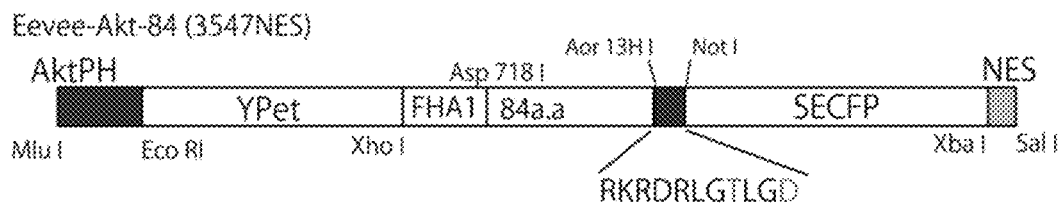
FIG. 9A illustrates a structure of an Akt biosensor (Eevee-Akt-84) having a $PIP_3$-binding domain. Here, "84 a.a." denotes an EV84 linker, "AktPH" denotes a PH domain of Akt protein, and "NES" denotes a nuclear export signal.
Figure 9B:
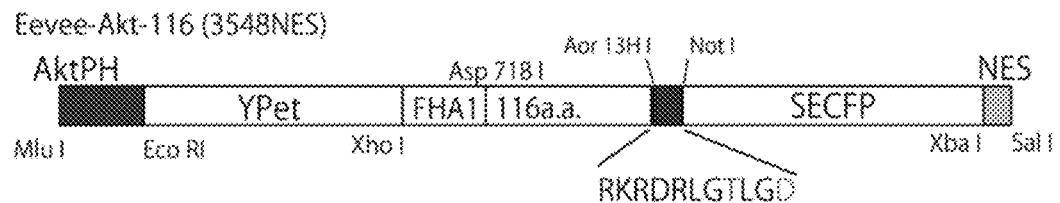
FIG. 9B illustrates a structure of an Akt biosensor (Eevee-Akt-116) having a PIPS-binding domain in the same manner as in FIG. 9A. Here, "116 a.a." denotes an EV116 linker.

Measurement of Enzyme Activity of Serine-Threonine Kinase Akt with Eevee-PKAs (1) Construction of Gene Encoding EV Linker Containing-Unimolecular FRET Biosensor for Measurement of Serine-Threonine Kinase Akt Enzyme Activity There were constructed sequences in which PKA substrate sequences in Eevee-Akt-84 (3547 NES) and Eevee-Akt-116 (3548 NES) were replaced by amino acid sequences suitable for phosphorylation of Akt by means of, for example, synthetic primers. The above sequences were inserted into the Eevee-PKAs and PH domains of Akt were added to the amino-termini. There will be described nucleotide sequences (SEQ ID NOs: 27 and 29) of the resultant Eevee-Akt-84 and Eevee-Akt-116, and predicted amino acid sequences thereof (SEQ ID NOs: 28 and 30). Structures thereof are shown in FIGS. 9A and 9B.

Figure 10:
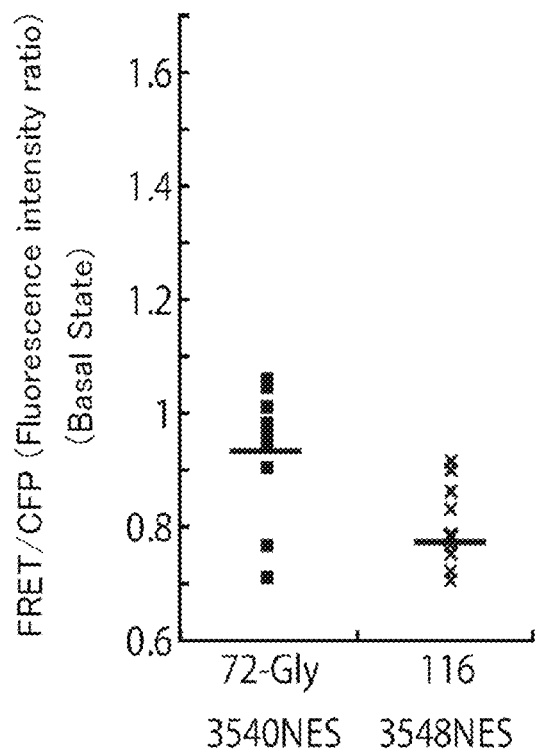
FIG. 10 demonstrates that a reduction of FRET at the basal state by the EV linker is also observed in the Akt biosensors. Eevee-Akt was expressed in COS7 cells and measured for FRET/CFP fluorescence ratio. Five or more cells were measured and their measurement results are shown with average values. It has been found that, the EV116 linker has lower FRET at the basal state than that of a 72-Gly linker.
Figure 11A:
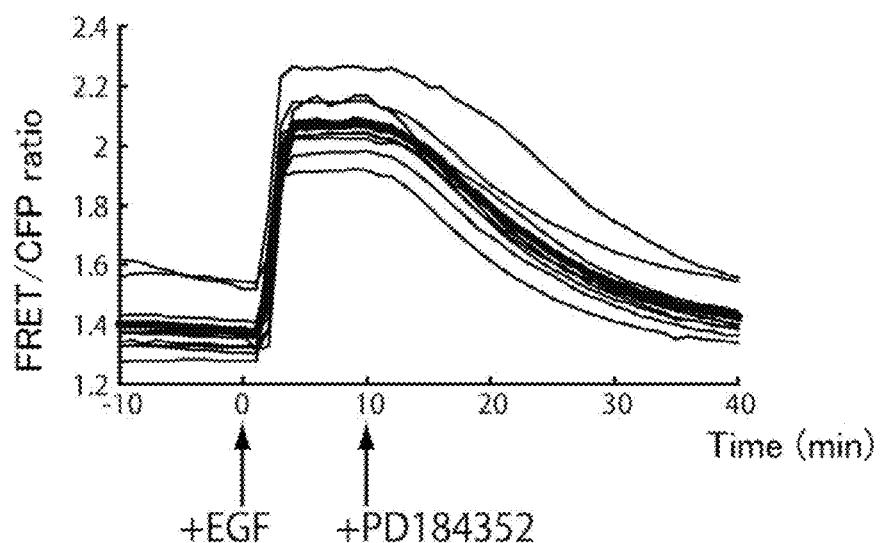
FIG. 11A illustrates measurement results of ERK activities when using Eevee-ERK compared with that of a glycine linker.
Figure 11B:
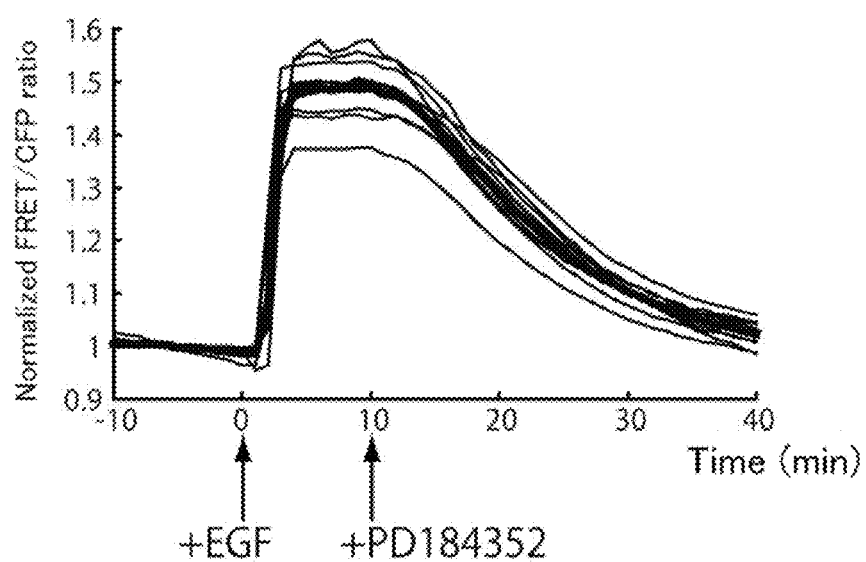
FIG. 11B illustrates a graph of the FRET/CFP fluorescence ratios normalized against that of at pre-stimulation.
Figure 11C:
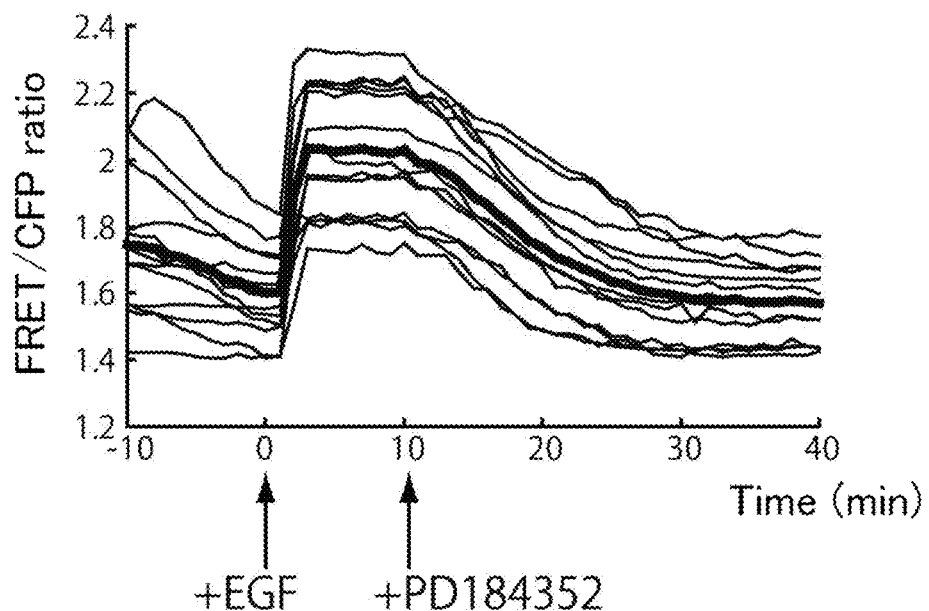
FIG. 11C illustrates measurement results of EKAR-1667 nes (72-Gly linker) (1667 NES) containing a glycine linker in the same manner as FIG. 11A.
Figure 11D:
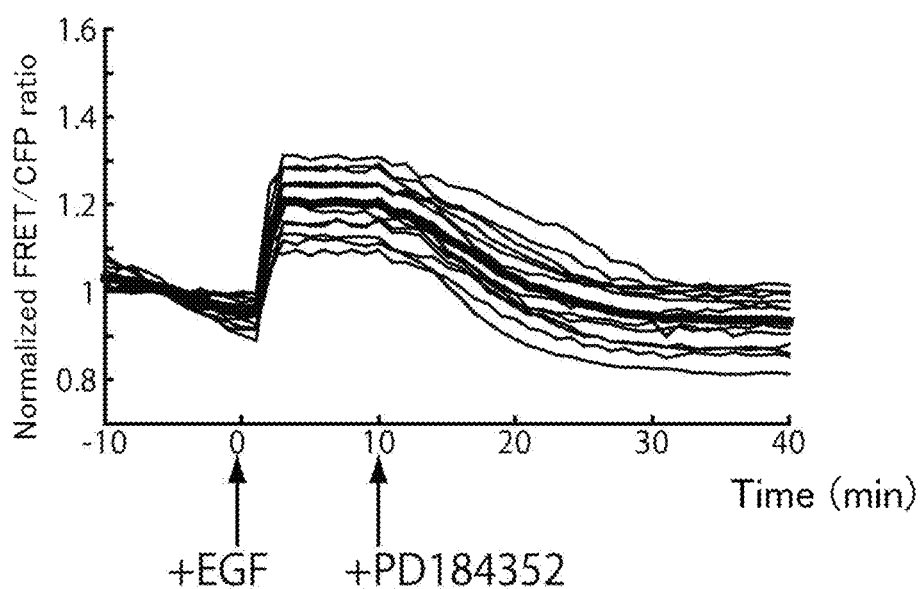
FIG. 11D illustrates a graph of the FRET/CFP fluorescence ratios normalized against that of pre-stimulation. An upper limit of the measured FRET/CFP is about 2.2, indicating that a lower basal FRET efficiency results in a higher gain of the Eevee-ERK containing the EV116 linker (see FIGS. 11A and 11B) than that of EKAR-1667 nes containing the glycine linker.

Eevee-Akt-84 (3547 NES)
    nt 1-453: AH domain of Akt protein
    nt 454-462: linker (Glu-Phe-Gly)
    nt 463-1176: Aequorea YFP (YPet)
    nt 1177-1182: linker (Leu-Glu)
    nt 1183-1605: FHA1 domain of yeast Rad53 gene
    nt 1606-1611: linker (Gly-Thr)
    nt 1612-1863: EV84 linker
    nt 1864-1869: linker (Ser-Gly)
    nt 1870-1902: PKA substrate sequence
    nt 1903-1911: linker (Gly-Gly-Arg)
    nt 1912-2622: Aequorea CFP (ECFP)
    nt 2623-2628: linker (Ser-Arg)
    nt 2629-2664: nuclear export signal (NES)
    nt 2665-2667: stop codon Eevee-Akt-116 (3548 NES)
    nt 1-453: AH domain of Akt protein
    nt 454-462: linker (Glu-Phe-Gly)
    nt 463-1176: Aequorea YFP (YPet)
    nt 1177-1182: linker (Leu-Glu)
    nt 1183-1605: FHA1 domain of yeast Rad53 gene
    nt 1606-1611: linker (Gly-Thr)
    nt 1612-1959: EV116 linker
    nt 1864-1965: linker (Ser-Gly)
    nt 1870-1998: PKA substrate sequence
    nt 1903-2007: linker (Gly-Gly-Arg)
    nt 1912-2718: Aequorea CFP (ECFP)
    nt 2623-2724: linker (Ser-Arg)
    nt 2629-2760: nuclear export signal (NES)
    nt 2665-2763: stop codon (2) Expression of EV Linker Containing-Unimolecular FRET Biosensors (EeVee-Akts) in Mammalian Cell and Time-Lapse Fluorescence Microscopy Analysis An analysis was performed in the same manner as in Example 1-(2), except that COS7 cells were used. As shown in FIG. 10, a 116 a.a. EV linker significantly reduces the basal state.

Example 3

Measurement of ERK Enzyme Activity with Eevee-ERK (1) Construction of Gene Encoding EV Linker Containing-Unimolecular FRET Biosensor Eevee-ERK (3550 NES) for Measurement of ERK Enzyme Activity (i) There was produced a sequence in which a substrate sequence and a phosphorylated peptide recognition sequence in the Eevee-PKA-116 were replaced by an ERK substrate sequence by means of a PCR method using synthetic primers. The resultant plasmid was designated as "Eevee-ERK". There will be described a nucleotide sequence (SEQ ID NO: 31) of the Eevee-ERK, and a predicted amino acid sequence thereof (SEQ ID NO: 32).
    nt 1-714: Aequorea YFP (YPet)
    nt 715-720: linker (Leu-Glu)
    nt 721-882: WW domain of Pin1 gene
    nt 1144-888: linker (Gly-Thr)
    nt 1150-1236: EV116 linker
    nt 1498-1242: linker (Ser-Gly)
    nt 1504-1272: ERK substrate sequence
    nt 1528-1281: linker (Gly-Gly-Arg)
    nt 1537-1992: Aequorea CFP (ECFP)
    nt 2248-2004: linker (Gly-Arg-Ser-Arg)
    nt 2254-2040: nuclear export signal (NES)
    nt 2290-2043: stop codon (ii) There was also constructed a vector in which a docking sequence unique to the ERK substrate was added, which was designated as "Eevee-ERK-DS (3560 NES)". There will be described a nucleotide sequence (SEQ ID NO: 33) of the Eevee-ERK-DS (3560 NES), and a predicted amino acid sequence thereof (SEQ ID NO: 34).
    nt 1-714: Aequorea YFP (YPet)
    nt 715-720: linker (Leu-Glu)

nt 721-882: WW domain of Pin1 gene
nt 883-888: linker (Gly-Thr)
nt 889-1236: EV116 linker
nt 1237-1242: linker (Ser-Gly)
nt 1243-1272: ERK substrate sequence
nt 1273-1284: linker (Ala-Lys-Leu-Ser)
nt 1285-1296: docking sequence (Phe-Gln-Phe-Pro)
nt 1297-1305: linker (Gly-Gly-Arg)
nt 1306-2016: Aequorea CFP (ECFP)
nt 2017-2028: linker (Gly-Arg-Ser-Arg)
nt 2029-2064: nuclear export signal (NES)
nt 2065-2067: stop codon (2) Expression of EV Linker Containing-Unimolecular FRET Biosensor (EeVee-ERK) in Mammalian Cell and Time-Lapse Fluorescence Microscopy Analysis An analysis was performed in the same manner as in Example 1-(2). That is, the Eevee-ERK was expressed in HeLa cells and stimulated with EGF. As shown in FIGS. 11A, 11B, 11C and 11D, the EV linker containing-biosensor (3560 NES) had more increased gain than that of a Gly linker containing-biosensor (EKAR-1667 nes), which is partially caused by low FRET at the basal state.

Example 4

Measurement of Tyrosine Kinase Enzyme Activity with EV Linker Containing-Unimolecular FRET Biosensor Picchu-734

Figure 12:
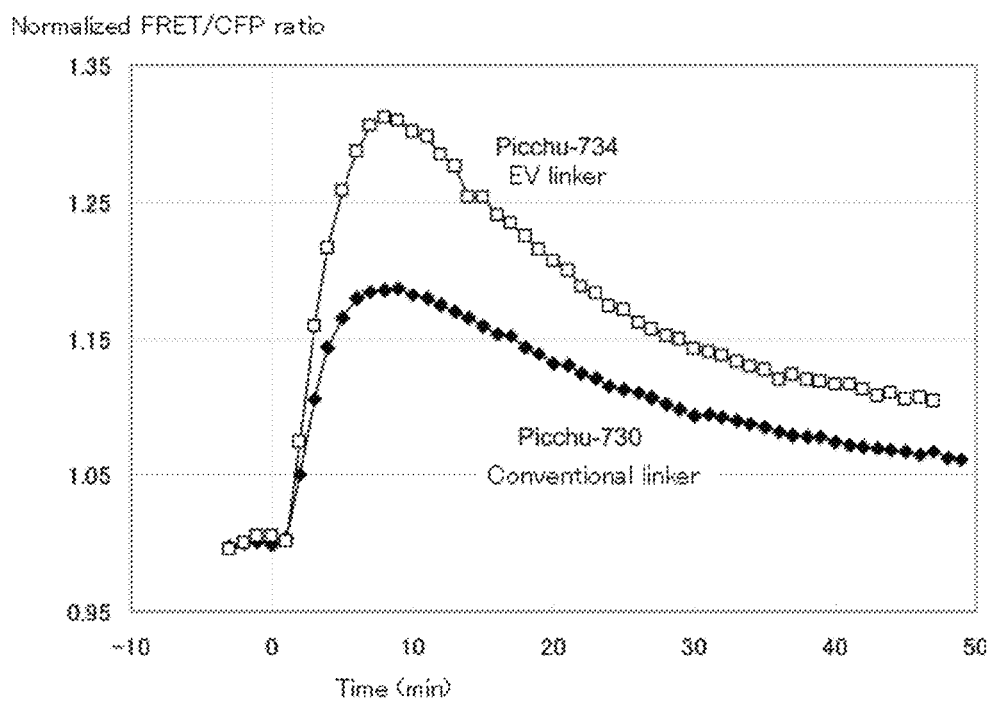
FIG. 12 illustrates a reactivity of Picchu-734 which is a biosensor of EGFR/Abl containing the EV linker. The Picch-734 was expressed in HeLa cells and stimulated with 10 ng/mL EGF. Picchu-734 is found to have a higher gain than Picchu-730 containing no EV linker.

(1) Construction of EV Linker Containing-Unimolecular FRET Biosensor Picchu-734 for Measurement of Tyrosine Kinase Enzyme Activity (i) A region containing a SH2 domain of CrkII protein was amplified by PCR, and inserted into a cleavage product of Eevee-PKA-116 (3536 NES) with XhoI/Asp718I. A substrate sequence site in the resultant product was replaced, resulting in a gene of Picchu-734. There will be described a nucleotide sequence (SEQ ID NO: 35) of the Picchu-734, and a predicted amino acid sequence thereof (SEQ ID NO: 36).

nt 1-714: Aequorea YFP (YPet)
nt 715-720: linker (Leu-Glu)
nt 721-1332: SH2 domain of CRKII gene
nt 883-1338: linker (Gly-Thr)
nt 889-1686: EV116linker
nt 1237-1692: linker (Ser-Gly)
nt 1243-1719: tyrosine-phosphorylated substrate sequence of CRKII
nt 1273-1728: linker (Ala-Lys-Leu-Ser)
nt 1306-2439: Aequorea CFP (ECFP)
nt 2017-2451: linker (Gly-Arg-Ser-Arg)
nt 2029-2487: nuclear export signal (NES)
nt 2065-2490: stop codon (2) Expression of EV Linker Containing-Unimolecular FRET Biosensor Picchu-734 and Time-Lapse Fluorescence Microscopy Analysis for Measurement of Tyrosine Kinase Activity in Mammalian Cell An analysis was performed in the same manner as in Example 3-(2). As can be seen from FIG. 12, the EV linker containing-Picchu biosensor (Picchu-734) had more increased gain than that of the non-EV linker containing-biosensor (Picchu-730) [Kurokawa, K., N. Mochizuki, Y. Ohba, H. Mizuno, A. Miyawaki, and M. Matsuda. 2001. A pair of FRET-based probes for tyrosine phosphorylation of the CrkII adaptor protein in vivo. J. Biol. Chem. 276:31305-31310.].

Example 5

Measurement of Rac1 Activity with Raichu-Rac1

Figure 13A:
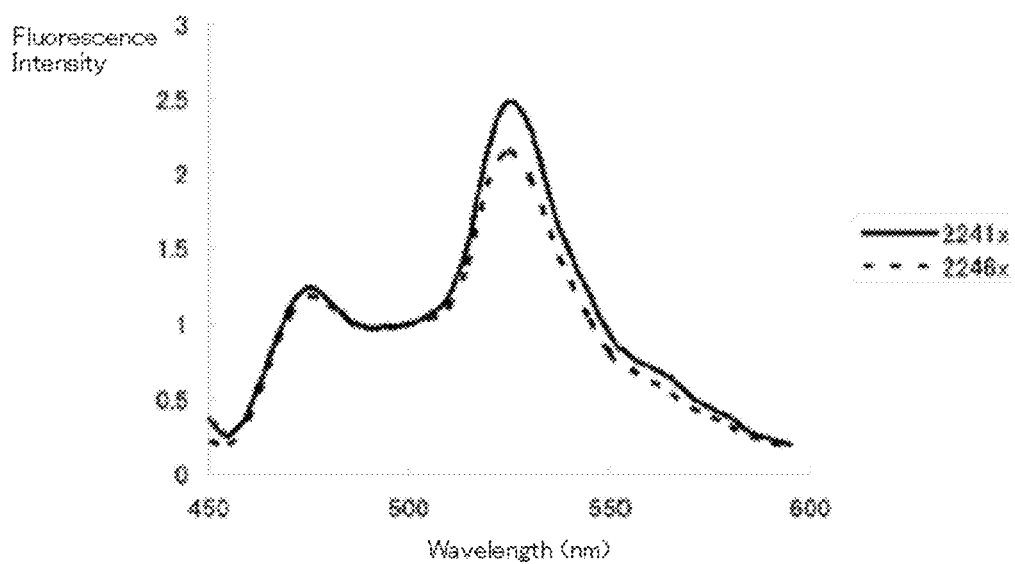
FIG. 13A illustrates measurement results of Rac1 activities with Raichu-Rac1 (2246X) containing the EV linker. HeLa cells were transfected with pRaichu-Rac1 (2241X) containing no EV linker and pRaichu-Rac1 (2246X) containing the EV linker. After 48 hours, the cells imaged according to the method described in Example 2. Fluorescence intensities at various wavelengths were measured by the confocal laser scanning microscope FV-1000 upon excitation at 438 nm. It has been found that as the EV linkers become longer, then fluorescence intensities at 530 nm, which indicate FRET at the basal state, are significantly reduced.
Figure 13B:
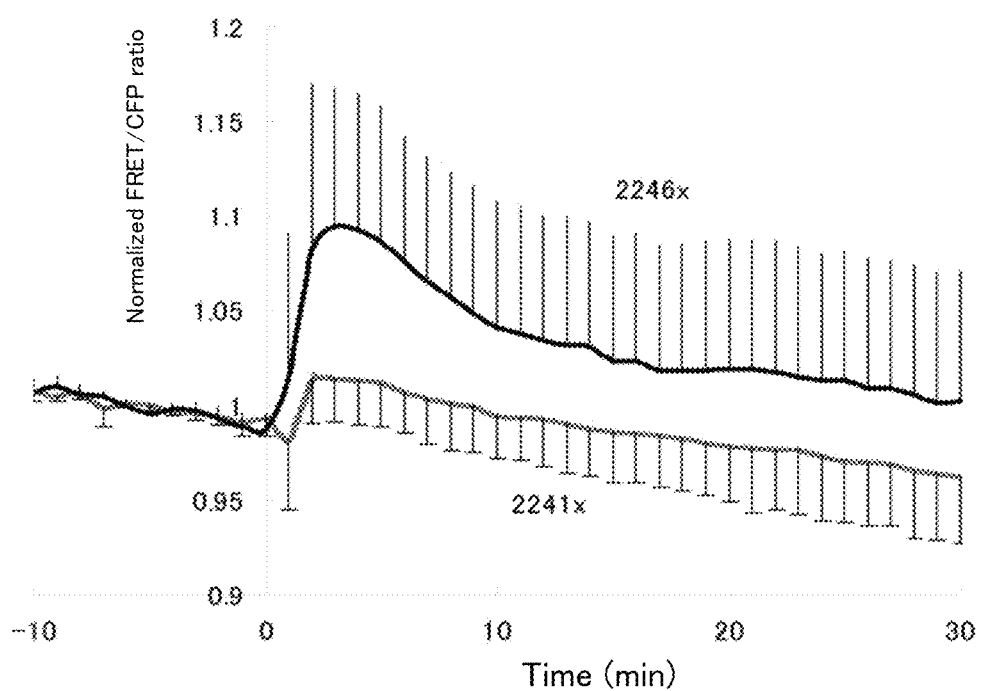
FIG. 13B illustrates a graph of normalized FRET/CFP when, in the imaging in FIG. 13A, epidermal growth factor (EGF) was added to a concentration of 25 ng/mL at 10 min after the onset of the imaging, and then the imaging proceeded. It has been found that Raichu-Rac1 (2246X) containing the EV linker has higher activities.
Figure 14A:
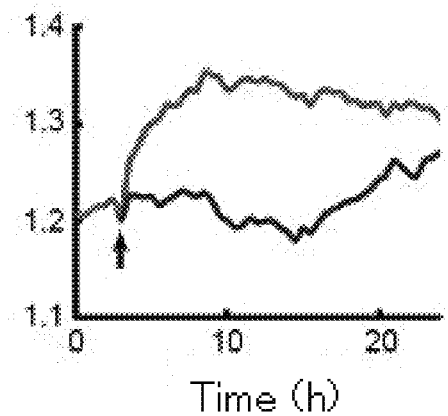
FIG. 14A illustrates measured data of FRET/CFP efficiency (described as Rac1 activity) when rat C6 cells stably expressing Raichu-2246X were time lapse-imaged for 24 hours. An arrow denotes a cell division. This figure suggests that FRET can be stably measured for a long time in EV linker expressing cells.
Figure 14B:
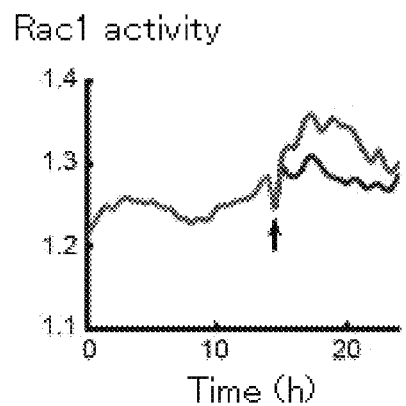
FIG. 14B illustrates results of another cell imaged under the same conditions as described above.
Figure 14C:
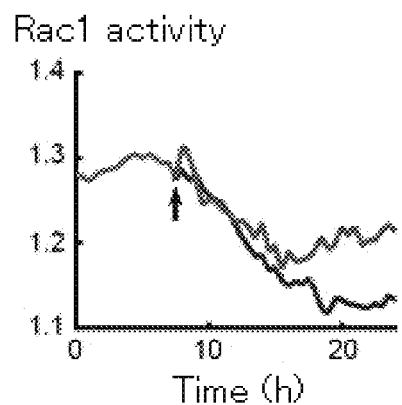
FIG. 14C illustrates results of another cell imaged under the same conditions as described above.
Figure 14D:
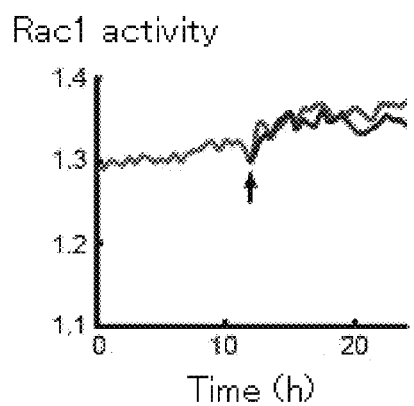
FIG. 14D illustrates results of another cell imaged under the same conditions as described above.

(1) Construction of EV linker Containing-Unimolecular FRET Biosensor Raichu-Rac1 (2246X) for Measurement of Rac1 Activity (i) A unimolecular FRET biosensor Raichu-Rac1 (2241X) for measuring Rac1 activity was constructed by means of, for example, a PCR based on a known Raichu-Rac1 (1011X) (see Itoh, R. E., K. Kurokawa, Y. Ohba, H. Yoshizaki, N. Mochizuki, and M. Matsuda. 2002. Activation of Rac and Cdc42 video-imaged by FRET-based single-molecule probes in the membrane of living cells. Mol. Cell. Biol. 22:6582-6591). There will be described a nucleotide sequence (SEQ ID NO: 37) of the Raichu-Rac1 (2241X), and a predicted amino acid sequence thereof (SEQ ID NO: 38).

nt 1-714: Aequorea YFP (YPet)
nt 715-720: linker (Leu-Glu)
nt 721-969: CRIB domain of Pak protein
nt 883-996: glycine linker
nt 1237-1527: Rac1
nt 1273-1536: linker (Arg-Gly-Arg)
nt 1306-2247: Aequorea CFP (Turquoise)
nt 1273-2253: linker (Ser-Arg)
nt 2017-2313: C-terminal domain of KRas protein
nt 2065-2316: stop codon (ii) An EV linker containing-mmolecular FRET biosensor Raichu-Rac1 (2246X) for measuring Rac1 activity was constructed based on the Raichu-Rac1 (2241X) by exchanging a linker. There will be described a nucleotide sequence (SEQ ID NO: 39) of the Raichu-Rac1 (2246X), and a predicted amino acid sequence thereof (SEQ ID NO: 40).

nt 1-714: Aequorea YFP (YPet)
nt 715-720: linker (Leu-Glu)
nt 721-969: CRIB domain of Pak protein
nt 970-1332: EV116 linker
nt 1333-1860: Rac1
nt 1861-1869: linker (Arg-Gly-Arg)
nt 1870-2580: Aequorea CFP (Turquoise)
nt 2581-2586: linker (Ser-Arg)
nt 2587-2646: C-terminal domain of KRas protein
nt 2647-2649: stop codon (2) Expression of EV Linker Containing-Unimolecular FRET Biosensor Raichu-Rac1 and Time-Lapse Fluorescence Microscopy Analysis for Measurement of Rac1 Activity in Mammalian Cell An analysis was performed in the same manner as in Example 3-(2). As can be seen from FIGS. 13A and 13B, the EV linker containing-Raichu biosensor (Raichu-2246X) had lower FRET at the basal state and significantly increased FRET in the presence of EGF-stimulation, i.e., had significantly higher sensitivity than the Raichu biosensor containing a conventional linker (Raichu-2241X).

(3) Establishment of Cell Line Stably Expressing Raichu-Rac1 (2246X)

The gene of Raichu-Rac1 (2246X) was inserted into pPB plasmid. This plasmid and a transposase expression vector (pCMV-mPBase) [Yusa, K., R. Rad, J. Takeda, and A. Bradley. 2009. Generation of transgene-free induced pluripotent mouse stem cells by the piggyBac transposon. Nat. Methods 6:363-369.] were co-transfected into C6 cells. Two days after the co-transfection, blasticidine was added thereto to a concentration of 10 ng/mL and cultured for additional 2 weeks. Thereafter, cloning was performed in a 96-well culture plate. As a result, a cultured cell line stably expressing the biosensor was successfully established. This cell line enabled Rac1 activity to be monitored for a long period (see FIGS. 14A, 14B, 14C and 14D).

Example 6

Measurement of Cdc42 Activity with Raichu-Cdc42 (2253X)

Figure 15A:
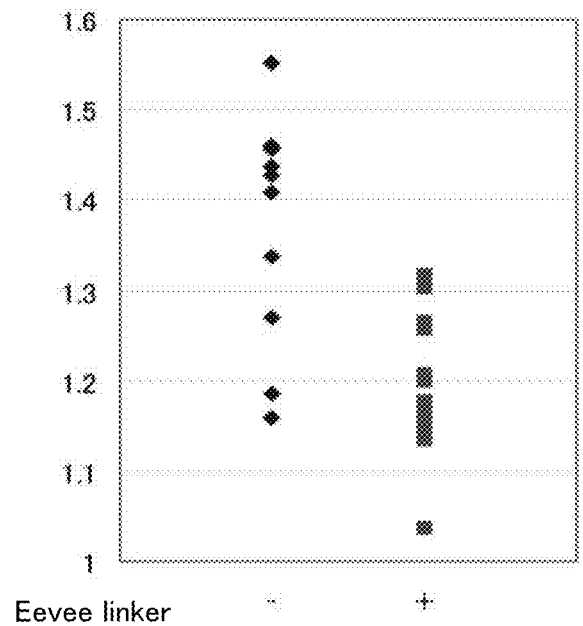
FIG. 15A illustrates FRET efficiencies at the basal state in CO7 cells expressing Raichu-Cdc42 containing the EV linker. It is found that the EV linker significantly reduces the FRET efficiency at the basal state.
Figure 15B:
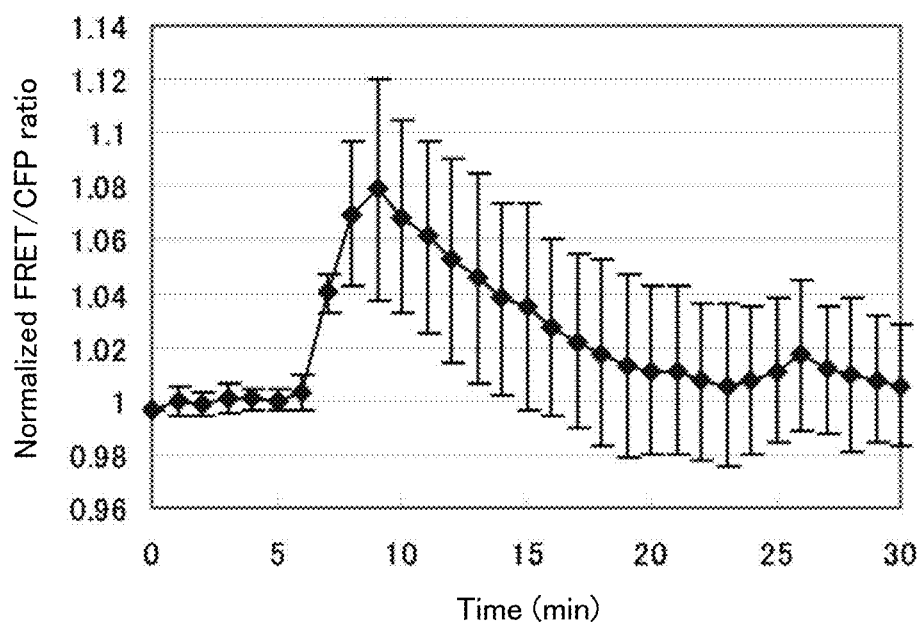
FIG. 15B illustrates a graph of normalized FRET/CFP for the Raichu-Cdc42 containing the EV linker when epidermal growth factor (EGF) was added to a concentration of 25 ng/mL at 10 min after the onset of the imaging, and then the imaging proceeded.
Figure 15C:
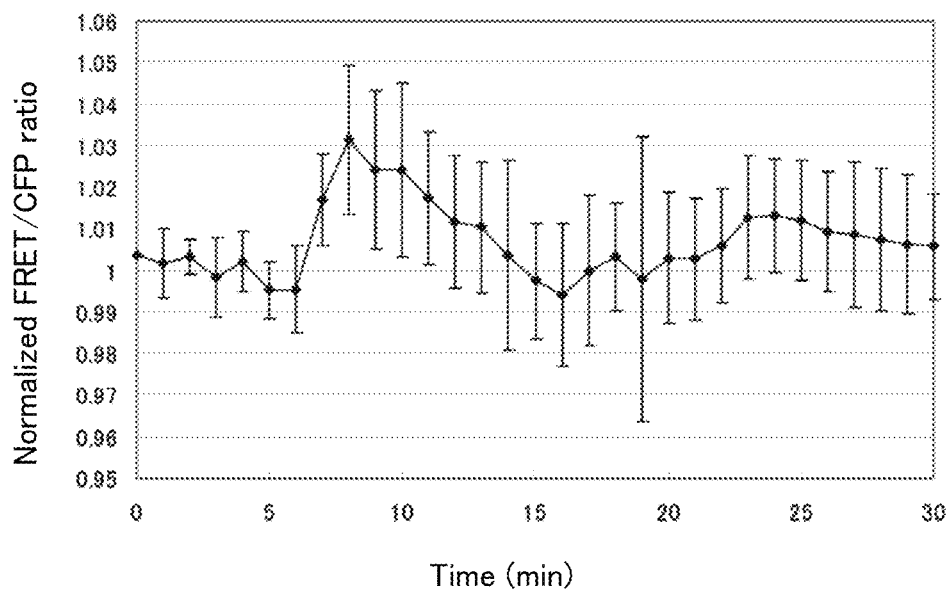
FIG. 15C illustrates a graph of normalized FRET/CFP for the Raichu-Cdc42 containing no EV linker as the same manner as in FIG. 15B. It is found that Raichu-Cdc42 containing the EV linker has higher reactivity than the Raichu-Cdc42 containing no EV linker.

(1) Construction of EV Linker Containing-Unimolecular FRET Biosensor Raichu-Cdc42 (2253X) for Measurement of Cdc42 Activity (i) A unimolecular FRET biosensor Raichu-Cdc42 (2253X) for measuring Cdc42 activity was constructed by means of, for example, PCR based on a known Raichu-Cdc42 (1054X). There will be described a nucleotide sequence (SEQ ID NO: 41) of the Raichu-Cdc42 (2253X), and a predicted amino acid sequence thereof (SEQ ID NO: 42).

nt 1-714: Aequorea YFP (YPet)
nt 715-720: linker (Leu-Glu)
nt 721-969: CRIB domain of Pak protein
nt 970-1332: EV116 linker
nt 1333-1857: Cdc42
nt 1858-1866: linker (Arg-Gly-Arg)
nt 1867-2577: Aequorea CFP (Turquoise)
nt 2578-2583: linker (Ser-Arg)
nt 2584-2643: C-terminal domain of KRas protein
nt 2644-2646: stop codon (2) Expression of EV Linker Containing-Unimolecular FRET Biosensor Raichu-Cdc42 and Time-Lapse Fluorescence Microscopy Analysis for Measurement of Cdc42 Activity in Mammalian Cell An analysis was performed in the same manner as in Example 3-(2). As can be seen from FIGS. 15A to 15C, this biosensor had also low FRET at the basal state. Therefore, an EGF-stimulus dependent activation of Cdc42, which had been hard to be detected, was enabled to be high-sensitively detected.

Example 8

Measurement of HRas Activity with Raichu-HRas (3705X)

Figure 16A:
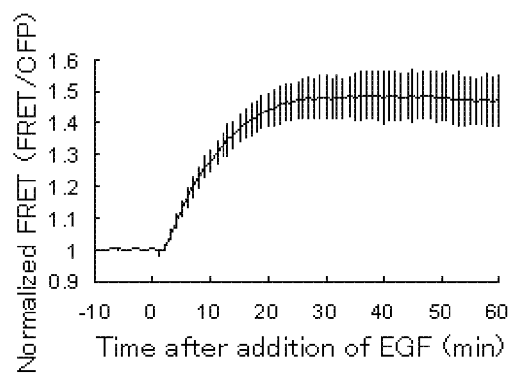
FIG. 16A illustrates a time-lapse image acquired every 1 min when HeLa cells expressing Raichu-Ras (3705X) containing the EV linker were stimulated with 10 ng/mL EGF. It has been found that Raichu-HRas containing the EV linker can detect more rapidly and sensitively activations compared with Raichu-HRas containing no EV linker (FIG. 16B).
Figure 16B:
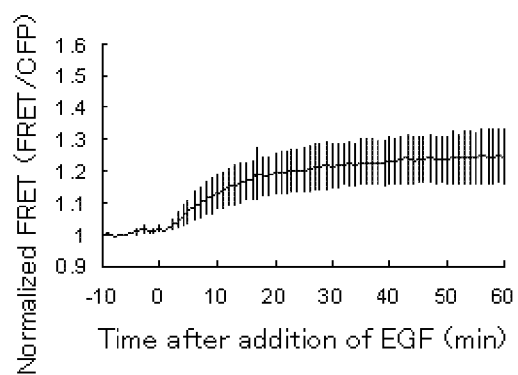
FIG. 16B illustrates a time-lapse image acquired in the same manner as in FIG. 16A for Raichu-HRas containing no EV linker.

(1) Construction of EV linker Containing-Unimolecular FRET Biosensor Raichu-HRas (3705X) for Measurement of HRas Activity (i) A unimolecular FRET biosensor Raichu-HRas (3705X) for measuring HRas activity was constructed by means of, for example, PCR based on a known Raichu-HRas [Mochizuki, N., S. Yamashita, K. Kurokawa, Y. Ohba, T. Nagai, A. Miyawaki, and M. Matsuda. 2001. Spacio-temporal images of growth factor-induced activation of Ras and Rap1. Nature 411:1065-1068.]. There will be described a nucleotide sequence (SEQ ID NO: 43) of the Raichu-HRas (3705X), and a predicted amino acid sequence thereof (SEQ ID NO: 44).

nt 1-714: Aequorea YFP (YPet)
nt 715-720: linker (Leu-Glu)
nt 721-1236: HRas protein
nt 1237-1602: EV116 linker
nt 1603-1845: PBD domain of Raf protein
nt 1846-1854: linker (Gly-Gly-Arg)
nt 1855-2565: Aequorea CFP (Turquoise)
nt 2566-2571: linker (Ser-Arg)
nt 2584-2631: C-terminal domain of KRas protein
nt 2632-2634: stop codon (2) Expression of EV Linker Containing-Unimolecular FRET Biosensor Raichu-HRas and Time-Lapse Fluorescence Microscopy Analysis for Measurement of HRas Activity in Mammalian Cell An analysis was performed in the same manner as in Example 3-(2). Thus obtained time-lapse FRET imaging data are shown in FIGS. 16A and 16B. It has been found that the Raichu-HRas could detect activation more rapidly and sensitively than a prototype HRas [Mochizuki, N., S. Yamashita, K. Kurokawa, Y. Ohba, T. Nagai, A. Miyawaki, and M. Matsuda. 2001. Spacio-temporal images of growth factor-induced activation of Ras and Rap1. Nature 411:1065-1068.].

Example 10

Generation of Transgenic Mouse Expressing Eevee-ERK (3560 NES) and Eevee-PKA (3536 NES)

(1) Microinjection of Gene Encoding EV Linker Containing-Unimolecular FRET biosensor Eevee-ERK (3560 NES) and Eevee-PKA (3536 NES) into Fertilized Egg for Measurement of ERK and PKA Enzyme Activities A mammalian cell expression plasmid containing a gene of Eevee-PKA (3536 NES) described in Example 1 or Eevee-ERK (3560 NES) described in Example 3 was inserted into a plasmid pT2A having a transposon recognition sequence. This plasmid and To12 transposon were microinjected as previously reported [Sumiyama, K., K. Kawakami, and K. Yagita. 2010. A simple and highly efficient transgenesis method in mice with the To12 transposon system and cytoplasmic microinjection. Genomics 95:306-311.]

(2) Screening of Transgenic Mouse Expressing Biosensor

Figure 17:
FIG. 17 illustrates a FRET image of a sagittal section in a transgenic mouse fetus expressing Eevee-ERK acquired by a fluorescence microscope. Values which are higher and lower by 40% than the basal FRET are shown in pseudo colors (the warmer color denotes higher FRET). An activity distribution in an individual can be visualized.
Figure 18A:
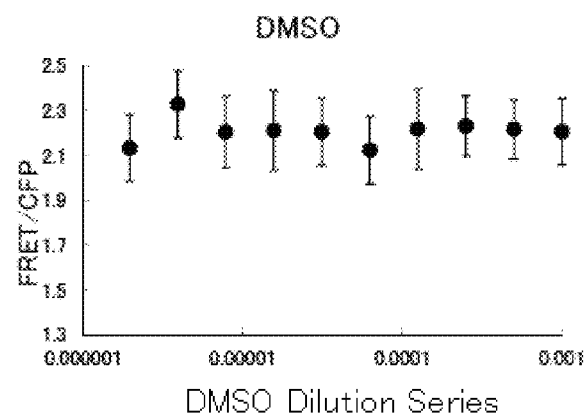
FIG. 18A illustrates results when HeLa cells stably expressing Eevee-ERK were seeded onto a 96-well plate, were added thereto serial-diluted inhibitors and stimulated with 25 ng/mL EGF. ERK activities were automatically measured for 30 or more cells, averaged, and plotted.
Figure 18B:
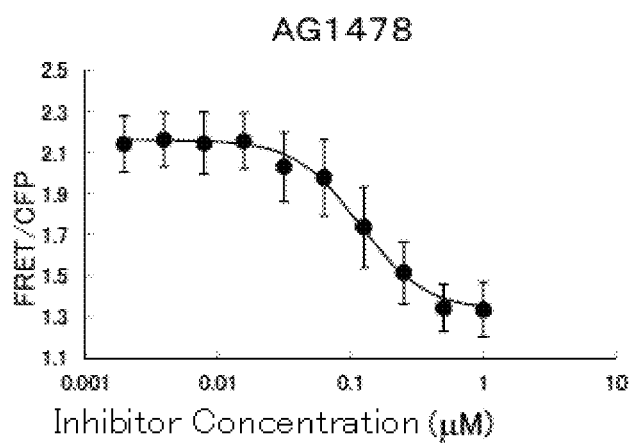
FIG. 18B illustrates results when, as the inhibitors, EGF receptor inhibitors (AG1478) were used.
Figure 18C:
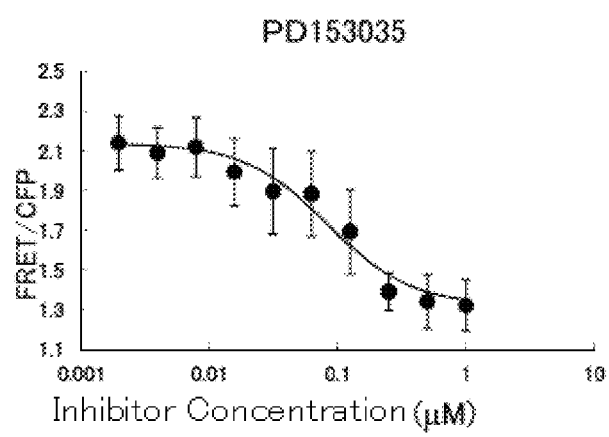
FIG. 18C illustrates results when, as the inhibitors, MEK inhibitors (PD15035) were used.
Figure 18D:
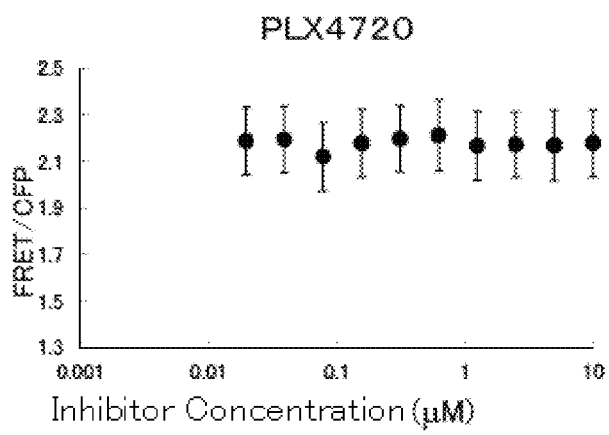
FIG. 18D illustrates results when, as the inhibitors, BRAF inhibitors (PLX4720) were used.
Figure 18E:
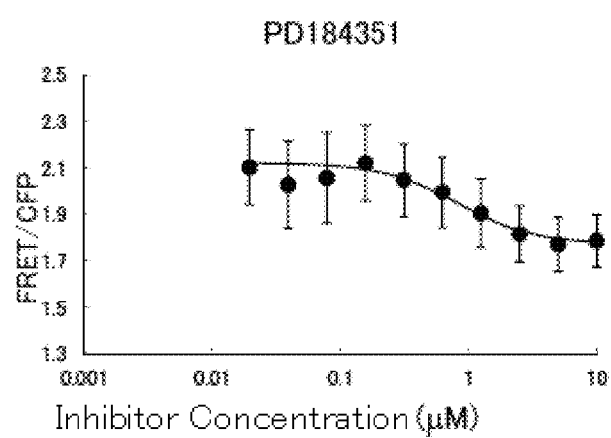
FIG. 18E illustrates results when, as the inhibitors, MEK inhibitors (PD184351) were used.
Figure 18F:
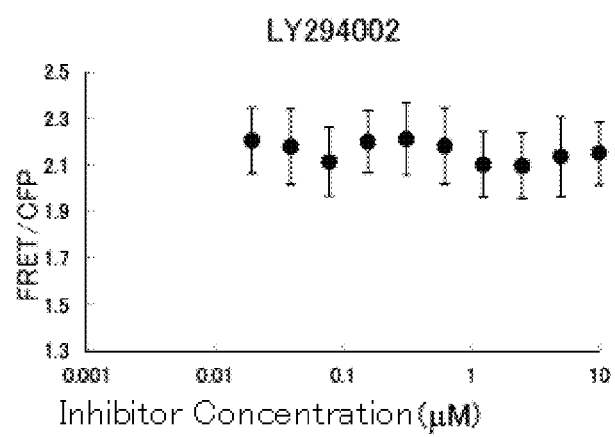
FIG. 18F illustrates results when, as the inhibitors, phosphatidylinositol 3-phosphate kinase inhibitors (LY294002) were used.
Figure 18G:
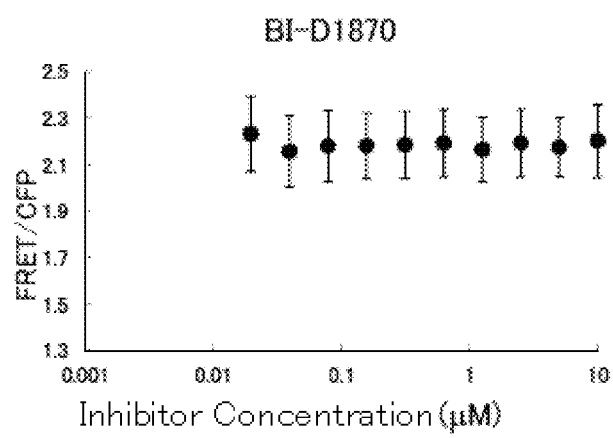
FIG. 18G illustrates results when, as the inhibitors, RSK inhibitors (BI-D1870) were used.
Figure 18H:
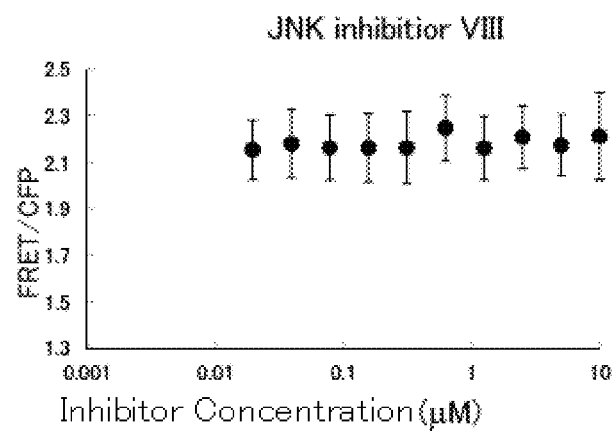
FIG. 18H illustrates results when, as the inhibitors, JNK inhibitors (JNK inhibitor VIII) were used. It has been found that EGF dependent-ERK activation is effectively inhibited by the EGF receptor inhibitors and the MEK inhibitors in HeLa cells.

The resultant mouse was irradiated with LED at 420 nm and imaged by a color digital camera with 470 nm short wavelength cut filter to thereby confirm the presence or absence of green fluorescence. Thus, transgenic mice could be easily identified. Also, a FRET image of a sagittal section in the transgenic mouse fetus was acquired by the fluorescence microscope described in Example 1. Based on the image, a spatial distribution of ERK or PKA activity could be examined (see FIG. 17).

Example 11

Drug Sensitivity Test with Cell Line Expressing Eevee-ERK (3560 NES)

(1) Establishment of Cell Line Stably Expressing Gene Encoding EV linker containing-unimolecular FRET biosensor Eevee-ERK (3560 NES) for Measurement of ERK Enzyme Activity A mammalian cell expression plasmid containing the gene of Eevee-ERK (3560 NES) described in Example 3 was inserted into a plasmid having a transposon recognition sequence. This plasmid and a transposon expression vector was co-transfected as previously reported and screened for biosensor-expressing cell lines by blasticidin [Yusa, K., R. Rad, J. Takeda, and A. Bradley. 2009. Generation of transgene-free induced pluripotent mouse stem cells by the piggyBac transposon. Nat. Methods 6 (5)363-369].

(2) FRET measurement in Cell Line Stably Expressing Biosensor

Cultured cell lines were seeded onto a 96-well culture plate. Serial-diluted inhibitors were added thereto. The cell lines were stimulated with 25 ng/mL EGF. After 30 min, ERK activities were measured as described in Example 3 (see FIGS. 18A to 18H). The average ERK activities of 30 or more cells were plotted. The following inhibitors were used: EGF receptor inhibitors (AG1478), MEK inhibitors (PD15035, PD184351), BRAF inhibitors (PLX4720), phosphatidylinositol 3-phosphate kinase inhibitors (LY294002), RSK inhibitors (BI-D1870) and JNK inhibitors (JNK inhibitor VIII). The results indicate that the EGF dependent-activation of ERK is effectively inhibited by EGF receptors (AG1478) and MEK inhibitors (PD153035, PD184352) for HeLa cells. It could be very easily measured in living cells that the EGF dependent-activation of ERK were concentration-dependently inhibited by the above inhibitors.

Example 12

Drug Sensitivity Test with Transgenic Mouse Expressing Eevee-PKA (3536 NES)

(1) Imaging of Small Intestine in Transgenic Mouse Expressing Eevee-PKA (3536 NES)

The transgenic mouse expressing Eevee-PKA (3536 NES) generated in Example 10 was anesthetized with isoflurane. A small intestine of the mouse was time-lapse imaged by an inverted two-photon microscope IX81/FV1000 (product of Olympus Corporation). Cells were excited at 840 nm with a titanium-sapphire laser system (Mai Tai Deep See HP; product of Spectra-Physics, Inc.). CFP fluorescence and YFP fluorescence were acquired using BA 460-500 fluorescence filter (product of Olympus Corporation) and BA 520-560 fluorescence filter (product of Olympus Corporation), respectively. FRET images were obtained in the same manner as in Example 3.

(2) Visualization of Drug Effect in Living Mouse

Figure 19:
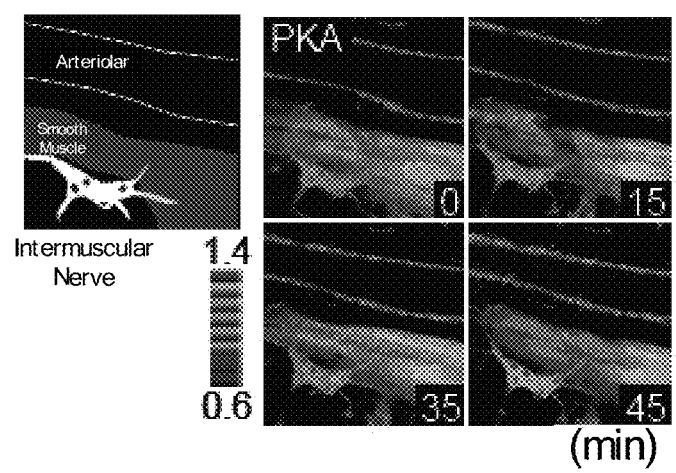
FIG. 19 illustrates results when the transgenic mouse expressing Eevee-PKA (3536 NES) was intravenously injected with theophylline, which is a phosphodiesterase inhibitor, and actosin, which is a cyclic adenosine triphosphate analog, and measured for PKA activities. Changes in PKA activities can be real-time visualized in an intermuscular nerve cell, an intestinal smooth muscle and a vascular smooth muscle.
Figure 20:
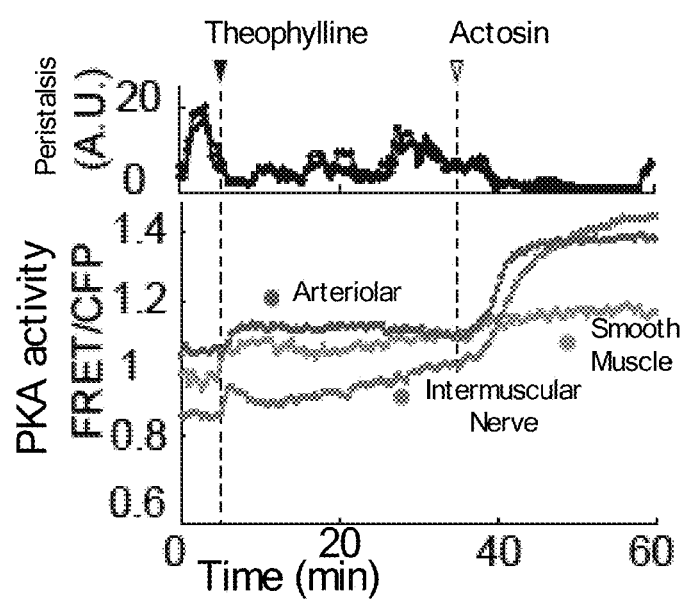
FIG. 20 illustrates a graph of images of FIG. 19.

The transgenic mouse was intravenously injected with theophylline, which is a phosphodiesterase inhibitor, and actosin, which is a cyclic adenosine triphosphate analog, and measured for PKA activities. As shown in FIGS. 19 and 20, changes in PKA activities can be real-time visualized in an intermuscular nerve cell, an intestinal smooth muscle and a vascular smooth muscle.

Example 13

There is high possibility that long linkers are susceptible to degradation by proteases. Therefore, linkers EV3x8 and EV6x4, which have increased number of alanines which easily form α-helix and decreased number of glycines, were constructed and determined for the gain.

(1) (i) Construction of Eevee-PKA-3x8 (3676 NES)

In the same manner as in Example (1) (iii), the pEevee-PKA-20, which was a mammalian cell expression vector of the Eevee-PKA-20, was cleaved with restriction enzymes Asp718I and Aor13HI. The resultant larger cleavage product was used to prepare a vector. DNA in which restriction enzyme cleavage sites of Asp718I and Aor13HI were added at each termini of DNA encoding an EV3x8 linker (SEQ ID NO: 45) was synthesized. The above DNA cleaved with Asp718I/Aor13HI and the resultant cleavage product was used as an insert. The insert was ligated with the vector, resulting in a pEevee-PKA-3x8. There will be described a nucleotide sequence (SEQ ID NO: 47) of the pEevee-PKA-3x8 and a predicted amino acid sequence thereof (SEQ ID NO: 48).

nt 1-714: Aequorea YFP (YPet)
nt 715-720: linker (Leu-Glu)
nt 721-1143: FHA1 domain of yeast Rad53 gene
nt 1144-1149: linker (Gly-Thr)
nt 1150-1551: EV3x8 linker (SEQ ID NO: 45)
nt 1552-1557: linker (Ser-Gly)
nt 1558-1581: PKA substrate sequence
nt 1582-1590: linker (Gly-Gly-Arg)
nt 1591-2307: Aequorea ECFP
nt 2308-2313: linker (Ser-Arg)
nt 2314-2349: nuclear export signal (NES)
nt 2350-2352: stop codon (1) (ii) Construction of Eevee-PKA-6x4 (3677 NES)

Figure 21:
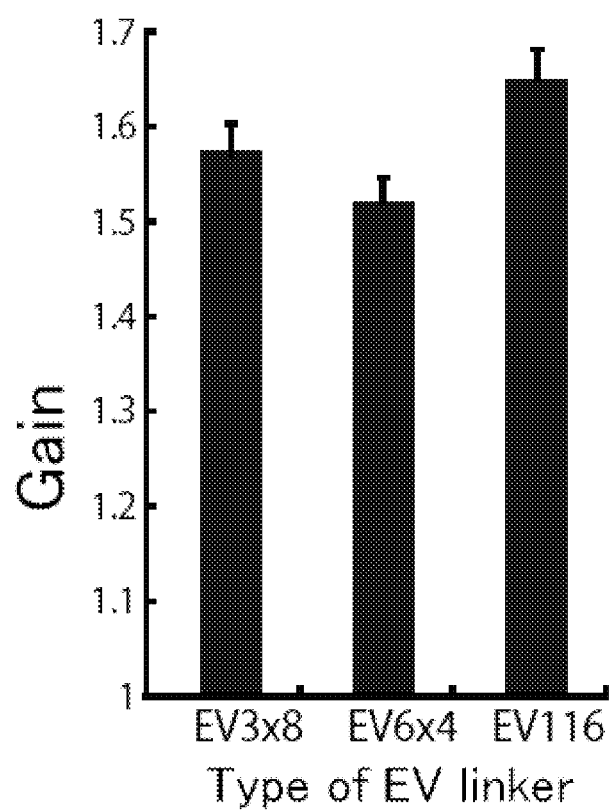
FIG. 21 demonstrates that biosensors containing EV3x8 or EV6x4 linker having low content of glycine have a comparable effect to biosensors containing EV116 linker. Fluorescence intensities at various wavelengths were measured for HeLa cells expressing Eevee-PKA-3x8, Eevee-PKA-4x6 or Eevee-PKA-116 by the confocal laser scanning microscope FV-1000 upon excitation at 438 nm in the same manner as in FIG. 7A. It has been found that the EV3x8 linker and the EV4x6 linker have a comparable effect to the EV116 linker.

The pEevee-PKA-20, which was a mammalian cell expression vector of the Eevee-PKA-20, was cleaved with restriction enzymes Asp718I and Aor13HI. The resultant larger cleavage product was used to prepare a vector. DNA in which restriction enzyme cleavage sites of Asp718I and Aor13HI were added at each termini of DNA encoding EV6x4 linker (SEQ ID NO: 46) was synthesized. The DNA cleaved with Asp718I/Aor13HI and the resultant cleavage product was used as an insert. The insert was ligated with the vector, resulting in a pEevee-PKA-6x4. There will be described a nucleotide sequence (SEQ ID NO: 49) of the pEevee-PKA-6x4 and a predicted amino acid sequence thereof (SEQ ID NO: 50).

nt 1-714: Aequorea YFP (YPet)
nt 715-720: linker (Leu-Glu)
nt 721-1143: FHA1 domain of yeast Rad53 gene
nt 1144-1149: linker (Gly-Thr)
nt 1150-1521: EV6x4linker (SEQ ID NO: 46)
nt 1522-1527: linker (Ser-Gly)
nt 1528-1551: PKA substrate sequence
nt 1552-1560: linker (Gly-Gly-Arg)
nt 1561-2277: Aequorea ECFP
nt 2278-2283: linker (Ser-Arg)
nt 2284-2319: nuclear export signal (NES)
nt 2320-2322: stop codon (2) The EV3x8 and the EC6x4 were determined for gains in the same manner as in Example 1, which revealed that both have comparable gains to the 116 a.a. linker (see FIG. 21).

INDUSTRIAL APPLICABILITY

The present invention provides an EV linker and a unimolecular FRET biosensor containing the EV linker which allow the serine-threonine kinase activity, the tyrosine kinase activity and the low molecular weight GTP-binding protein activity to be non-invasively measured; a gene encoding the EV linker or the biosensor; an expression vevtor containing the gene; a transformed cell and a transgenic non-human animal harboring the expression vector which is useful to express the biosensor and to non-invasively measure the serine-threonine kinase activity, the tyrosine kinase activity and the low molecular weight GTP-binding protein activity; a measurement method for measuring the serine-threonine kinase activity, the tyrosine kinase activity and the low molecular weight GTP-binding protein activity by means of the biosensor; and a method for screening a regulator of the serine-threonine kinase activity, the tyrosine kinase activity and the low molecular weight GTP-binding protein activity.

What is claimed is:

1. A linker for a unimolecular fluorescence resonance energy transfer (FRET) biosensor based on a principle of fluorescence resonance energy transfer, the linker comprising:
- a polypeptide comprising 84 to 244 amino acids residues,
- wherein the polypeptide consists of (i) glycine, (ii) alanine, and (iii) serine, threonine or both thereof,
- wherein 35% to 65% of a total number of the amino acid residues are glycine, 10% to 40% of the total number of the amino acid residues are alanine, and 10% to 40% of the total number the amino acid residues are serine, threonine or both thereof, and
- wherein the polypeptide has repeats of an amino acid sequence of SAGG, and wherein the number of the repeats of the amino acid sequence of SAGG is 19 to 54, and
- wherein the polypeptide is selected from a sequence consisting of SEQ ID NO: 15, SEQ ID NO: 18, SEQ ID NO: 23 and SEQ ID NO: 26.

2. A unimolecular fluorescence resonance energy transfer (FRET) biosensor based on a principle of fluorescence resonance energy transfer, the unimolecular FRET biosensor comprising:
- a fused protein, which comprises a sensor domain, a ligand domain, an acceptor fluorescent protein domain, a donor fluorescent protein domain, and a linker domain which links the sensor domain with the ligand domain,
- wherein the linker domain comprises a polypeptide comprising 84 to 244 amino acids residues,
- wherein the polypeptide consists of (i) glycine, (ii) alanine, and (iii) serine, threonine, or both thereof,
- wherein 35% to 65% of a total number of the amino acid residues are glycine, 10% to 40% of the total number of amino acid residues are alanine, and 10% to 40% of the total number of the amino acid residues are serine, threonine, or both thereof,
- wherein the polypeptide has repeats of an amino acid sequence of SAGG, and wherein the number of the repeats of the amino acid sequence of SAGG is 19 to 54, and
- wherein the polypeptide is selected from a sequence consisting of SEQ ID NO: 15, SEQ ID NO: 18, SEQ ID NO: 23 and SEQ ID NO: 26.

3. The unimolecular FRET biosensor according to claim 2, wherein the donor fluorescent protein is a yellow fluorescent protein for energy transfer (YPet).

* * * * *

SEQUENCE LISTING

<160> NUMBER OF SEQ ID NOS: 50

<210> SEQ ID NO 1
<211> LENGTH: 2208
<212> TYPE: DNA
<213> ORGANISM: Artificial Sequence
<220> FEATURE:
<223> OTHER INFORMATION: FRET biosensor for PKA

<400> SEQUENCE: 1

| | | | | | |
|---|---|---|---|---|---|
| atggtgagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagct | tctatgcacc | accggcaagc | tgcccgtgcc | ctggcccacc | 180 |
| ctcgtgacca | ccctgggcta | cggcctgcag | tgcttcgccc | gctaccccga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggagg | acggcaacat | cctggggcac | 420 |
| aagctggagt | acaactacaa | cagccacaac | gtctatatca | ccgccgacaa | gcagaagaac | 480 |
| ggcatcaagg | ccaacttcaa | gatccgccac | aacatcgagg | acggcggcgt | gcagctcgcc | 540 |
| gaccactacc | agcagaacac | ccccatcggc | gacggccccg | tgctgctgcc | cgacaaccac | 600 |
| tacctgagct | accagtccgc | cctgttcaaa | gaccccaacg | agaagcgcga | tcacatggtc | 660 |
| ctgctggagt | tcctgaccgc | cgccgggatc | actgagggca | tgaacgagct | gtacctcgag | 720 |
| aagtttctc | aagaacagat | cggcgaaaac | attgtgtgca | gggtcatttg | taccacgggt | 780 |
| caaattccca | tccgagattt | gtcagctgat | atttcacaag | tgcttaagga | aaaacgatcc | 840 |
| ataaagaaag | tttggacatt | tggtagaaac | ccagcctgtg | actatcattt | aggaaacatt | 900 |
| tcaagactgt | caaataagca | tttccaaata | ctactaggag | aagacggtaa | ccttttattg | 960 |
| aatgacattt | ccactaatgg | gacctggtta | aatgggcaaa | aagtcgagaa | gaacagcaat | 1020 |
| cagttactgt | cccaaggtga | tgaaataacc | gttggtgtag | gctggaatc | agatattta | 1080 |
| tctctggtca | ttttcataaa | cgacaaattt | aagcagtgcc | tggagcagaa | caaagttgat | 1140 |
| cgcggtaccg | gcttgtgtc | tagaggcgga | ggtggtggag | gaggtggagg | tggtggaggt | 1200 |
| ggaggtggag | gtggtggcgg | tggtggagga | ggaggagcta | gaggcggagg | tggtggagga | 1260 |
| ggtgaggtg | gtggaggtgg | aggtggaggt | ggtggcggtg | gtggaggagg | aggagctagc | 1320 |
| ggcggaggtg | gtggaggagg | tggaggtggt | ggaggtggag | gtggaggtgg | tggcggtggt | 1380 |
| ggaggaggag | gaatggctga | ccaactgtcc | ggattgaggc | gcgcgacgct | ggttgacggc | 1440 |
| ggccgcatgg | tgagcaaggg | cgaggagctg | ttcaccgggg | tggtgcccat | cctggtcgag | 1500 |
| ctggacggcg | acgtaaacgg | ccacaagttc | agcgtgtccg | gcgagggcga | gggcgatgcc | 1560 |
| acctacggca | agctgaccct | gaagttcatc | tgcaccaccg | gcaagctgcc | cgtgccctgg | 1620 |
| cccaccctcg | tgaccaccct | gacctggggc | gtgcagtgct | tcagccgcta | ccccgaccac | 1680 |
| atgaagcagc | acgacttctt | caagtccgcc | atgcccgaag | gctacgtcca | ggagcgcacc | 1740 |
| atcttcttca | aggacgacgg | caactacaag | acccgcgccg | aggtgaagtt | cgagggcgac | 1800 |
| accctggtga | accgcatcga | gctgaagggc | atcgacttca | aggaggacgg | caacatcctg | 1860 |
| gggcacaagc | tggagtacaa | ctacatcagc | cacaacgtct | atatcaccgc | cgacaagcag | 1920 |
| aagaacggca | tcaaggccaa | cttcaagatc | cgccacaaca | tcgaggacgg | cagcgtgcag | 1980 |
| ctcgccgacc | actaccagca | gaacaccccc | atcggcgacg | gccccgtgct | gctgcccgac | 2040 |

```
aaccactact tgagcaccca gtccgccctg agcaaagacc ccaacgagaa gcgcgatcac    2100
atggtcctgc tggagttcgt gaccgccgcc gggatcactc tcggcatgga cgagctgggc    2160
cgctctagac tgcagctgcc tcctctggaa cgcctgactc tggattaa                2208
```

<210> SEQ ID NO 2
<211> LENGTH: 735
<212> TYPE: PRT
<213> ORGANISM: Artificial Sequence
<220> FEATURE:
<223> OTHER INFORMATION: FRET biosensor of PKA

<400> SEQUENCE: 2

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Leu
        35                  40                  45

Cys Thr Thr Gly Lys Leu Pro Val Pro Trp Pro Thr Leu Val Thr Thr
50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Phe Lys Asp Pro Asn Glu Lys Arg Asp His Met Val Leu Leu Glu Phe
    210                 215                 220

Leu Thr Ala Ala Gly Ile Thr Glu Gly Met Asn Glu Leu Tyr Leu Glu
225                 230                 235                 240

Lys Phe Ser Gln Glu Gln Ile Gly Glu Asn Ile Val Cys Arg Val Ile
                245                 250                 255

Cys Thr Thr Gly Gln Ile Pro Ile Arg Asp Leu Ser Ala Asp Ile Ser
            260                 265                 270

Gln Val Leu Lys Glu Lys Arg Ser Ile Lys Lys Val Trp Thr Phe Gly
        275                 280                 285

Arg Asn Pro Ala Cys Asp Tyr His Leu Gly Asn Ile Ser Arg Leu Ser
    290                 295                 300

Asn Lys His Phe Gln Ile Leu Leu Gly Glu Asp Gly Asn Leu Leu Leu
305                 310                 315                 320

Asn Asp Ile Ser Thr Asn Gly Thr Trp Leu Asn Gly Gln Lys Val Glu
                325                 330                 335
```

```
Lys Asn Ser Asn Gln Leu Leu Ser Gln Gly Asp Glu Ile Thr Val Gly
                340                 345                 350

Val Gly Val Glu Ser Asp Ile Leu Ser Leu Val Ile Phe Ile Asn Asp
            355                 360                 365

Lys Phe Lys Gln Cys Leu Glu Gln Asn Lys Val Asp Arg Gly Thr Gly
370                 375                 380

Leu Val Ser Arg Gly Gly Gly Gly Gly Gly Gly Gly Gly Gly Gly Gly
385                 390                 395                 400

Gly Gly Gly Gly Gly Gly Gly Gly Gly Gly Ala Arg Gly Gly Gly Gly
                405                 410                 415

Gly Gly Gly Gly Gly Gly Gly Gly Gly Gly Gly Gly Gly Gly Gly Gly
            420                 425                 430

Gly Gly Gly Gly Gly Gly Ala Ser Gly Gly Gly Gly Gly Gly Gly Gly
        435                 440                 445

Gly Gly Gly Gly Gly Gly Gly Gly Gly Gly Gly Gly Gly Gly Gly Gly
450                 455                 460

Met Ala Asp Gln Leu Ser Gly Leu Arg Arg Ala Thr Leu Val Asp Gly
465                 470                 475                 480

Gly Arg Met Val Ser Lys Gly Glu Glu Leu Phe Thr Gly Val Val Pro
                485                 490                 495

Ile Leu Val Glu Leu Asp Gly Asp Val Asn Gly His Lys Phe Ser Val
            500                 505                 510

Ser Gly Glu Gly Glu Gly Asp Ala Thr Tyr Gly Lys Leu Thr Leu Lys
        515                 520                 525

Phe Ile Cys Thr Thr Gly Lys Leu Pro Val Pro Trp Pro Thr Leu Val
530                 535                 540

Thr Thr Leu Thr Trp Gly Val Gln Cys Phe Ser Arg Tyr Pro Asp His
545                 550                 555                 560

Met Lys Gln His Asp Phe Phe Lys Ser Ala Met Pro Glu Gly Tyr Val
                565                 570                 575

Gln Glu Arg Thr Ile Phe Phe Lys Asp Asp Gly Asn Tyr Lys Thr Arg
            580                 585                 590

Ala Glu Val Lys Phe Glu Gly Asp Thr Leu Val Asn Arg Ile Glu Leu
        595                 600                 605

Lys Gly Ile Asp Phe Lys Glu Asp Gly Asn Ile Leu Gly His Lys Leu
610                 615                 620

Glu Tyr Asn Tyr Ile Ser His Asn Val Tyr Ile Thr Ala Asp Lys Gln
625                 630                 635                 640

Lys Asn Gly Ile Lys Ala Asn Phe Lys Ile Arg His Asn Ile Glu Asp
                645                 650                 655

Gly Ser Val Gln Leu Ala Asp His Tyr Gln Gln Asn Thr Pro Ile Gly
            660                 665                 670

Asp Gly Pro Val Leu Leu Pro Asp Asn His Tyr Leu Ser Thr Gln Ser
        675                 680                 685

Ala Leu Ser Lys Asp Pro Asn Glu Lys Arg Asp His Met Val Leu Leu
690                 695                 700

Glu Phe Val Thr Ala Ala Gly Ile Thr Leu Gly Met Asp Glu Leu Gly
705                 710                 715                 720

Arg Ser Arg Leu Gln Leu Pro Pro Leu Glu Arg Leu Thr Leu Asp
                725                 730                 735

<210> SEQ ID NO 3
<211> LENGTH: 66
```

```
<212> TYPE: DNA
<213> ORGANISM: Artificial Sequence
<220> FEATURE:
<223> OTHER INFORMATION: A forward primer

<400> SEQUENCE: 3
gtaccagtgc tggtggtagt gctggtggta gtgctggtgg tagtgctggt ggtagtgctg    60
gtggtt                                                              66

<210> SEQ ID NO 4
<211> LENGTH: 66
<212> TYPE: DNA
<213> ORGANISM: Artificial Sequence
<220> FEATURE:
<223> OTHER INFORMATION: A reverse linker

<400> SEQUENCE: 4
ccggaaccac cagcactacc accagcacta ccaccagcac taccaccagc actaccacca    60
gcactg                                                              66

<210> SEQ ID NO 5
<211> LENGTH: 20
<212> TYPE: PRT
<213> ORGANISM: Artificial Sequence
<220> FEATURE:
<223> OTHER INFORMATION: A 20 amino acid linker

<400> SEQUENCE: 5

Ser Ala Gly Gly Ser Ala Gly Gly Ser Ala Gly Gly Ser Ala Gly Gly
1               5                   10                  15

Ser Ala Gly Gly
            20

<210> SEQ ID NO 6
<211> LENGTH: 2010
<212> TYPE: DNA
<213> ORGANISM: Artificial Sequence
<220> FEATURE:
<223> OTHER INFORMATION: A FRET biosensor of PKA

<400> SEQUENCE: 6
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagct gatctgcacc accggcaagc tgcccgtgcc ctggcccacc   180
ctcgtgacca ccctgggcta cggcctgcag tgcttcgccc gctaccccga ccacatgaag   240
cagcacgact cttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca ccgccgacaa gcagaagaac   480
ggcatcaagg ccaacttcaa gatccgccac aacatcgagg acggcggcgt gcagctcgcc   540
gaccactacc agcagaacac ccccatcggc gacggccccg tgctgctgcc cgacaaccac   600
tacctgagct accagtccgc cctgagcaaa gaccccaacg agaagcgcga tcacatggtc   660
ctgctggagt tcgtgaccgc cgccgggatc actctcggca tggacgagct gtacctcgag   720 aagtttctc aagaacagat cggcgaaaac attgtgtgca gggtcatttg taccacgggt   780
caaattccca tccgagattt gtcagctgat atttcacaag tgcttaagga aaacgatcc    840
```

| | |
|---|---|
| ataaagaaag tttggacatt tggtagaaac ccagcctgtg actatcattt aggaaacatt | 900 |
| tcaagactgt caaataagca tttccaaata ctactaggag aagacggtaa cctttttattg | 960 |
| aatgacattt ccactaatgg gacctggtta aatgggcaaa aagtcgagaa gaacagcaat | 1020 |
| cagttactgt cccaaggtga tgaaataacc gttggtgtag gcgtggaatc agatatttta | 1080 |
| tctctggtca ttttcataaa cgacaaattt aagcagtgcc tggagcagaa caaagttgat | 1140 |
| cgcggtacca gtgctggtgg tagtgctggt ggtagtgctg gtggtagtgc tggtggtagt | 1200 |
| gctggtggtt ccggattgag gcgcgcgacg ctggttgacg gcggccgcat ggtgagcaag | 1260 |
| ggcgaggagc tgttcaccgg ggtggtgccc atcctggtcg agctggacgg cgacgtaaac | 1320 |
| ggccacaagt tcagcgtgtc cggcgagggc gagggcgatg ccacctacgg caagctgacc | 1380 |
| ctgaagttca tctgcaccac cggcaagctg cccgtgccct ggcccaccct cgtgaccacc | 1440 |
| ctgacctggg gcgtgcagtg cttcagccgc taccccgacc acatgaagca gcacgacttc | 1500 |
| ttcaagtccg ccatgcccga aggctacgtc caggagcgca ccatcttctt caaggacgac | 1560 |
| ggcaactaca agacccgcgc cgaggtgaag ttcgagggcg acaccctggt gaaccgcatc | 1620 |
| gagctgaagg gcatcgactt caaggaggac ggcaacatcc tggggcacaa gctggagtac | 1680 |
| aactacatca gccacaacgt ctatatcacc gccgacaagc agaagaacgg catcaaggcc | 1740 |
| aacttcaaga tccgccacaa catcgaggac ggcagcgtgc agctcgccga ccactaccag | 1800 |
| cagaacaccc ccatcggcga cggccccgtg ctgctgcccg acaaccacta cttgagcacc | 1860 |
| cagtccgccc tgagcaaaga ccccaacgag aagcgcgatc acatggtcct gctggagttc | 1920 |
| gtgaccgccg ccgggatcac tctcggcatg gacgagctgg ccgctctag actgcagctg | 1980 |
| cctcctctgg aacgcctgac tctggattaa | 2010 |

<210> SEQ ID NO 7
<211> LENGTH: 669
<212> TYPE: PRT
<213> ORGANISM: Artificial Sequence
<220> FEATURE:
<223> OTHER INFORMATION: A FRET biosensor of PKA

<400> SEQUENCE: 7

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160
```

-continued

Gly Ile Lys Ala Asn Phe Lys Ile Arg His Asn Ile Glu Asp Gly Gly
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
            195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Leu Glu
225                 230                 235                 240

Lys Phe Ser Gln Glu Gln Ile Gly Glu Asn Ile Val Cys Arg Val Ile
            245                 250                 255

Cys Thr Thr Gly Gln Ile Pro Ile Arg Asp Leu Ser Ala Asp Ile Ser
            260                 265                 270

Gln Val Leu Lys Glu Lys Arg Ser Ile Lys Lys Val Trp Thr Phe Gly
            275                 280                 285

Arg Asn Pro Ala Cys Asp Tyr His Leu Gly Asn Ile Ser Arg Leu Ser
            290                 295                 300

Asn Lys His Phe Gln Ile Leu Leu Gly Glu Asp Gly Asn Leu Leu Leu
305                 310                 315                 320

Asn Asp Ile Ser Thr Asn Gly Thr Trp Leu Asn Gly Gln Lys Val Glu
                325                 330                 335

Lys Asn Ser Asn Gln Leu Leu Ser Gln Gly Asp Glu Ile Thr Val Gly
            340                 345                 350

Val Gly Val Glu Ser Asp Ile Leu Ser Leu Val Ile Phe Ile Asn Asp
            355                 360                 365

Lys Phe Lys Gln Cys Leu Glu Gln Asn Lys Val Asp Arg Gly Thr Ser
370                 375                 380

Ala Gly Gly Ser Ala Gly Gly Ser Ala Gly Gly Ser Ala Gly Gly Ser
385                 390                 395                 400

Ala Gly Gly Ser Gly Leu Arg Arg Ala Thr Leu Val Asp Gly Asp Arg
                405                 410                 415

Met Val Ser Lys Gly Glu Glu Leu Phe Thr Gly Val Val Pro Ile Leu
            420                 425                 430

Val Glu Leu Asp Gly Asp Val Asn Gly His Lys Phe Ser Val Ser Gly
            435                 440                 445

Glu Gly Glu Gly Asp Ala Thr Tyr Gly Lys Leu Thr Leu Lys Phe Ile
450                 455                 460

Cys Thr Thr Gly Lys Leu Pro Val Pro Trp Pro Thr Leu Val Thr Thr
465                 470                 475                 480

Leu Thr Trp Gly Val Gln Cys Phe Ser Arg Tyr Pro Asp His Met Lys
                485                 490                 495

Gln His Asp Phe Phe Lys Ser Ala Met Pro Glu Gly Tyr Val Gln Glu
            500                 505                 510

Arg Thr Ile Phe Phe Lys Asp Asp Gly Asn Tyr Lys Thr Arg Ala Glu
            515                 520                 525

Val Lys Phe Glu Gly Asp Thr Leu Val Asn Arg Ile Glu Leu Lys Gly
            530                 535                 540

Ile Asp Phe Lys Glu Asp Gly Asn Ile Leu Gly His Lys Leu Glu Tyr
545                 550                 555                 560

Asn Tyr Ile Ser His Asn Val Tyr Ile Thr Ala Asp Lys Gln Lys Asn
                565                 570                 575

```
Gly Ile Lys Ala Asn Phe Lys Ile Arg His Asn Ile Glu Asp Gly Ser
                580                 585                 590

Val Gln Leu Ala Asp His Tyr Gln Gln Asn Thr Pro Ile Gly Asp Gly
            595                 600                 605

Pro Val Leu Leu Pro Asp Asn His Tyr Leu Ser Thr Gln Ser Ala Leu
        610                 615                 620

Ser Lys Asp Pro Asn Glu Lys Arg Asp His Met Val Leu Leu Glu Phe
625                 630                 635                 640

Val Thr Ala Ala Gly Ile Thr Leu Gly Met Asp Glu Leu Gly Arg Ser
                645                 650                 655

Arg Leu Gln Leu Pro Pro Leu Glu Arg Leu Thr Leu Asp
            660                 665

<210> SEQ ID NO 8
<211> LENGTH: 30
<212> TYPE: DNA
<213> ORGANISM: Artificial Sequence
<220> FEATURE:
<223> OTHER INFORMATION: A forward primer

<400> SEQUENCE: 8
ccggcagtgc tggtggtagt gctggtggta                                    30

<210> SEQ ID NO 9
<211> LENGTH: 30
<212> TYPE: DNA
<213> ORGANISM: Artificial Sequence
<220> FEATURE:
<223> OTHER INFORMATION: A reverse primer

<400> SEQUENCE: 9
gtactaccac cagcactacc accagcactg                                    30

<210> SEQ ID NO 10
<211> LENGTH: 2106
<212> TYPE: DNA
<213> ORGANISM: Artificial Sequence
<220> FEATURE:
<223> OTHER INFORMATION: A FRET biosensor of PKA

<400> SEQUENCE: 10
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct gatctgcacc accggcaagc tgcccgtgcc ctggcccacc     180
ctcgtgacca ccctgggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctgggccac     420
aagctggagt acaactacaa cagccacaac gtctatatca ccgccgacaa gcagaagaac     480
ggcatcaagg ccaacttcaa gatccgccac aacatcgagg acggcggcgt gcagctcgcc     540
gaccactacc agcagaacac ccccatcggc gacggccccg tgctgctgcc cgacaaccac     600
tacctgagct accagtccgc cctgagcaaa gaccccaacg agaagcgcga tcacatggtc     660
ctgctggagt tcgtgaccgc cgccgggatc actctcggca tggacgagct gtacctcgag     720
aagttttctc aagaacagat cggcgaaaac attgtgtgca ggtcatttgt accacgggt      780 caaattccca tccgagattt gtcagctgat atttcacaag tgcttaagga aaacgatcc      840
```

```
ataaagaaag tttggacatt tggtagaaac ccagcctgtg actatcattt aggaaacatt    900
tcaagactgt caaataagca tttccaaata ctactaggag aagacggtaa ccttttattg    960
aatgacattt ccactaatgg gacctggtta aatgggcaaa aagtcgagaa gaacagcaat   1020
cagttactgt cccaaggtga tgaaataacc gttggtgtag gcgtggaatc agatatttta   1080
tctctggtca ttttcataaa cgacaaattt aagcagtgcc tggagcagaa caaagttgat   1140
cgcggtacca gtgctggtgg tagtgctggt ggtagtgctg gtggtagtgc tggtggtagt   1200
gctggtggtt ccggcagtgc tggtggtagt gctggtggta gtaccagtgc tggtggtagt   1260
gctggtggta gtgctggtgg tagtgctggt ggtagtgctg gtggttccgg attgaggcgc   1320
gcgacgctgg ttgacggcgg ccgcatggtg agcaagggcg aggagctgtt caccggggtg   1380
gtgcccatcc tggtcgagct ggacggcgac gtaaacggcc acaagttcag cgtgtccggc   1440
gagggcgagg gcgatgccac ctacggcaag ctgaccctga agttcatctg caccaccggc   1500
aagctgcccg tgccctggcc caccctcgtg accaccctga cctggggcgt gcagtgcttc   1560
agccgctacc ccgaccacat gaagcagcac gacttcttca gtccgccat gcccgaaggc   1620
tacgtccagg agcgcaccat cttcttcaag gacgacggca actacaagac ccgcgccgag   1680
gtgaagttcg agggcgacac cctggtgaac cgcatcgagc tgaagggcat cgacttcaag   1740
gaggacggca acatcctggg gcacaagctg gagtacaact acatcagcca caacgtctat   1800
atcaccgccg acaagcagaa gaacggcatc aaggccaact tcaagatccg ccacaacatc   1860
gaggacggca gcgtgcagct cgccgaccac taccagcaga acacccccat cggcgacggc   1920
cccgtgctgc tgcccgacaa ccactacttg agcacccagt ccgccctgag caaagacccc   1980
aacgagaagc gcgatcacat ggtcctgctg gagttcgtga ccgccgccgg gatcactctc   2040
ggcatggacg agctgggccg ctctagactg cagctgcctc ctctggaacg cctgactctg   2100
gattaa                                                              2106
```

<210> SEQ ID NO 11
<211> LENGTH: 701
<212> TYPE: PRT
<213> ORGANISM: Artificial Sequence
<220> FEATURE:
<223> OTHER INFORMATION: A FRET biosensor of PKA

<400> SEQUENCE: 11

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Leu Ile
            35                  40                  45

Cys Thr Thr Gly Lys Leu Pro Val Pro Trp Pro Thr Leu Val Thr Thr
        50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125
```

```
Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
                195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Leu Glu
225                 230                 235                 240

Lys Phe Ser Gln Glu Gln Ile Gly Glu Asn Ile Val Cys Arg Val Ile
                245                 250                 255

Cys Thr Thr Gly Gln Ile Pro Ile Arg Asp Leu Ser Ala Asp Ile Ser
            260                 265                 270

Gln Val Leu Lys Glu Lys Arg Ser Ile Lys Lys Val Trp Thr Phe Gly
        275                 280                 285

Arg Asn Pro Ala Cys Asp Tyr His Leu Gly Asn Ile Ser Arg Leu Ser
290                 295                 300

Asn Lys His Phe Gln Ile Leu Leu Gly Glu Asp Gly Asn Leu Leu Leu
305                 310                 315                 320

Asn Asp Ile Ser Thr Asn Gly Thr Trp Leu Asn Gly Gln Lys Val Glu
                325                 330                 335

Lys Asn Ser Asn Gln Leu Leu Ser Gln Gly Asp Glu Ile Thr Val Gly
            340                 345                 350

Val Gly Val Glu Ser Asp Ile Leu Ser Leu Val Ile Phe Ile Asn Asp
        355                 360                 365

Lys Phe Lys Gln Cys Leu Glu Gln Asn Lys Val Asp Arg Gly Thr Ser
370                 375                 380

Ala Gly Gly Ser Ala Gly Gly Ser Ala Gly Gly Ser Ala Gly Gly Ser
385                 390                 395                 400

Ala Gly Gly Ser Gly Ser Ala Gly Gly Ser Ala Gly Ser Thr Ser
                405                 410                 415

Ala Gly Gly Ser Ala Gly Gly Ser Ala Gly Gly Ser Ala Gly Gly Ser
                420                 425                 430

Ala Gly Gly Ser Gly Leu Arg Arg Ala Thr Leu Val Asp Gly Gly Arg
            435                 440                 445

Met Val Ser Lys Gly Glu Glu Leu Phe Thr Gly Val Val Pro Ile Leu
450                 455                 460

Val Glu Leu Asp Gly Asp Val Asn Gly His Lys Phe Ser Val Ser Gly
465                 470                 475                 480

Glu Gly Glu Gly Asp Ala Thr Tyr Gly Lys Leu Thr Leu Lys Phe Ile
                485                 490                 495

Cys Thr Thr Gly Lys Leu Pro Val Pro Trp Pro Thr Leu Val Thr Thr
            500                 505                 510

Leu Thr Trp Gly Val Gln Cys Phe Ser Arg Tyr Pro Asp His Met Lys
        515                 520                 525

Gln His Asp Phe Phe Lys Ser Ala Met Pro Glu Gly Tyr Val Gln Glu
530                 535                 540

Arg Thr Ile Phe Phe Lys Asp Asp Gly Asn Tyr Lys Thr Arg Ala Glu
```

```
                    545                 550                 555                 560
Val Lys Phe Glu Gly Asp Thr Leu Val Asn Arg Ile Glu Leu Lys Gly
                565                 570                 575

Ile Asp Phe Lys Glu Asp Gly Asn Ile Leu Gly His Lys Leu Glu Tyr
                580                 585                 590

Asn Tyr Ile Ser His Asn Val Tyr Ile Thr Ala Asp Lys Gln Lys Asn
                595                 600                 605

Gly Ile Lys Ala Asn Phe Lys Ile Arg His Asn Ile Glu Asp Gly Ser
            610                 615                 620

Val Gln Leu Ala Asp His Tyr Gln Gln Asn Thr Pro Ile Gly Asp Gly
625                 630                 635                 640

Pro Val Leu Leu Pro Asp Asn His Tyr Leu Ser Thr Gln Ser Ala Leu
                645                 650                 655

Ser Lys Asp Pro Asn Glu Lys Arg Asp His Met Val Leu Leu Glu Phe
                660                 665                 670

Val Thr Ala Ala Gly Ile Thr Leu Gly Met Asp Glu Leu Gly Arg Ser
                675                 680                 685

Arg Leu Gln Leu Pro Pro Leu Glu Arg Leu Thr Leu Asp
            690                 695                 700

<210> SEQ ID NO 12
<211> LENGTH: 52
<212> TYPE: PRT
<213> ORGANISM: Artificial Sequence
<220> FEATURE:
<223> OTHER INFORMATION: A 52 amino acid linker

<400> SEQUENCE: 12

Ser Ala Gly Gly Ser Ala Gly Gly Ser Ala Gly Gly Ser Ala Gly Gly
1               5                   10                  15

Ser Ala Gly Gly Ser Gly Ser Ala Gly Gly Ser Ala Gly Gly Ser Thr
                20                  25                  30

Ser Ala Gly Gly Ser Ala Gly Gly Ser Ala Gly Gly Ser Ala Gly Gly
            35                  40                  45

Ser Ala Gly Gly
    50

<210> SEQ ID NO 13
<211> LENGTH: 2202
<212> TYPE: DNA
<213> ORGANISM: Artificial Sequence
<220> FEATURE:
<223> OTHER INFORMATION: A FRET biosensor of PKA

<400> SEQUENCE: 13
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct ctatgtcacc accggcaagc tgcccgtgcc ctggcccacc     180
ctcgtgacca ccctgggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctgggccac     420
aagctggagt acaactacaa cagccacaac gtctatatca ccgccgacaa gcagaagaac     480
ggcatcaagg ccaacttcaa gatccgccac aacatcgagg acggcggcgt gcagctcgcc     540
```

```
gaccactacc agcagaacac ccccatcggc gacggccccg tgctgctgcc cgacaaccac    600
tacctgagct accagtccgc cctgttcaaa gaccccaacg agaagcgcga tcacatggtc    660
ctgctggagt tcctgaccgc cgccgggatc actgagggca tgaacgagct gtacctcgag    720 aagtttctc aagaacagat cggcgaaaac attgtgtgca gggtcatttg taccacgggt    780
caaattccca tccgagattt gtcagctgat atttcacaag tgcttaagga aaacgatcc    840 ataaagaaag tttggacatt tggtagaaac ccagcctgtg actatcattt aggaaacatt    900
tcaagactgt caaataagca tttccaaata ctactaggag aagacggtaa ccttttattg    960
aatgacattt ccactaatgg gacctggtta aatgggcaaa agtcgagaa gaacagcaat   1020 cagttactgt cccaaggtga tgaaataacc gttggtgtag gcgtggaatc agatatttta   1080
tctctggtca ttttcataaa cgacaaattt aagcagtgcc tggagcagaa caaagttgat   1140
cgcggtacca gtgctggtgg tagtgctggt ggtagtgctg gtggtagtgc tggtggtagt   1200
gctggtggtt ccggcagtgc tggtggtagt gctggtggta gtaccagtgc tggtggtagt   1260
gctggtggta gtgctggtgg tagtgctggt ggtagtgctg gtggttccgg cagtgctggt   1320
ggtagtgctg gtggtagtac cagtgctggt ggtagtgctg gtggtagtgc tggtggtagt   1380
gctggtggta gtgctggtgg ttccggattg aggcgcgcga cgctggttga cggcggccgc   1440
atggtgagca agggcgagga gctgttcacc ggggtggtgc ccatcctggt cgagctggac   1500
ggcgacgtaa acggccacaa gttcagcgtg tccggcgagg gcgagggcga tgccacctac   1560
ggcaagctga ccctgaagtt catctgcacc accggcaagc tgcccgtgcc ctggcccacc   1620
ctcgtgacca ccctgacctg ggcgtgcag tgcttcagcc gctaccccga ccacatgaag   1680
cagcacgact tcttcaagtc cgccatgccc gaaggctacg tccaggagcg caccatcttc   1740
ttcaaggacg acggcaacta caagacccgc gccgagggta agttcgaggg cgacaccctg   1800
gtgaaccgca tcgagctgaa gggcatcgac ttcaaggagg acggcaacat cctggggcac   1860
aagctggagt acaactacat cagccacaac gtctatatca ccgccgacaa gcagaagaac   1920
ggcatcaagg ccaacttcaa gatccgccac aacatcgagg acggcagcgt gcagctcgcc   1980
gaccactacc agcagaacac ccccatcggc gacggccccg tgctgctgcc cgacaaccac   2040
tacttgagca cccagtccgc cctgagcaaa gaccccaacg agaagcgcga tcacatggtc   2100
ctgctggagt tcgtgaccgc cgccgggatc actctcggca tggacgagct gggccgctct   2160
agactgcagc tgcctcctct ggaacgcctg actctggatt aa                      2202
```

<210> SEQ ID NO 14
<211> LENGTH: 733
<212> TYPE: PRT
<213> ORGANISM: Artificial Sequence
<220> FEATURE:
<223> OTHER INFORMATION: A FRET biosensor of PKA

<400> SEQUENCE: 14

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Leu
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys

-continued

```
                65                  70                  75                  80
        Gln His Asp Phe Phe Lys Ser Ala Met Pro Glu Gly Tyr Val Gln Glu
                                85                  90                  95

Arg Thr Ile Phe Phe Lys Asp Asp Gly Asn Tyr Lys Thr Arg Ala Glu
                               100                 105                 110

Val Lys Phe Glu Gly Asp Thr Leu Val Asn Arg Ile Glu Leu Lys Gly
                       115                 120                 125

Ile Asp Phe Lys Glu Asp Gly Asn Ile Leu Gly His Lys Leu Glu Tyr
                130                 135                 140

Asn Tyr Asn Ser His Asn Val Tyr Ile Thr Ala Asp Lys Gln Lys Asn
        145                 150                 155                 160

Gly Ile Lys Ala Asn Phe Lys Ile Arg His Asn Ile Glu Asp Gly Gly
                            165                 170                 175

Val Gln Leu Ala Asp His Tyr Gln Gln Asn Thr Pro Ile Gly Asp Gly
                        180                 185                 190

Pro Val Leu Leu Pro Asp Asn His Tyr Leu Ser Tyr Gln Ser Ala Leu
                    195                 200                 205

Phe Lys Asp Pro Asn Glu Lys Arg Asp His Met Val Leu Leu Glu Phe
                210                 215                 220

Leu Thr Ala Ala Gly Ile Thr Glu Gly Met Asn Glu Leu Tyr Leu Glu
        225                 230                 235                 240

Lys Phe Ser Gln Glu Gln Ile Gly Glu Asn Ile Val Cys Arg Val Ile
                            245                 250                 255

Cys Thr Thr Gly Gln Ile Pro Ile Arg Asp Leu Ser Ala Asp Ile Ser
                        260                 265                 270

Gln Val Leu Lys Glu Lys Arg Ser Ile Lys Lys Val Trp Thr Phe Gly
                    275                 280                 285

Arg Asn Pro Ala Cys Asp Tyr His Leu Gly Asn Ile Ser Arg Leu Ser
                290                 295                 300

Asn Lys His Phe Gln Ile Leu Leu Gly Glu Asp Gly Asn Leu Leu Leu
        305                 310                 315                 320

Asn Asp Ile Ser Thr Asn Gly Thr Trp Leu Asn Gly Gln Lys Val Glu
                            325                 330                 335

Lys Asn Ser Asn Gln Leu Leu Ser Gln Gly Asp Glu Ile Thr Val Gly
                        340                 345                 350

Val Gly Val Glu Ser Asp Ile Leu Ser Leu Val Ile Phe Ile Asn Asp
                    355                 360                 365

Lys Phe Lys Gln Cys Leu Glu Gln Asn Lys Val Asp Arg Gly Thr Ser
                370                 375                 380

Ala Gly Gly Ser Ala Gly Gly Ser Ala Gly Gly Ser Ala Gly Gly Ser
        385                 390                 395                 400

Ala Gly Gly Ser Gly Ser Ala Gly Gly Ser Ala Gly Gly Ser Thr Ser
                            405                 410                 415

Ala Gly Gly Ser Ala Gly Gly Ser Ala Gly Gly Ser Ala Gly Gly Ser
                        420                 425                 430

Ala Gly Gly Ser Gly Ser Ala Gly Gly Ser Ala Gly Gly Ser Thr Ser
                    435                 440                 445

Ala Gly Gly Ser Ala Gly Gly Ser Ala Gly Gly Ser Ala Gly Gly Ser
                450                 455                 460

Ala Gly Gly Ser Gly Leu Arg Arg Ala Thr Leu Val Asp Gly Arg
        465                 470                 475                 480

Met Val Ser Lys Gly Glu Glu Leu Phe Thr Gly Val Val Pro Ile Leu
                            485                 490                 495
```

-continued

Val Glu Leu Asp Gly Asp Val Asn Gly His Lys Phe Ser Val Ser Gly
            500                 505                 510

Glu Gly Glu Gly Asp Ala Thr Tyr Gly Lys Leu Thr Leu Lys Phe Ile
            515                 520                 525

Cys Thr Thr Gly Lys Leu Pro Val Pro Trp Pro Thr Leu Val Thr Thr
530                 535                 540

Leu Thr Trp Gly Val Gln Cys Phe Ser Arg Tyr Pro Asp His Met Lys
545                 550                 555                 560

Gln His Asp Phe Phe Lys Ser Ala Met Pro Glu Gly Tyr Val Gln Glu
                565                 570                 575

Arg Thr Ile Phe Phe Lys Asp Asp Gly Asn Tyr Lys Thr Arg Ala Glu
            580                 585                 590

Val Lys Phe Glu Gly Asp Thr Leu Val Asn Arg Ile Glu Leu Lys Gly
            595                 600                 605

Ile Asp Phe Lys Glu Asp Gly Asn Ile Leu Gly His Lys Leu Glu Tyr
            610                 615                 620

Asn Tyr Ile Ser His Asn Val Tyr Ile Thr Ala Asp Lys Gln Lys Asn
625                 630                 635                 640

Gly Ile Lys Ala Asn Phe Lys Ile Arg His Asn Ile Glu Asp Gly Ser
                645                 650                 655

Val Gln Leu Ala Asp His Tyr Gln Gln Asn Thr Pro Ile Gly Asp Gly
            660                 665                 670

Pro Val Leu Leu Pro Asp Asn His Tyr Leu Ser Thr Gln Ser Ala Leu
            675                 680                 685

Ser Lys Asp Pro Asn Glu Lys Arg Asp His Met Val Leu Leu Glu Phe
            690                 695                 700

Val Thr Ala Ala Gly Ile Thr Leu Gly Met Asp Glu Leu Gly Arg Ser
705                 710                 715                 720

Arg Leu Gln Leu Pro Pro Leu Glu Arg Leu Thr Leu Asp
                725                 730

<210> SEQ ID NO 15
<211> LENGTH: 84
<212> TYPE: PRT
<213> ORGANISM: Artificial Sequence
<220> FEATURE:
<223> OTHER INFORMATION: A 84 amino acid linker

<400> SEQUENCE: 15

Ser Ala Gly Gly Ser Ala Gly Gly Ser Ala Gly Gly Ser Ala Gly Gly
1               5                   10                  15

Ser Ala Gly Gly Ser Gly Ser Ala Gly Gly Ser Ala Gly Gly Ser Thr
            20                  25                  30

Ser Ala Gly Gly Ser Ala Gly Gly Ser Ala Gly Gly Ser Ala Gly Gly
            35                  40                  45

Ser Ala Gly Gly Ser Gly Ser Ala Gly Gly Ser Ala Gly Gly Ser Thr
            50                  55                  60

Ser Ala Gly Gly Ser Ala Gly Gly Ser Ala Gly Gly Ser Ala Gly Gly
65                  70                  75                  80

Ser Ala Gly Gly

<210> SEQ ID NO 16
<211> LENGTH: 2292
<212> TYPE: DNA
<213> ORGANISM: Artificial Sequence
<220> FEATURE:

<223> OTHER INFORMATION: A FRET biosensor of PKA

<400> SEQUENCE: 16

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct ctatgcacc accggcaagc tgcccgtgcc ctggcccacc      180
ctcgtgacca ccctgggcta cggcctgcag tgcttcgccc gctacccgga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca ccgccgacaa gcagaagaac     480
ggcatcaagg ccaacttcaa gatccgccac aacatcgagg acggcggcgt gcagctcgcc     540
gaccactacc agcagaacac ccccatcggc gacggccccg tgctgctgcc cgacaaccac     600
tacctgagct accagtccgc cctgttcaaa gaccccaacg agaagcgcga tcacatggtc     660
ctgctggagt tcgtgaccgc cgccgggatc actgagggca tgaacgagct gtacctcgag     720
aagtttctc aagaacagat cggcgaaaac attgtgtgca gggtcatttg taccacgggt      780
caaattccca tccgagattt gtcagctgat atttcacaag tgcttaagga aaaacgatcc     840
ataaagaaag tttggacatt tggtagaaac ccagcctgtg actatcattt aggaaacatt     900
tcaagactgt caaataagca tttccaaata ctactaggag aagacggtaa cctttattg      960
aatgacattt ccactaatgg gacctggtta aatgggcaaa aagtcgagaa gaacagcaat    1020
cagttactgt cccaaggtga tgaaataacc gttggtgtag gcgtggaatc agatatttta    1080
tctctggtca ttttcataaa cgacaaattt aagcagtgcc tggagcagaa caagttgat     1140
cgcggtacca gtgctggtgg tagtgctggt ggtagtgctg gtggtagtgc tggtggtagt    1200
gctggtggtt ccggcagtgc tggtggtagt gctggtggta gtaccagtgc tggtggtagt    1260
gctggtggta gtgctggtgg tagtgctggt ggtagtgctg gtggttccgg cagtgctggt    1320
ggtagtgctg gtggtagtac cagtgctggt ggtagtgctg gtggtagtgc tggtggtagt    1380
gctggtggta gtgctggtgg ttccggcagt gctggtggta gtgctggtgg tagtaccagt    1440
gctggtggta gtgctggtgg tagtgctggt ggtagtgctg gtggtagtgc tggtggttcc    1500
ggattgaggc gcgcgacgct ggttgacggc ggccgcatgg tgagcaaggg cgaggagctg    1560
ttcaccgggg tggtgcccat cctggtcgag ctggacggcg acgtaaacgg ccacaggttc    1620
agcgtgtccg gcgagggcga gggcgatgcc acctacggca agctgaccct gaagttcatc    1680
tgcaccaccg gcaagctgcc cgtgccctgg cccaccctcg tgaccaccct gacctggggc    1740
gtgcagtgct tcagccgcta ccccgaccac atgaagcagc acgacttctt caagtccgcc    1800
atgcccgaag gctacgtcca ggagcgtacc atcttcttca aggacgacgg caactacaag    1860
acccgcgccg aggtgaagtt cgagggcgac accctggtga accgcatcga gctgaagggc    1920
atcggcttca aggaggacgg caacatcctg ggcacaagc tagagtacaa ctacatcagc     1980
cacaacgtct atatcaccgc cgacaagcag aagaacggca tcaaggccca cttcaagatc    2040
cgccacaaca tcgaggacgg cggcgtgcag ctcgccgacc actaccagca gaacaccccc    2100
atcggcgacg gccccgtgct gctgcccgac aaccactacc tgagcaccca gtccgccctg    2160
agcaaagacc ccaacgagaa gcgcgatcac atggtcctgc tggagttcgt gaccgccgcc    2220
gggatcactc tcggcatgga cgagctgtac tagactgcagc tgcctcctct ggaacgcctg    2280
```
actctggatt aa 2292

<210> SEQ ID NO 17
<211> LENGTH: 763
<212> TYPE: PRT
<213> ORGANISM: Artificial Sequence
<220> FEATURE:
<223> OTHER INFORMATION: A FRET bionsensor of PKA

<400> SEQUENCE: 17

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Leu
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Phe Lys Asp Pro Asn Glu Lys Arg Asp His Met Val Leu Leu Glu Phe
    210                 215                 220

Leu Thr Ala Ala Gly Ile Thr Glu Gly Met Asn Glu Leu Tyr Leu Glu
225                 230                 235                 240

Lys Phe Ser Gln Glu Gln Ile Gly Glu Asn Ile Val Cys Arg Val Ile
                245                 250                 255

Cys Thr Thr Gly Gln Ile Pro Ile Arg Asp Leu Ser Ala Asp Ile Ser
            260                 265                 270

Gln Val Leu Lys Glu Lys Arg Ser Ile Lys Lys Val Trp Thr Phe Gly
        275                 280                 285

Arg Asn Pro Ala Cys Asp Tyr His Leu Gly Asn Ile Ser Arg Leu Ser
    290                 295                 300

Asn Lys His Phe Gln Ile Leu Leu Gly Glu Asp Gly Asn Leu Leu Leu
305                 310                 315                 320

Asn Asp Ile Ser Thr Asn Gly Thr Trp Leu Asn Gly Gln Lys Val Glu
                325                 330                 335

Lys Asn Ser Asn Gln Leu Leu Ser Gln Gly Asp Glu Ile Thr Val Gly
            340                 345                 350
```

```
Val Gly Val Glu Ser Asp Ile Leu Ser Leu Val Ile Phe Ile Asn Asp
            355                 360                 365
Lys Phe Lys Gln Cys Leu Glu Gln Asn Lys Val Asp Arg Gly Thr Ser
370                 375                 380
Ala Gly Gly Ser Ala Gly Gly Ser Ala Gly Gly Ser Ala Gly Gly Ser
385                 390                 395                 400
Ala Gly Gly Ser Gly Ser Ala Gly Gly Ser Ala Gly Ser Thr Ser
                405                 410                 415
Ala Gly Gly Ser Ala Gly Gly Ser Ala Gly Gly Ser Ala Gly Gly Ser
                420                 425                 430
Ala Gly Gly Ser Gly Ser Ala Gly Gly Ser Ala Gly Ser Thr Ser
            435                 440                 445
Ala Gly Gly Ser Ala Gly Gly Ser Ala Gly Gly Ser Ala Gly Gly Ser
            450                 455                 460
Ala Gly Gly Ser Gly Ser Ala Gly Gly Ser Ala Gly Ser Thr Ser
465                 470                 475                 480
Ala Gly Gly Ser Ala Gly Gly Ser Ala Gly Gly Ser Ala Gly Gly Ser
                485                 490                 495
Ala Gly Gly Ser Gly Leu Arg Arg Ala Thr Leu Val Asp Gly Gly Arg
            500                 505                 510
Met Val Ser Lys Gly Glu Glu Leu Phe Thr Gly Val Val Pro Ile Leu
            515                 520                 525
Val Glu Leu Asp Gly Asp Val Asn Gly His Arg Phe Ser Val Ser Gly
            530                 535                 540
Glu Gly Glu Gly Asp Ala Thr Tyr Gly Lys Leu Thr Leu Lys Phe Ile
545                 550                 555                 560
Cys Thr Thr Gly Lys Leu Pro Val Pro Trp Pro Thr Leu Val Thr Thr
                565                 570                 575
Leu Thr Trp Gly Val Gln Cys Phe Ser Arg Tyr Pro Asp His Met Lys
            580                 585                 590
Gln His Asp Phe Phe Lys Ser Ala Met Pro Glu Gly Tyr Val Gln Glu
        595                 600                 605
Arg Thr Ile Phe Phe Lys Asp Asp Gly Asn Tyr Lys Thr Arg Ala Glu
610                 615                 620
Val Lys Phe Glu Gly Asp Thr Leu Val Asn Arg Ile Glu Leu Lys Gly
625                 630                 635                 640
Ile Gly Phe Lys Glu Asp Gly Asn Ile Leu Gly His Lys Leu Glu Tyr
                645                 650                 655
Asn Tyr Ile Ser His Asn Val Tyr Ile Thr Ala Asp Lys Gln Lys Asn
            660                 665                 670
Gly Ile Lys Ala His Phe Lys Ile Arg His Asn Ile Glu Asp Gly Gly
        675                 680                 685
Val Gln Leu Ala Asp His Tyr Gln Gln Asn Thr Pro Ile Gly Asp Gly
        690                 695                 700
Pro Val Leu Leu Pro Asp Asn His Tyr Leu Ser Thr Gln Ser Ala Leu
705                 710                 715                 720
Ser Lys Asp Pro Asn Glu Lys Arg Asp His Met Val Leu Leu Glu Phe
            725                 730                 735
Val Thr Ala Ala Gly Ile Thr Leu Gly Met Asp Glu Leu Ser Arg Leu
                740                 745                 750
Gln Leu Pro Pro Leu Glu Arg Leu Thr Leu Asp
            755                 760
```

```
<210> SEQ ID NO 18
<211> LENGTH: 116
<212> TYPE: PRT
<213> ORGANISM: Artificial Sequence
<220> FEATURE:
<223> OTHER INFORMATION: A 116 amino acid linker

<400> SEQUENCE: 18

Ser Ala Gly Gly Ser Ala Gly Gly Ser Ala Gly Gly Ser Ala Gly Gly
1               5                   10                  15

Ser Ala Gly Gly Ser Gly Ser Ala Gly Gly Ser Ala Gly Gly Ser Thr
            20                  25                  30

Ser Ala Gly Gly Ser Ala Gly Gly Ser Ala Gly Gly Ser Ala Gly Gly
        35                  40                  45

Ser Ala Gly Gly Ser Gly Ser Ala Gly Gly Ser Ala Gly Gly Ser Thr
    50                  55                  60

Ser Ala Gly Gly Ser Ala Gly Gly Ser Ala Gly Gly Ser Ala Gly Gly
65                  70                  75                  80

Ser Ala Gly Gly Ser Gly Ser Ala Gly Gly Ser Ala Gly Gly Ser Thr
                85                  90                  95

Ser Ala Gly Gly Ser Ala Gly Gly Ser Ala Gly Gly Ser Ala Gly Gly
            100                 105                 110

Ser Ala Gly Gly
        115

<210> SEQ ID NO 19
<211> LENGTH: 1965
<212> TYPE: DNA
<213> ORGANISM: Artificial Sequence
<220> FEATURE:
<223> OTHER INFORMATION: A FRET biosensor of PKA

<400> SEQUENCE: 19
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct gatctgcacc accggcaagc tgcccgtgcc ctggcccacc     180
ctcgtgacca ccctgggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca ccgccgacaa gcagaagaac     480
ggcatcaagg ccaacttcaa gatccgccac aacatcgagg acggcggcgt gcagctcgcc     540
gaccactacc agcagaacac ccccatcggc gacggccccg tgctgctgcc cgacaaccac     600
tacctgagct accagtccgc cctgagcaaa gaccccaacg agaagcgcga tcacatggtc     660
ctgctggagt tcgtgaccgc cgccgggatc actctcggca tggacgagct gtacctcgag     720 aagtttttctc aagaacagat cggcgaaaac attgtgtgca gggtcatttg taccacgggt     780
caaattccca tccgagattt gtcagctgat atttcacaag tgcttaagga aaaacgatcc     840
ataaagaaag tttggacatt tggtagaaac ccagcctgtg actatcattt aggaaacatt     900
tcaagactgt caaataagca tttccaaata ctactaggag aagacggtaa cctttattg      960 aatgacattt ccactaatgg gacctggtta aatgggcaaa agtcgagaa gaacagcaat     1020 cagttactgt cccaaggtga tgaaataacc gttggtgtag cgtggaatc agatatttta     1080
```

```
tctctggtca ttttcataaa cgacaaattt aagcagtgcc tggagcagaa caaagttgat    1140
cgcggtaccg gaggtagtgg aggttccgga ttgaggcgcg cgacgctggt tgacggcggc    1200
cgcatggtga gcaagggcga ggagctgttc accggggtgg tgcccatcct ggtcgagctg    1260
gacggcgacg taaacggcca caagttcagc gtgtccggcg agggcgaggg cgatgccacc    1320
tacggcaagc tgaccctgaa gttcatctgc accaccggca agctgcccgt gccctggccc    1380
accctcgtga ccaccctgac ctggggcgtg cagtgcttca gccgctaccc cgaccacatg    1440
aagcagcacg acttcttcaa gtccgccatg cccgaaggct acgtccagga gcgcaccatc    1500
ttcttcaagg acgacggcaa ctacaagacc cgcgccgagg tgaagttcga gggcgacacc    1560
ctggtgaacc gcatcgagct gaagggcatc gacttcaagg aggacggcaa catcctgggg    1620
cacaagctgg agtacaacta catcagccac aacgtctata tcaccgccga caagcagaag    1680
aacggcatca aggccaactt caagatccgc cacaacatcg aggacggcag cgtgcagctc    1740
gccgaccact accagcagaa cacccccatc ggcgacggcc ccgtgctgct gcccgacaac    1800
cactacttga gcacccagtc cgccctgagc aaagacccca cgagaagcg cgatcacatg    1860 gtcctgctgg agttcgtgac cgccgccggg atcactctcg gcatggacga gctgggccgc    1920
tctagactgc agctgcctcc tctggaacgc ctgactctgg attaa                    1965
```

<210> SEQ ID NO 20
<211> LENGTH: 654
<212> TYPE: PRT
<213> ORGANISM: Artificial Sequence
<220> FEATURE:
<223> OTHER INFORMATION: A FRET biosensor of PKA

<400> SEQUENCE: 20

```
Met Val Ser Lys Gly Glu Glu Leu Phe Thr Gly Val Val Pro Ile Leu
1               5                  10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Leu Ile
            35                  40                  45

Cys Thr Thr Gly Lys Leu Pro Val Pro Trp Pro Thr Leu Val Thr Thr
        50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205
```

```
Ser Lys Asp Pro Asn Glu Lys Arg Asp His Met Val Leu Leu Glu Phe
    210             215                 220

Val Thr Ala Ala Gly Ile Thr Leu Gly Met Asp Glu Leu Tyr Leu Glu
225             230                 235                 240

Lys Phe Ser Gln Glu Gln Ile Gly Glu Asn Ile Val Cys Arg Val Ile
            245                 250                 255

Cys Thr Thr Gly Gln Ile Pro Ile Arg Asp Leu Ser Ala Asp Ile Ser
        260                 265                 270

Gln Val Leu Lys Glu Lys Arg Ser Ile Lys Lys Val Trp Thr Phe Gly
            275                 280                 285

Arg Asn Pro Ala Cys Asp Tyr His Leu Gly Asn Ile Ser Arg Leu Ser
290                 295                 300

Asn Lys His Phe Gln Ile Leu Leu Gly Glu Asp Gly Asn Leu Leu Leu
305                 310                 315                 320

Asn Asp Ile Ser Thr Asn Gly Thr Trp Leu Asn Gly Gln Lys Val Glu
                325                 330                 335

Lys Asn Ser Asn Gln Leu Leu Ser Gln Gly Asp Glu Ile Thr Val Gly
            340                 345                 350

Val Gly Val Glu Ser Asp Ile Leu Ser Leu Val Ile Phe Ile Asn Asp
        355                 360                 365

Lys Phe Lys Gln Cys Leu Glu Gln Asn Lys Val Asp Arg Gly Thr Gly
370                 375                 380

Gly Ser Gly Gly Ser Gly Leu Arg Arg Ala Thr Leu Val Asp Gly Gly
385                 390                 395                 400

Arg Met Val Ser Lys Gly Glu Glu Leu Phe Thr Gly Val Val Pro Ile
                405                 410                 415

Leu Val Glu Leu Asp Gly Asp Val Asn Gly His Lys Phe Ser Val Ser
            420                 425                 430

Gly Glu Gly Glu Gly Asp Ala Thr Tyr Gly Lys Leu Thr Leu Lys Phe
        435                 440                 445

Ile Cys Thr Thr Gly Lys Leu Pro Val Pro Trp Pro Thr Leu Val Thr
    450                 455                 460

Thr Leu Thr Trp Gly Val Gln Cys Phe Ser Arg Tyr Pro Asp His Met
465             470                 475                 480

Lys Gln His Asp Phe Phe Lys Ser Ala Met Pro Glu Gly Tyr Val Gln
            485                 490                 495

Glu Arg Thr Ile Phe Phe Lys Asp Asp Gly Asn Tyr Lys Thr Arg Ala
        500                 505                 510

Glu Val Lys Phe Glu Gly Asp Thr Leu Val Asn Arg Ile Glu Leu Lys
            515                 520                 525

Gly Ile Asp Phe Lys Glu Asp Gly Asn Ile Leu Gly His Lys Leu Glu
530                 535                 540

Tyr Asn Tyr Ile Ser His Asn Val Tyr Ile Thr Ala Asp Lys Gln Lys
545                 550                 555                 560

Asn Gly Ile Lys Ala Asn Phe Lys Ile Arg His Asn Ile Glu Asp Gly
                565                 570                 575

Ser Val Gln Leu Ala Asp His Tyr Gln Gln Asn Thr Pro Ile Gly Asp
            580                 585                 590

Gly Pro Val Leu Leu Pro Asp Asn His Tyr Leu Ser Thr Gln Ser Ala
        595                 600                 605

Leu Ser Lys Asp Pro Asn Glu Lys Arg Asp His Met Val Leu Leu Glu
610                 615                 620

Phe Val Thr Ala Ala Gly Ile Thr Leu Gly Met Asp Glu Leu Gly Arg
```

Ser Arg Leu Gln Leu Pro Pro Leu Glu Arg Leu Thr Leu Asp
            645                 650

<210> SEQ ID NO 21
<211> LENGTH: 2484
<212> TYPE: DNA
<213> ORGANISM: Artificial Sequence
<220> FEATURE:
<223> OTHER INFORMATION: A FRET biosensor of PKA

<400> SEQUENCE: 21

| | | | | | |
|---|---|---|---|---|---|
| atggtgagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagct | tctatgcacc | accggcaagc | tgcccgtgcc | ctggcccacc | 180 |
| ctcgtgacca | ccctgggcta | cggcctgcag | tgcttcgccc | gctaccccga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggagg | acggcaacat | cctggggcac | 420 |
| aagctggagt | acaactacaa | cagccacaac | gtctatatca | ccgccgacaa | gcagaagaac | 480 |
| ggcatcaagg | ccaacttcaa | gatccgccac | aacatcgagg | acggcggcgt | gcagctcgcc | 540 |
| gaccactacc | agcagaacac | ccccatcggc | gacggccccg | tgctgctgcc | cgacaaccac | 600 |
| tacctgagct | accagtccgc | cctgttcaaa | gaccccaacg | agaagcgcga | tcacatggtc | 660 |
| ctgctggagt | tcgtgaccgc | cgccgggatc | actgagggca | tgaacgagct | gtacctcgag | 720 |
| aagtttctc | aagaacagat | cggcgaaaac | attgtgtgca | gggtcatttg | taccacgggt | 780 |
| caaattccca | tccgagattt | gtcagctgat | atttcacaag | tgcttaagga | aaaacgatcc | 840 |
| ataaagaaag | tttggacatt | tggtagaaac | ccagcctgtg | actatcattt | aggaaacatt | 900 |
| tcaagactgt | caaataagca | tttccaaata | ctactaggag | aagacggtaa | ccttttattg | 960 |
| aatgacattt | ccactaatgg | gacctggtta | aatgggcaaa | agtcgagaa | gaacagcaat | 1020 |
| cagttactgt | cccaaggtga | tgaaataacc | gttggtgtag | gcgtggaatc | agatattta | 1080 |
| tctctggtca | ttttcataaa | cgacaaattt | aagcagtgcc | tggagcagaa | caaagttgat | 1140 |
| cgcggtacca | gtgctggtgg | tagtgctggt | ggtagtgctg | gtggtagtgc | tggtggtagt | 1200 |
| gctggtggtt | ccggcagtgc | tggtggtagt | gctggtggta | gtaccagtgc | tggtggtagt | 1260 |
| gctggtggta | gtgctggtgg | tagtgctggt | ggtagtgctg | gtggttccgg | cagtgctggt | 1320 |
| ggtagtgctg | gtggtagtac | cagtgctggt | ggtagtgctg | gtggtagtgc | tggtggtagt | 1380 |
| gctggtggta | gtgctggtgg | ttccggcagt | gctggtggta | gtgctggtgg | tagtaccagt | 1440 |
| gctggtggta | gtgctggtgg | tagtgctggt | ggtagtgctg | gtggtagtgc | tggtggttcc | 1500 |
| ggcagtgctg | gtggtagtgc | tggtggtagt | accagtgctg | gtggtagtgc | tggtggtagt | 1560 |
| gctggtggta | gtgctggtgg | tagtgctggt | ggttccggca | gtgctggtgg | tagtgctggt | 1620 |
| ggtagtacca | gtgctggtgg | tagtgctggt | ggtagtgctg | gtggtagtgc | tggtggtagt | 1680 |
| gctggtggtt | ccggattgag | gcgcgcgacg | ctggttgacg | gcggccgcat | ggtgagcaag | 1740 |
| ggcgaggagc | tgttcaccgg | ggtggtgccc | atcctggtcg | agctggacgg | cgacgtaaac | 1800 |
| ggccacaggt | tcagcgtgtc | cggcgagggc | gagggcgatg | ccacctacgg | caagctgacc | 1860 |
| ctgaagttca | tctgcaccac | cggcaagctg | cccgtgccct | ggcccaccct | cgtgaccacc | 1920 |

-continued

```
ctgacctggg gcgtgcagtg cttcagccgc taccccgacc acatgaagca gcacgacttc    1980
ttcaagtccg ccatgcccga aggctacgtc caggagcgta ccatcttctt caaggacgac    2040
ggcaactaca agacccgcgc cgaggtgaag ttcgagggcg acaccctggt gaaccgcatc    2100
gagctgaagg gcatcggctt caaggaggac ggcaacatcc tggggcacaa gctagagtac    2160
aactacatca gccacaacgt ctatatcacc gccgacaagc agaagaacgg catcaaggcc    2220
cacttcaaga tccgccacaa catcgaggac ggcggcgtgc agctcgccga ccactaccag    2280
cagaacaccc ccatcggcga cggccccgtg ctgctgcccg acaaccacta cctgagcacc    2340
cagtccgccc tgagcaaaga ccccaacgag aagcgcgatc acatggtcct gctggagttc    2400
gtgaccgccg ccgggatcac tctcggcatg gacgagctgt ctagactgca gctgcctcct    2460
ctggaacgcc tgactctgga ttaa                                          2484
```

<210> SEQ ID NO 22
<211> LENGTH: 827
<212> TYPE: PRT
<213> ORGANISM: Artificial Sequence
<220> FEATURE:
<223> OTHER INFORMATION: A FRET biosensor of PKA

<400> SEQUENCE: 22

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Leu
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Phe Lys Asp Pro Asn Glu Lys Arg Asp His Met Val Leu Leu Glu Phe
    210                 215                 220

Leu Thr Ala Ala Gly Ile Thr Glu Gly Met Asn Glu Leu Tyr Leu Glu
225                 230                 235                 240

Lys Phe Ser Gln Glu Gln Ile Gly Glu Asn Ile Val Cys Arg Val Ile
                245                 250                 255

Cys Thr Thr Gly Gln Ile Pro Ile Arg Asp Leu Ser Ala Asp Ile Ser
```

-continued

```
                260                 265                 270
Gln Val Leu Lys Glu Lys Arg Ser Ile Lys Val Trp Thr Phe Gly
            275                 280                 285

Arg Asn Pro Ala Cys Asp Tyr His Leu Gly Asn Ile Ser Arg Leu Ser
290                 295                 300

Asn Lys His Phe Gln Ile Leu Leu Gly Glu Gly Asn Leu Leu Leu
305                 310                 315                 320

Asn Asp Ile Ser Thr Asn Gly Thr Trp Leu Asn Gly Gln Lys Val Glu
            325                 330                 335

Lys Asn Ser Asn Gln Leu Leu Ser Gln Gly Asp Glu Ile Thr Val Gly
            340                 345                 350

Val Gly Val Glu Ser Asp Ile Leu Ser Leu Val Ile Phe Ile Asn Asp
            355                 360                 365

Lys Phe Lys Gln Cys Leu Glu Gln Asn Lys Val Asp Arg Gly Thr Ser
            370                 375                 380

Ala Gly Gly Ser Ala Gly Gly Ser Ala Gly Gly Ser Ala Gly Gly Ser
385                 390                 395                 400

Ala Gly Gly Ser Gly Ser Ala Gly Gly Ser Ala Gly Gly Ser Thr Ser
                405                 410                 415

Ala Gly Gly Ser Ala Gly Gly Ser Ala Gly Gly Ser Ala Gly Gly Ser
            420                 425                 430

Ala Gly Gly Ser Gly Ser Ala Gly Gly Ser Ala Gly Gly Ser Thr Ser
            435                 440                 445

Ala Gly Gly Ser Ala Gly Gly Ser Ala Gly Gly Ser Ala Gly Gly Ser
            450                 455                 460

Ala Gly Gly Ser Gly Ser Ala Gly Gly Ser Ala Gly Gly Ser Thr Ser
465                 470                 475                 480

Ala Gly Gly Ser Ala Gly Gly Ser Ala Gly Gly Ser Ala Gly Gly Ser
                485                 490                 495

Ala Gly Gly Ser Gly Ser Ala Gly Gly Ser Ala Gly Gly Ser Thr Ser
            500                 505                 510

Ala Gly Gly Ser Ala Gly Gly Ser Ala Gly Gly Ser Ala Gly Gly Ser
            515                 520                 525

Ala Gly Gly Ser Gly Ser Ala Gly Gly Ser Ala Gly Gly Ser Thr Ser
            530                 535                 540

Ala Gly Gly Ser Ala Gly Gly Ser Ala Gly Gly Ser Ala Gly Gly Ser
545                 550                 555                 560

Ala Gly Gly Ser Gly Leu Arg Arg Ala Thr Leu Val Asp Gly Gly Arg
                565                 570                 575

Met Val Ser Lys Gly Glu Glu Leu Phe Thr Gly Val Val Pro Ile Leu
            580                 585                 590

Val Glu Leu Asp Gly Asp Val Asn Gly His Arg Phe Ser Val Ser Gly
            595                 600                 605

Glu Gly Glu Gly Asp Ala Thr Tyr Gly Lys Leu Thr Leu Lys Phe Ile
610                 615                 620

Cys Thr Thr Gly Lys Leu Pro Val Pro Trp Pro Thr Leu Val Thr Thr
625                 630                 635                 640

Leu Thr Trp Gly Val Gln Cys Phe Ser Arg Tyr Pro Asp His Met Lys
            645                 650                 655

Gln His Asp Phe Phe Lys Ser Ala Met Pro Glu Gly Tyr Val Gln Glu
            660                 665                 670

Arg Thr Ile Phe Phe Lys Asp Asp Gly Asn Tyr Lys Thr Arg Ala Glu
            675                 680                 685
```

-continued

```
Val Lys Phe Glu Gly Asp Thr Leu Val Asn Arg Ile Glu Leu Lys Gly
            690                 695                 700

Ile Gly Phe Lys Glu Asp Gly Asn Ile Leu Gly His Lys Leu Glu Tyr
705                 710                 715                 720

Asn Tyr Ile Ser His Asn Val Tyr Ile Thr Ala Asp Lys Gln Lys Asn
                725                 730                 735

Gly Ile Lys Ala His Phe Lys Ile Arg His Asn Ile Glu Asp Gly Gly
            740                 745                 750

Val Gln Leu Ala Asp His Tyr Gln Gln Asn Thr Pro Ile Gly Asp Gly
        755                 760                 765

Pro Val Leu Leu Pro Asp Asn His Tyr Leu Ser Thr Gln Ser Ala Leu
    770                 775                 780

Ser Lys Asp Pro Asn Glu Lys Arg Asp His Met Val Leu Leu Glu Phe
785                 790                 795                 800

Val Thr Ala Ala Gly Ile Thr Leu Gly Met Asp Glu Leu Ser Arg Leu
                805                 810                 815

Gln Leu Pro Pro Leu Glu Arg Leu Thr Leu Asp
            820                 825

<210> SEQ ID NO 23
<211> LENGTH: 180
<212> TYPE: PRT
<213> ORGANISM: Artificial Sequence
<220> FEATURE:
<223> OTHER INFORMATION: A 180 amino acid linker

<400> SEQUENCE: 23

Ser Ala Gly Gly Ser Ala Gly Gly Ser Ala Gly Gly Ser Ala Gly Gly
1               5                   10                  15

Ser Ala Gly Gly Ser Gly Ser Ala Gly Gly Ser Ala Gly Gly Ser Thr
            20                  25                  30

Ser Ala Gly Gly Ser Ala Gly Gly Ser Ala Gly Gly Ser Ala Gly Gly
        35                  40                  45

Ser Ala Gly Gly Ser Gly Ser Ala Gly Gly Ser Ala Gly Gly Ser Thr
    50                  55                  60

Ser Ala Gly Gly Ser Ala Gly Gly Ser Ala Gly Gly Ser Ala Gly Gly
65                  70                  75                  80

Ser Ala Gly Gly Ser Gly Ser Ala Gly Gly Ser Ala Gly Gly Ser Thr
                85                  90                  95

Ser Ala Gly Gly Ser Ala Gly Gly Ser Ala Gly Gly Ser Ala Gly Gly
            100                 105                 110

Ser Ala Gly Gly Ser Gly Ser Ala Gly Gly Ser Ala Gly Gly Ser Thr
        115                 120                 125

Ser Ala Gly Gly Ser Ala Gly Gly Ser Ala Gly Gly Ser Ala Gly Gly
    130                 135                 140

Ser Ala Gly Gly Ser Gly Ser Ala Gly Gly Ser Ala Gly Gly Ser Thr
145                 150                 155                 160

Ser Ala Gly Gly Ser Ala Gly Gly Ser Ala Gly Gly Ser Ala Gly Gly
                165                 170                 175

Ser Ala Gly Gly
            180

<210> SEQ ID NO 24
<211> LENGTH: 2676
<212> TYPE: DNA
<213> ORGANISM: Artificial Sequence
```

<220> FEATURE:
<223> OTHER INFORMATION: A FRET biosensor of PKA

<400> SEQUENCE: 24

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct tctatgcacc accggcaagc tgcccgtgcc ctggcccacc     180
ctcgtgacca ccctgggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca ccgccgacaa gcagaagaac     480
ggcatcaagg ccaacttcaa gatccgccac aacatcgagg acggcggcgt gcagctcgcc     540
gaccactacc agcagaacac ccccatcggc gacggccccg tgctgctgcc cgacaaccac     600
tacctgagct accagtccgc cctgttcaaa gaccccaacg agaagcgcga tcacatggtc     660
ctgctggagt tcctgaccgc cgccgggatc actgagggca tgaacgagct gtacctcgag     720
aagtttctct caagaacagat cggcgaaaac attgtgtgca gggtcatttg taccacgggt     780
caaattccca tccgagattt gtcagctgat atttcacaag tgcttaagga aaaacgatcc     840
ataaagaaag tttggacatt tggtagaaac ccagcctgtg actatcattt aggaaacatt     900
tcaagactgt caaataagca tttccaaata ctactaggag aagacggtaa ccttttattg     960
aatgacattt ccactaatgg gacctggtta aatgggcaaa aagtcgagaa gaacagcaat    1020
cagttactgt cccaaggtga tgaaataacc gttggtgtag gcgtggaatc agatatttta    1080
tctctggtca ttttcataaa cgacaaattt aagcagtgcc tggagcagaa caaagttgat    1140
cgcggtacca gtgctggtgg tagtgctggt ggtagtgctg gtggtagtgc tggtggtagt    1200
gctggtggtt ccggcagtgc tggtggtagt gctggtggta gtaccagtgc tggtggtagt    1260
gctggtggta gtgctggtgg tagtgctggt ggtagtgctg gtggttccgg cagtgctggt    1320
ggtagtgctg gtggtagtac cagtgctggt ggtagtgctg gtggtagtgc tggtggtagt    1380
gctggtggta gtgctggtgg ttccggcagt gctggtggta gtgctggtgg tagtaccagt    1440
gctggtggta gtgctggtgg tagtgctggt ggtagtgctg gtggtagtgc tggtggttcc    1500
ggcagtgctg gtggtagtgc tggtggtagt accagtgctg gtggtagtgc tggtggtagt    1560
gctggtggta gtgctggtgg tagtgctggt ggttccggca gtgctggtgg tagtgctggt    1620
ggtagtacca gtgctggtgg tagtgctggt ggtagtgctg gtggtagtgc tggtggtagt    1680
gctggtggtt ccggcagtgc tggtggtagt gctggtggta gtaccagtgc tggtggtagt    1740
gctggtggta gtgctggtgg tagtgctggt ggtagtgctg gtggttccgg cagtgctggt    1800
ggtagtgctg gtggtagtac cagtgctggt ggtagtgctg gtggtagtgc tggtggtagt    1860
gctggtggta gtgctggtgg ttccggattg aggcgcgcga cgctggttga cggcggccgc    1920
atggtgagca agggcgagga gctgttcacc ggggtggtgc ccatcctggt cgagctggac    1980
ggcgacgtaa acggccacag gttcagcgtg tccggcgagg gcgagggcga tgccacctac    2040
ggcaagctga ccctgaagtt catctgcacc accggcaagc tgcccgtgcc ctggcccacc    2100
ctcgtgacca ccctgacctg gggcgtgcag tgcttcagcc gctaccccga ccacatgaag    2160
cagcacgact tcttcaagtc cgccatgccc gaaggctacg tccaggagcg taccatcttc    2220
```

-continued

```
ttcaaggacg acggcaacta caagacccgc gccgaggtga agttcgaggg cgacaccctg    2280
gtgaaccgca tcgagctgaa gggcatcggc ttcaaggagg acggcaacat cctggggcac    2340
aagctagagt acaactacat cagccacaac gtctatatca ccgccgacaa gcagaagaac    2400
ggcatcaagg cccacttcaa gatccgccac aacatcgagg acggcggcgt gcagctcgcc    2460
gaccactacc agcagaacac ccccatcggc gacggccccg tgctgctgcc cgacaaccac    2520
tacctgagca cccagtccgc cctgagcaaa gaccccaacg agaagcgcga tcacatggtc    2580
ctgctggagt tcgtgaccgc cgccgggatc actctcggca tggacgagct gtctagactg    2640
cagctgcctc tctggaacg cctgactctg gattaa                               2676
```

<210> SEQ ID NO 25
<211> LENGTH: 891
<212> TYPE: PRT
<213> ORGANISM: Artificial Sequence
<220> FEATURE:
<223> OTHER INFORMATION: A FRET biosensor of PKA

<400> SEQUENCE: 25

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Leu Leu
            35                  40                  45

Cys Thr Thr Gly Lys Leu Pro Val Pro Trp Pro Thr Leu Val Thr Thr
        50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Phe Lys Asp Pro Asn Glu Lys Arg Asp His Met Val Leu Leu Glu Phe
    210                 215                 220

Leu Thr Ala Ala Gly Ile Thr Glu Gly Met Asn Glu Leu Tyr Leu Glu
225                 230                 235                 240

Lys Phe Ser Gln Glu Gln Ile Gly Glu Asn Ile Val Cys Arg Val Ile
                245                 250                 255

Cys Thr Thr Gly Gln Ile Pro Ile Arg Asp Leu Ser Ala Asp Ile Ser
            260                 265                 270

Gln Val Leu Lys Glu Lys Arg Ser Ile Lys Lys Val Trp Thr Phe Gly
        275                 280                 285
```

```
Arg Asn Pro Ala Cys Asp Tyr His Leu Gly Asn Ile Ser Arg Leu Ser
    290                 295                 300

Asn Lys His Phe Gln Ile Leu Leu Gly Glu Asp Gly Asn Leu Leu Leu
305                 310                 315                 320

Asn Asp Ile Ser Thr Asn Gly Thr Trp Leu Asn Gly Gln Lys Val Glu
                325                 330                 335

Lys Asn Ser Asn Gln Leu Leu Ser Gln Gly Asp Glu Ile Thr Val Gly
                340                 345                 350

Val Gly Val Glu Ser Asp Ile Leu Ser Leu Val Ile Phe Ile Asn Asp
            355                 360                 365

Lys Phe Lys Gln Cys Leu Glu Gln Asn Lys Val Asp Arg Gly Thr Ser
370                 375                 380

Ala Gly Gly Ser Ala Gly Gly Ser Ala Gly Gly Ser Ala Gly Gly Ser
385                 390                 395                 400

Ala Gly Gly Ser Gly Ser Ala Gly Gly Ser Ala Gly Gly Ser Thr Ser
                405                 410                 415

Ala Gly Gly Ser Ala Gly Gly Ser Ala Gly Gly Ser Ala Gly Gly Ser
                420                 425                 430

Ala Gly Gly Ser Gly Ser Ala Gly Gly Ser Ala Gly Gly Ser Thr Ser
            435                 440                 445

Ala Gly Gly Ser Ala Gly Gly Ser Ala Gly Gly Ser Ala Gly Gly Ser
450                 455                 460

Ala Gly Gly Ser Gly Ser Ala Gly Gly Ser Ala Gly Gly Ser Thr Ser
465                 470                 475                 480

Ala Gly Gly Ser Ala Gly Gly Ser Ala Gly Gly Ser Ala Gly Gly Ser
                485                 490                 495

Ala Gly Gly Ser Gly Ser Ala Gly Gly Ser Ala Gly Gly Ser Thr Ser
                500                 505                 510

Ala Gly Gly Ser Ala Gly Gly Ser Ala Gly Gly Ser Ala Gly Gly Ser
            515                 520                 525

Ala Gly Gly Ser Gly Ser Ala Gly Gly Ser Ala Gly Gly Ser Thr Ser
530                 535                 540

Ala Gly Gly Ser Ala Gly Gly Ser Ala Gly Gly Ser Ala Gly Gly Ser
545                 550                 555                 560

Ala Gly Gly Ser Gly Ser Ala Gly Gly Ser Ala Gly Gly Ser Thr Ser
                565                 570                 575

Ala Gly Gly Ser Ala Gly Gly Ser Ala Gly Gly Ser Ala Gly Gly Ser
                580                 585                 590

Ala Gly Gly Ser Gly Ser Ala Gly Gly Ser Ala Gly Gly Ser Thr Ser
            595                 600                 605

Ala Gly Gly Ser Ala Gly Gly Ser Ala Gly Gly Ser Ala Gly Gly Ser
610                 615                 620

Ala Gly Gly Ser Gly Leu Arg Arg Ala Thr Leu Val Asp Gly Gly Arg
625                 630                 635                 640

Met Val Ser Lys Gly Glu Glu Leu Phe Thr Gly Val Val Pro Ile Leu
                645                 650                 655

Val Glu Leu Asp Gly Asp Val Asn Gly His Arg Phe Ser Val Ser Gly
                660                 665                 670

Glu Gly Glu Gly Asp Ala Thr Tyr Gly Lys Leu Thr Leu Lys Phe Ile
            675                 680                 685

Cys Thr Thr Gly Lys Leu Pro Val Pro Trp Pro Thr Leu Val Thr Thr
690                 695                 700
```

Leu Thr Trp Gly Val Gln Cys Phe Ser Arg Tyr Pro Asp His Met Lys
705                 710                 715                 720

Gln His Asp Phe Phe Lys Ser Ala Met Pro Glu Gly Tyr Val Gln Glu
            725                 730                 735

Arg Thr Ile Phe Phe Lys Asp Asp Gly Asn Tyr Lys Thr Arg Ala Glu
        740                 745                 750

Val Lys Phe Glu Gly Asp Thr Leu Val Asn Arg Ile Glu Leu Lys Gly
    755                 760                 765

Ile Gly Phe Lys Glu Asp Gly Asn Ile Leu Gly His Lys Leu Glu Tyr
770                 775                 780

Asn Tyr Ile Ser His Asn Val Tyr Ile Thr Ala Asp Lys Gln Lys Asn
785                 790                 795                 800

Gly Ile Lys Ala His Phe Lys Ile Arg His Asn Ile Glu Asp Gly Gly
            805                 810                 815

Val Gln Leu Ala Asp His Tyr Gln Gln Asn Thr Pro Ile Gly Asp Gly
        820                 825                 830

Pro Val Leu Leu Pro Asp Asn His Tyr Leu Ser Thr Gln Ser Ala Leu
    835                 840                 845

Ser Lys Asp Pro Asn Glu Lys Arg Asp His Met Val Leu Leu Glu Phe
850                 855                 860

Val Thr Ala Ala Gly Ile Thr Leu Gly Met Asp Glu Leu Ser Arg Leu
865                 870                 875                 880

Gln Leu Pro Pro Leu Glu Arg Leu Thr Leu Asp
            885                 890

<210> SEQ ID NO 26
<211> LENGTH: 244
<212> TYPE: PRT
<213> ORGANISM: Artificial Sequence
<220> FEATURE:
<223> OTHER INFORMATION: A 244 amino acid linker

<400> SEQUENCE: 26

Ser Ala Gly Gly Ser Ala Gly Gly Ser Ala Gly Gly Ser Ala Gly Gly
1               5                   10                  15

Ser Ala Gly Gly Ser Gly Ser Ala Gly Gly Ser Ala Gly Gly Ser Thr
            20                  25                  30

Ser Ala Gly Gly Ser Ala Gly Gly Ser Ala Gly Gly Ser Ala Gly Gly
        35                  40                  45

Ser Ala Gly Gly Ser Gly Ser Ala Gly Gly Ser Ala Gly Gly Ser Thr
    50                  55                  60

Ser Ala Gly Gly Ser Ala Gly Gly Ser Ala Gly Gly Ser Ala Gly Gly
65                  70                  75                  80

Ser Ala Gly Gly Ser Gly Ser Ala Gly Gly Ser Ala Gly Gly Ser Thr
            85                  90                  95

Ser Ala Gly Gly Ser Ala Gly Gly Ser Ala Gly Gly Ser Ala Gly Gly
        100                 105                 110

Ser Ala Gly Gly Ser Gly Ser Ala Gly Gly Ser Ala Gly Gly Ser Thr
    115                 120                 125

Ser Ala Gly Gly Ser Ala Gly Gly Ser Ala Gly Gly Ser Ala Gly Gly
130                 135                 140

Ser Ala Gly Gly Ser Gly Ser Ala Gly Gly Ser Ala Gly Gly Ser Thr
145                 150                 155                 160

Ser Ala Gly Gly Ser Ala Gly Gly Ser Ala Gly Gly Ser Ala Gly Gly
            165                 170                 175

```
Ser Ala Gly Gly Ser Gly Ser Ala Gly Gly Ser Ala Gly Gly Ser Thr
        180                 185                 190

Ser Ala Gly Gly Ser Ala Gly Gly Ser Ala Gly Gly Ser Ala Gly Gly
    195                 200                 205

Ser Ala Gly Gly Ser Gly Ser Ala Gly Gly Ser Ala Gly Gly Ser Thr
    210                 215                 220

Ser Ala Gly Gly Ser Ala Gly Gly Ser Ala Gly Gly Ser Ala Gly Gly
225                 230                 235                 240

Ser Ala Gly Gly

<210> SEQ ID NO 27
<211> LENGTH: 2667
<212> TYPE: DNA
<213> ORGANISM: Artificial Sequence
<220> FEATURE:
<223> OTHER INFORMATION: A FRET biosensor of Akt

<400> SEQUENCE: 27
```

| | | | | | |
|---|---|---|---|---|---|
| atgggaacgc | gtatgagcga | cgtggctatt | gtgaaggagg | gttggctgca | caaacgaggg | 60 |
| gagtacatca | agaccctggcg | gccacgctac | ttcctcctca | agaatgatgg | caccttcatt | 120 |
| ggctacaagg | agcgaccgca | ggatgtggac | caacgtgagg | ctccccctcaa | caacttctct | 180 |
| gtggcgcagt | gccagctgat | gaagacggag | cggccccggc | ccaacaccttt | catcatccgc | 240 |
| tgcctgcagt | ggaccactgt | catcgaacgc | accttccatg | tggagactcc | tgaggagcgg | 300 |
| gaggagtgga | caaccgccat | ccagactgtg | ctgacggcc | tcaagaagca | ggaggaggag | 360 |
| gagatggact | ccggtcgggg | ctcacccagt | gacaactcag | gggctgaaga | gatggaggtg | 420 |
| tccctggcca | gcccaagca | ccgcgtgacc | atggaattcg | gcatggtgag | caagggcgag | 480 |
| gagctgttca | ccggggtggt | gcccatcctg | gtcgagctgg | acggcgacgt | aaacggccac | 540 |
| aagttcagcg | tgtccggcga | gggcgagggc | gatgccacct | acggcaagct | gaccctgaag | 600 |
| cttctatgca | ccaccggcaa | gctgcccgtg | ccctggccca | ccctcgtgac | caccctgggc | 660 |
| tacggcctgc | agtgcttcgc | ccgctacccc | gaccacatga | agcagcacga | cttcttcaag | 720 |
| tccgccatgc | ccgaaggcta | cgtccaggag | cgcaccatct | tcttcaagga | cgacggcaac | 780 |
| tacaagaccc | gcgccgaggt | gaagttcgag | ggcgacaccc | tggtgaaccg | catcgagctg | 840 |
| aagggcatcg | acttcaagga | ggacggcaac | atcctggggc | acaagctgga | gtacaactac | 900 |
| aacagccaca | acgtctatat | caccgccgac | aagcagaaga | acggcatcaa | ggccaacttc | 960 |
| aagatccgcc | acaacatcga | ggacggcggc | gtgcagctcg | ccgaccacta | ccagcagaac | 1020 |
| acccccatcg | gcgacggccc | cgtgctgctg | cccgacaacc | actacctgag | ctaccagtcc | 1080 |
| gccctgttca | agacccccaa | cgagaagcgc | gatcacatgg | tcctgctgga | gttcctgacc | 1140 |
| gccgccggga | tcactgaggg | catgaacgag | ctgtacctcg | agaagttttc | tcaagaacag | 1200 |
| atcggcgaaa | acattgtgtg | cagggtcatt | tgtaccacgg | gtcaaattcc | catccgagat | 1260 |
| ttgtcagctg | atatttcaca | agtgcttaag | gaaaaacgat | ccataaagaa | agtttggaca | 1320 |
| tttggtagaa | acccagcctg | tgactatcat | ttaggaaaca | tttcaagact | gtcaaataag | 1380 |
| catttccaaa | tactactagg | agaagacggt | aaccttttat | tgaatgacat | ttccactaat | 1440 |
| gggacctggt | taaatgggca | aaaagtcgag | aagaacagca | atcagttact | gtcccaaggt | 1500 |
| gatgaaataa | ccgttggtgt | aggcgtggaa | tcagatattt | tatctctggt | cattttcata | 1560 |
| aacgacaaat | taagcagtg | cctggagcag | aacaaagttg | atcgcggtac | cagtgctggt | 1620 |
| ggtagtgctg | gtggtagtgc | tggtggtagt | gctggtggta | gtgctggtgg | ttccggcagt | 1680 |

```
gctggtggta gtgctggtgg tagtaccagt gctggtggta gtgctggtgg tagtgctggt    1740
ggtagtgctg gtggtagtgc tggtggttcc ggcagtgctg gtggtagtgc tggtggtagt    1800
accagtgctg gtggtagtgc tggtggtagt gctggtggta gtgctggtgg tagtgctggt    1860
ggttccggac gcaaaagaga tagattgggt actttaggtg atggcggccg catggtgagc    1920
aagggcgagg agctgttcac cggggtggtg cccatcctgg tcgagctgga cggcgacgta    1980
aacggccaca ggttcagcgt gtccggcgag ggcgagggcg atgccaccta cggcaagctg    2040
accctgaagt tcatctgcac caccggcaag ctgcccgtgc cctggcccac cctcgtgacc    2100
accctgacct gggcgtgca gtgcttcagc cgctaccccg accacatgaa gcagcacgac    2160
ttcttcaagt ccgccatgcc cgaaggctac gtccaggagc gtaccatctt cttcaaggac    2220
gacggcaact acaagacccg cgccgaggtg aagttcgagg gcgacaccct ggtgaaccgc    2280
atcgagctga agggcatcgg cttcaaggag gacggcaaca tcctgggcca caagctagag    2340
tacaactaca tcagccacaa cgtctatatc accgccgaca gcagaagaa cggcatcaag    2400 gcccacttca agatccgcca acatcgag gacgcggcg tgcagctcgc cgaccactac    2460
cagcagaaca cccccatcgg cgacggcccc gtgctgctgc ccgacaacca ctacctgagc    2520
acccagtccg ccctgagcaa agaccccaac gagaagcgcg atcacatggt cctgctggag    2580
ttcgtgaccg ccgccgggat cactctcggc atggacgagc tgtctagact gcagctgcct    2640
cctctggaac gcctgactct ggattaa                                         2667

<210> SEQ ID NO 28
<211> LENGTH: 888
<212> TYPE: PRT
<213> ORGANISM: Artificial Sequence
<220> FEATURE:
<223> OTHER INFORMATION: A FRET biosensor of Akt

<400> SEQUENCE: 28

Met Gly Thr Arg Met Ser Asp Val Ala Ile Val Lys Glu Gly Trp Leu
1               5                   10                  15

His Lys Arg Gly Glu Tyr Ile Lys Thr Trp Arg Pro Arg Tyr Phe Leu
            20                  25                  30

Leu Lys Asn Asp Gly Thr Phe Ile Gly Tyr Lys Glu Arg Pro Gln Asp
        35                  40                  45

Val Asp Gln Arg Glu Ala Pro Leu Asn Asn Phe Ser Val Ala Gln Cys
    50                  55                  60

Gln Leu Met Lys Thr Glu Arg Pro Arg Pro Asn Thr Phe Ile Ile Arg
65                  70                  75                  80

Cys Leu Gln Trp Thr Thr Val Ile Glu Arg Thr Phe His Val Glu Thr
                85                  90                  95

Pro Glu Glu Arg Glu Glu Trp Thr Thr Ala Ile Gln Thr Val Ala Asp
            100                 105                 110

Gly Leu Lys Lys Gln Glu Glu Glu Met Asp Phe Arg Ser Gly Ser
        115                 120                 125

Pro Ser Asp Asn Ser Gly Ala Glu Glu Met Glu Val Ser Leu Ala Lys
    130                 135                 140

Pro Lys His Arg Val Thr Met Glu Phe Gly Met Val Ser Lys Gly Glu
145                 150                 155                 160

Glu Leu Phe Thr Gly Val Val Pro Ile Leu Val Glu Leu Asp Gly Asp
                165                 170                 175

Val Asn Gly His Lys Phe Ser Val Ser Gly Glu Gly Glu Gly Asp Ala
```

```
                180               185               190
Thr Tyr Gly Lys Leu Thr Leu Lys Leu Leu Cys Thr Thr Gly Lys Leu
            195               200               205
Pro Val Pro Trp Pro Thr Leu Val Thr Thr Leu Gly Tyr Gly Leu Gln
210               215               220
Cys Phe Ala Arg Tyr Pro Asp His Met Lys Gln His Asp Phe Phe Lys
225               230               235               240
Ser Ala Met Pro Glu Gly Tyr Val Gln Glu Arg Thr Ile Phe Phe Lys
            245               250               255
Asp Asp Gly Asn Tyr Lys Thr Arg Ala Glu Val Lys Phe Glu Gly Asp
            260               265               270
Thr Leu Val Asn Arg Ile Glu Leu Lys Gly Ile Asp Phe Lys Glu Asp
            275               280               285
Gly Asn Ile Leu Gly His Lys Leu Glu Tyr Asn Tyr Asn Ser His Asn
            290               295               300
Val Tyr Ile Thr Ala Asp Lys Gln Lys Asn Gly Ile Lys Ala Asn Phe
305               310               315               320
Lys Ile Arg His Asn Ile Glu Asp Gly Gly Val Gln Leu Ala Asp His
            325               330               335
Tyr Gln Gln Asn Thr Pro Ile Gly Asp Gly Pro Val Leu Leu Pro Asp
            340               345               350
Asn His Tyr Leu Ser Tyr Gln Ser Ala Leu Phe Lys Asp Pro Asn Glu
            355               360               365
Lys Arg Asp His Met Val Leu Leu Glu Phe Leu Thr Ala Ala Gly Ile
            370               375               380
Thr Glu Gly Met Asn Glu Leu Tyr Leu Glu Lys Phe Ser Gln Glu Gln
385               390               395               400
Ile Gly Glu Asn Ile Val Cys Arg Val Ile Cys Thr Thr Gly Gln Ile
            405               410               415
Pro Ile Arg Asp Leu Ser Ala Asp Ile Ser Gln Val Leu Lys Glu Lys
            420               425               430
Arg Ser Ile Lys Lys Val Trp Thr Phe Gly Arg Asn Pro Ala Cys Asp
            435               440               445
Tyr His Leu Gly Asn Ile Ser Arg Leu Ser Asn Lys His Phe Gln Ile
            450               455               460
Leu Leu Gly Glu Asp Gly Asn Leu Leu Leu Asn Asp Ile Ser Thr Asn
465               470               475               480
Gly Thr Trp Leu Asn Gly Gln Lys Val Glu Lys Asn Ser Asn Gln Leu
            485               490               495
Leu Ser Gln Gly Asp Glu Ile Thr Val Gly Val Gly Val Glu Ser Asp
            500               505               510
Ile Leu Ser Leu Val Ile Phe Ile Asn Asp Lys Phe Lys Gln Cys Leu
            515               520               525
Glu Gln Asn Lys Val Asp Arg Gly Thr Ser Ala Gly Gly Ser Ala Gly
            530               535               540
Gly Ser Ala Gly Gly Ser Ala Gly Gly Ser Ala Gly Gly Ser Gly Ser
545               550               555               560
Ala Gly Gly Ser Ala Gly Gly Ser Thr Ser Ala Gly Gly Ser Ala Gly
            565               570               575
Gly Ser Ala Gly Gly Ser Ala Gly Gly Ser Ala Gly Gly Ser Gly Ser
            580               585               590
Ala Gly Gly Ser Ala Gly Gly Ser Thr Ser Ala Gly Gly Ser Ala Gly
            595               600               605
```

Gly Ser Ala Gly Gly Ser Ala Gly Gly Ser Gly Arg
            610             615             620

Lys Arg Asp Arg Leu Gly Thr Leu Gly Asp Gly Gly Arg Met Val Ser
625             630             635             640

Lys Gly Glu Glu Leu Phe Thr Gly Val Val Pro Ile Leu Val Glu Leu
            645             650             655

Asp Gly Asp Val Asn Gly His Arg Phe Ser Val Ser Gly Glu Gly Glu
            660             665             670

Gly Asp Ala Thr Tyr Gly Lys Leu Thr Leu Lys Phe Ile Cys Thr Thr
            675             680             685

Gly Lys Leu Pro Val Pro Trp Pro Thr Leu Val Thr Thr Leu Thr Trp
            690             695             700

Gly Val Gln Cys Phe Ser Arg Tyr Pro Asp His Met Lys Gln His Asp
705             710             715             720

Phe Phe Lys Ser Ala Met Pro Glu Gly Tyr Val Gln Glu Arg Thr Ile
            725             730             735

Phe Phe Lys Asp Asp Gly Asn Tyr Lys Thr Arg Ala Glu Val Lys Phe
            740             745             750

Glu Gly Asp Thr Leu Val Asn Arg Ile Glu Leu Lys Gly Ile Gly Phe
            755             760             765

Lys Glu Asp Gly Asn Ile Leu Gly His Lys Leu Glu Tyr Asn Tyr Ile
770             775             780

Ser His Asn Val Tyr Ile Thr Ala Asp Lys Gln Lys Asn Gly Ile Lys
785             790             795             800

Ala His Phe Lys Ile Arg His Asn Ile Glu Asp Gly Gly Val Gln Leu
            805             810             815

Ala Asp His Tyr Gln Gln Asn Thr Pro Ile Gly Asp Gly Pro Val Leu
            820             825             830

Leu Pro Asp Asn His Tyr Leu Ser Thr Gln Ser Ala Leu Ser Lys Asp
            835             840             845

Pro Asn Glu Lys Arg Asp His Met Val Leu Leu Glu Phe Val Thr Ala
850             855             860

Ala Gly Ile Thr Leu Gly Met Asp Glu Leu Ser Arg Leu Gln Leu Pro
865             870             875             880

Pro Leu Glu Arg Leu Thr Leu Asp
            885

<210> SEQ ID NO 29
<211> LENGTH: 2763
<212> TYPE: DNA
<213> ORGANISM: Artificial Sequence
<220> FEATURE:
<223> OTHER INFORMATION: A FRET biosensor of Akt

<400> SEQUENCE: 29
atgggaacgc gtatgagcga cgtggctatt gtgaaggagg gttggctgca caaacgaggg    60
gagtacatca agacctggcg gccacgctac ttcctcctca gaatgatgg cacctcatt    120 ggctacaagg agcgaccgca ggatgtggac aacgtgagg ctcccctcaa caacttctct    180
gtggcgcagt gccagctgat gaagacggag cggccccggc ccaacacctt catcatccgc    240
tgcctgcagt ggaccactgt catcgaacgc accttccatg tggagactcc tgaggagcgg    300
gaggagtgga caaccgccat ccagactgtg gctgacggcc tcaagaagca ggaggaggag    360
gagatggact tccggtcggg ctcacccagt gacaactcag gggctgaaga gatggaggtg    420

```
tccctggcca agcccaagca ccgcgtgacc atggaattcg gcatggtgag caagggcgag    480
gagctgttca ccggggtggt gcccatcctg gtcgagctgg acggcgacgt aaacggccac    540
aagttcagcg tgtccggcga gggcgagggc gatgccacct acggcaagct gaccctgaag    600
cttctatgca ccaccggcaa gctgcccgtg ccctggccca ccctcgtgac cacccctggg    660
tacggcctgc agtgcttcgc ccgctacccc gaccacatga gcagcacga cttcttcaag    720
tccgccatgc ccgaaggcta cgtccaggag cgcaccatct tcttcaagga cgacggcaac    780
tacaagaccc gcgccgaggt gaagttcgag ggcgacaccc tggtgaaccg catcgagctg    840
aagggcatcg acttcaagga ggacggcaac atcctgggc acaagctgga gtacaactac    900
aacagccaca acgtctatat caccgccgac aagcagaaga cggcatcaa ggccaacttc    960
aagatccgcc acaacatcga ggacggcggc gtgcagctcg ccgaccacta ccagcagaac   1020
acccccatcg gcgacggccc cgtgctgctg cccgacaacc actacctgag ctaccagtcc   1080
gccctgttca agacccccaa cgagaagcgc gatcacatgg tcctgctgga gttcctgacc   1140
gccgccggga tcactgaggg catgaacgag ctgtacctcg agaagttttc tcaagaacag   1200
atcggcgaaa acattgtgtg cagggtcatt tgtaccacgg gtcaaattcc catccgagat   1260
ttgtcagctg atatttcaca agtgcttaag gaaaaacgat ccataaagaa agtttggaca   1320
tttggtagaa acccagcctg tgactatcat ttaggaaaca tttcaagact gtcaaataag   1380
catttccaaa tactactagg agaagacggt aacctttat tgaatgacat ttccactaat   1440
gggacctggt taaatgggca aaaagtcgag aagaacagca atcagttact gtcccaaggt   1500
gatgaaataa ccgttggtgt aggcgtggaa tcagatattt tatctctggt cattttcata   1560
aacgacaaat ttaagcagtg cctggagcag aacaaagttg atcgcggtac cagtgctggt   1620
ggtagtgctg gtggtagtgc tggtggtagt gctggtggta gtgctggtgg ttccggcagt   1680
gctggtggta gtgctggtgg tagtaccagt gctggtggta gtgctggtgg tagtgctggt   1740
ggtagtgctg gtggtagtgc tggtggttcc ggcagtgctg gtggtagtgc tggtggtagt   1800
accagtgctg gtggtagtgc tggtggtagt gctggtggta gtgctggtgg tagtgctggt   1860
ggttccggca gtgctggtgg tagtgctggt ggtagtacca gtgctggtgg tagtgctggt   1920
ggtagtgctg gtggtagtgc tggtggtagt gctggtggtt ccggacgcaa aagagataga   1980
ttgggtactt taggtgatgg cggccgcatg gtgagcaagg gcgaggagct gttcaccggg   2040
gtggtgccca tcctggtcga gctggacggc gacgtaaacg ccacaggtt cagcgtgtcc   2100
ggcgagggcg agggcgatgc cacctacggc aagctgaccc tgaagttcat ctgcaccacc   2160
ggcaagctgc ccgtgccctg gcccaccctc gtgaccaccc tgacctgggg cgtgcagtgc   2220
ttcagccgct accccgacca catgaagcag cacgacttct tcaagtccgc catgcccgaa   2280
ggctacgtcc aggagcgtac catcttcttc aaggacgacg caactacaa gacccgcgcc   2340
gaggtgaagt tcgagggcga caccctggtg aaccgcatcg agctgaaggg catcggcttc   2400
aaggaggacg gcaacatcct ggggcacaag ctagagtaca actacatcag ccacaacgtc   2460
tatatcaccg ccgacaagca gaagaacggc atcaaggccc acttcaagat ccgccacaac   2520
atcgaggacg gcgcgtgca gctcgccgac cactaccagc agaacacccc catcggcgac   2580
ggccccgtgc tgctgcccga caaccactac ctgagcaccc agtccgccct gagcaaagac   2640
cccaacgaga gcgcgatca catggtcctg ctggagttcg tgaccgccgc cgggatcact   2700
ctcggcatga acgagctgtc tagactgcag ctgcctcctc tggaacgcct gactctggat   2760
taa                                                                  2763
```

<210> SEQ ID NO 30
<211> LENGTH: 920
<212> TYPE: PRT
<213> ORGANISM: Artificial Sequence
<220> FEATURE:
<223> OTHER INFORMATION: A FRET biosensor of Akt

<400> SEQUENCE: 30

```
Met Gly Thr Arg Met Ser Asp Val Ala Ile Val Lys Glu Gly Trp Leu
1               5                   10                  15

His Lys Arg Gly Glu Tyr Ile Lys Thr Trp Arg Pro Arg Tyr Phe Leu
                20                  25                  30

Leu Lys Asn Asp Gly Thr Phe Ile Gly Tyr Lys Glu Arg Pro Gln Asp
            35                  40                  45

Val Asp Gln Arg Glu Ala Pro Leu Asn Asn Phe Ser Val Ala Gln Cys
    50                  55                  60

Gln Leu Met Lys Thr Glu Arg Pro Arg Pro Asn Thr Phe Ile Ile Arg
65                  70                  75                  80

Cys Leu Gln Trp Thr Thr Val Ile Glu Arg Thr Phe His Val Glu Thr
                85                  90                  95

Pro Glu Glu Arg Glu Glu Trp Thr Thr Ala Ile Gln Thr Val Ala Asp
                100                 105                 110

Gly Leu Lys Lys Gln Glu Glu Glu Met Asp Phe Arg Ser Gly Ser
            115                 120                 125

Pro Ser Asp Asn Ser Gly Ala Glu Glu Met Glu Val Ser Leu Ala Lys
    130                 135                 140

Pro Lys His Arg Val Thr Met Glu Phe Gly Met Val Ser Lys Gly Glu
145                 150                 155                 160

Glu Leu Phe Thr Gly Val Val Pro Ile Leu Val Glu Leu Asp Gly Asp
                165                 170                 175

Val Asn Gly His Lys Phe Ser Val Ser Gly Glu Gly Glu Gly Asp Ala
                180                 185                 190

Thr Tyr Gly Lys Leu Thr Leu Lys Leu Leu Cys Thr Thr Gly Lys Leu
            195                 200                 205

Pro Val Pro Trp Pro Thr Leu Val Thr Thr Leu Gly Tyr Gly Leu Gln
    210                 215                 220

Cys Phe Ala Arg Tyr Pro Asp His Met Lys Gln His Asp Phe Phe Lys
225                 230                 235                 240

Ser Ala Met Pro Glu Gly Tyr Val Gln Glu Arg Thr Ile Phe Phe Lys
                245                 250                 255

Asp Asp Gly Asn Tyr Lys Thr Arg Ala Glu Val Lys Phe Glu Gly Asp
                260                 265                 270

Thr Leu Val Asn Arg Ile Glu Leu Lys Gly Ile Asp Phe Lys Glu Asp
            275                 280                 285

Gly Asn Ile Leu Gly His Lys Leu Glu Tyr Asn Tyr Asn Ser His Asn
    290                 295                 300

Val Tyr Ile Thr Ala Asp Lys Gln Lys Asn Gly Ile Lys Ala Asn Phe
305                 310                 315                 320

Lys Ile Arg His Asn Ile Glu Asp Gly Val Gln Leu Ala Asp His
                325                 330                 335

Tyr Gln Gln Asn Thr Pro Ile Gly Asp Gly Pro Val Leu Leu Pro Asp
                340                 345                 350

Asn His Tyr Leu Ser Tyr Gln Ser Ala Leu Phe Lys Asp Pro Asn Glu
            355                 360                 365
```

```
Lys Arg Asp His Met Val Leu Leu Glu Phe Leu Thr Ala Ala Gly Ile
    370                 375                 380

Thr Glu Gly Met Asn Glu Leu Tyr Leu Glu Lys Phe Ser Gln Glu Gln
385                 390                 395                 400

Ile Gly Glu Asn Ile Val Cys Arg Val Ile Cys Thr Thr Gly Gln Ile
                405                 410                 415

Pro Ile Arg Asp Leu Ser Ala Asp Ile Ser Gln Val Leu Lys Glu Lys
                420                 425                 430

Arg Ser Ile Lys Lys Val Trp Thr Phe Gly Arg Asn Pro Ala Cys Asp
            435                 440                 445

Tyr His Leu Gly Asn Ile Ser Arg Leu Ser Asn Lys His Phe Gln Ile
    450                 455                 460

Leu Leu Gly Glu Asp Gly Asn Leu Leu Leu Asn Asp Ile Ser Thr Asn
465                 470                 475                 480

Gly Thr Trp Leu Asn Gly Gln Lys Val Glu Lys Asn Ser Asn Gln Leu
                485                 490                 495

Leu Ser Gln Gly Asp Glu Ile Thr Val Gly Val Gly Val Glu Ser Asp
                500                 505                 510

Ile Leu Ser Leu Val Ile Phe Ile Asn Asp Lys Phe Lys Gln Cys Leu
            515                 520                 525

Glu Gln Asn Lys Val Asp Arg Gly Thr Ser Ala Gly Gly Ser Ala Gly
    530                 535                 540

Gly Ser Ala Gly Gly Ser Ala Gly Gly Ser Ala Gly Gly Ser Gly Ser
545                 550                 555                 560

Ala Gly Gly Ser Ala Gly Gly Ser Thr Ser Ala Gly Gly Ser Ala Gly
                565                 570                 575

Gly Ser Ala Gly Gly Ser Ala Gly Gly Ser Ala Gly Gly Ser Gly Ser
                580                 585                 590

Ala Gly Gly Ser Ala Gly Gly Ser Thr Ser Ala Gly Gly Ser Ala Gly
            595                 600                 605

Gly Ser Ala Gly Gly Ser Ala Gly Gly Ser Ala Gly Gly Ser Gly Ser
    610                 615                 620

Ala Gly Gly Ser Ala Gly Gly Ser Thr Ser Ala Gly Gly Ser Ala Gly
625                 630                 635                 640

Gly Ser Ala Gly Gly Ser Ala Gly Gly Ser Ala Gly Gly Ser Gly Arg
                645                 650                 655

Lys Arg Asp Arg Leu Gly Thr Leu Gly Asp Gly Gly Arg Met Val Ser
                660                 665                 670

Lys Gly Glu Glu Leu Phe Thr Gly Val Val Pro Ile Leu Val Glu Leu
            675                 680                 685

Asp Gly Asp Val Asn Gly His Arg Phe Ser Val Ser Gly Glu Gly Glu
    690                 695                 700

Gly Asp Ala Thr Tyr Gly Lys Leu Thr Leu Lys Phe Ile Cys Thr Thr
705                 710                 715                 720

Gly Lys Leu Pro Val Pro Trp Pro Thr Leu Val Thr Thr Leu Thr Trp
                725                 730                 735

Gly Val Gln Cys Phe Ser Arg Tyr Pro Asp His Met Lys Gln His Asp
                740                 745                 750

Phe Phe Lys Ser Ala Met Pro Glu Gly Tyr Val Gln Glu Arg Thr Ile
            755                 760                 765

Phe Phe Lys Asp Asp Gly Asn Tyr Lys Thr Arg Ala Glu Val Lys Phe
    770                 775                 780
```

| | | | | | | | | | | | |
|---|---|---|---|---|---|---|---|---|---|---|---|
|Glu|Gly|Asp|Thr|Leu|Val|Asn|Arg|Ile|Glu|Leu|Lys|Gly|Ile|Gly|Phe|
|785| | | |790| | | |795| | | |800| | | |

Lys Glu Asp Gly Asn Ile Leu Gly His Lys Leu Glu Tyr Asn Tyr Ile
            805                 810                 815

Ser His Asn Val Tyr Ile Thr Ala Asp Lys Gln Lys Asn Gly Ile Lys
            820                 825                 830

Ala His Phe Lys Ile Arg His Asn Ile Glu Asp Gly Gly Val Gln Leu
            835                 840                 845

Ala Asp His Tyr Gln Gln Asn Thr Pro Ile Gly Asp Gly Pro Val Leu
        850                 855                 860

Leu Pro Asp Asn His Tyr Leu Ser Thr Gln Ser Ala Leu Ser Lys Asp
865                 870                 875                 880

Pro Asn Glu Lys Arg Asp His Met Val Leu Leu Glu Phe Val Thr Ala
            885                 890                 895

Ala Gly Ile Thr Leu Gly Met Asp Glu Leu Ser Arg Leu Gln Leu Pro
            900                 905                 910

Pro Leu Glu Arg Leu Thr Leu Asp
            915                 920

<210> SEQ ID NO 31
<211> LENGTH: 2043
<212> TYPE: DNA
<213> ORGANISM: Artificial Sequence
<220> FEATURE:
<223> OTHER INFORMATION: A FRET biosensor of ERK

<400> SEQUENCE: 31

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct ctatgcacc accggcaagc tgcccgtgcc ctggcccacc     180
ctcgtgacca ccctgggcta cggcctgcag tgcttcgccc gctacccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca ccgccgacaa gcagaagaac     480
ggcatcaagg ccaacttcaa gatccgccac aacatcgagg acggcggcgt gcagctcgcc     540
gaccactacc agcagaacac ccccatcggc gacggccccg tgctgctgcc cgacaaccac     600
tacctgagct accagtccgc cctgttcaaa gaccccaacg agaagcgcga tcacatggtc     660
ctgctggagt tcctgaccgc cgccgggatc actgagggca tgaacgagct gtacctcgag     720
atggcggaca ggagaagct gccgcccggc tgggagaagc gcatgagccg cagctcaggc     780
cgagtgtact acttcaacca catcactaac gccagccagt gggagcggcc cagcggcaac     840
agcagcagtg gtggcaaaaa cgggcagggg gagcctgcca gggtaccag tgctggtggt     900
agtgctggtg gtagtgctgg tggtagtgct ggtggtagtg ctggtggttc cggcagtgct     960
ggtggtagtg ctggtggtag taccagtgct ggtggtagtg ctggtggtag tgctggtggt    1020
agtgctggtg gtagtgctgg tggttccggc agtgctggtg gtagtgctgg tggtagtacc    1080
agtgctggtg gtagtgctgg tggtagtgct ggtggtagtg ctggtggtag tgctggtggt    1140
tccggcagtg ctggtggtag tgctggtggt agtaccagtg ctggtggtag tgctggtggt    1200
agtgctggtg gtagtgctgg tggtagtgct ggtggttccg gaccagatgt ccctagaact    1260
```

```
ccagtgggca aaggcggccg catggtgagc aagggcgagg agctgttcac cggggtggtg    1320
cccatcctgg tcgagctgga cggcgacgta aacggccaca agttcagcgt gtccggcgag    1380
ggcgagggcg atgccaccta cggcaagctg accctgaagt tcatctgcac caccggcaag    1440
ctgcccgtgc cctggcccac cctcgtgacc accctgacct ggggcgtgca gtgcttcagc    1500 cgctacccccg accacatgaa gcagcacgac ttcttcaagt ccgccatgcc cgaaggctac    1560
gtccaggagc gcaccatctt cttcaaggac gacggcaact acaagacccg cgccgaggtg    1620
aagttcgagg gcgacaccct ggtgaaccgc atcgagctga agggcatcga cttcaaggag    1680
gacggcaaca tcctggggca caagctggag tacaactaca tcagccacaa cgtctatatc    1740
accgccgaca agcagaagaa cggcatcaag gccaacttca agatccgcca caacatcgag    1800
gacggcagcg tgcagctcgc cgaccactac cagcagaaca cccccatcgg cgacggcccc    1860
gtgctgctgc ccgacaacca ctacttgagc acccagtccg ccctgagcaa agaccccaac    1920
gagaagcgcg atcacatggt cctgctggag ttcgtgaccg ccgccgggat cactctcggc    1980
atggacgagc tgggccgctc tagactgcag ctgcctcctc tggaacgcct gactctggat    2040
taa                                                                  2043
```

<210> SEQ ID NO 32
<211> LENGTH: 680
<212> TYPE: PRT
<213> ORGANISM: Artificial Sequence
<220> FEATURE:
<223> OTHER INFORMATION: A FRET biosensor of ERK

<400> SEQUENCE: 32

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Leu
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Phe Lys Asp Pro Asn Glu Lys Arg Asp His Met Val Leu Leu Glu Phe
    210                 215                 220
```

```
Leu Thr Ala Ala Gly Ile Thr Glu Gly Met Asn Glu Leu Tyr Leu Glu
225                 230                 235                 240

Met Ala Asp Glu Glu Lys Leu Pro Pro Gly Trp Glu Lys Arg Met Ser
            245                 250                 255

Arg Ser Ser Gly Arg Val Tyr Tyr Phe Asn His Ile Thr Asn Ala Ser
        260                 265                 270

Gln Trp Glu Arg Pro Ser Gly Asn Ser Ser Gly Gly Lys Asn Gly
    275                 280                 285

Gln Gly Glu Pro Ala Arg Gly Thr Ser Ala Gly Ser Ala Gly Gly
290                 295                 300

Ser Ala Gly Gly Ser Ala Gly Gly Ser Ala Gly Gly Ser Gly Ser Ala
305                 310                 315                 320

Gly Gly Ser Ala Gly Gly Ser Thr Ser Ala Gly Gly Ser Ala Gly Gly
                325                 330                 335

Ser Ala Gly Gly Ser Ala Gly Gly Ser Ala Gly Gly Ser Gly Ser Ala
                340                 345                 350

Gly Gly Ser Ala Gly Gly Ser Thr Ser Ala Gly Gly Ser Ala Gly Gly
            355                 360                 365

Ser Ala Gly Gly Ser Ala Gly Gly Ser Ala Gly Gly Ser Gly Ser Ala
        370                 375                 380

Gly Gly Ser Ala Gly Gly Ser Thr Ser Ala Gly Gly Ser Ala Gly Gly
385                 390                 395                 400

Ser Ala Gly Gly Ser Ala Gly Gly Ser Ala Gly Gly Ser Gly Pro Asp
                405                 410                 415

Val Pro Arg Thr Pro Val Gly Lys Gly Gly Arg Met Val Ser Lys Gly
                420                 425                 430

Glu Glu Leu Phe Thr Gly Val Val Pro Ile Leu Val Glu Leu Asp Gly
            435                 440                 445

Asp Val Asn Gly His Lys Phe Ser Val Ser Gly Glu Gly Glu Gly Asp
        450                 455                 460

Ala Thr Tyr Gly Lys Leu Thr Leu Lys Phe Ile Cys Thr Thr Gly Lys
465                 470                 475                 480

Leu Pro Val Pro Trp Pro Thr Leu Val Thr Thr Leu Thr Trp Gly Val
                485                 490                 495

Gln Cys Phe Ser Arg Tyr Pro Asp His Met Lys Gln His Asp Phe Phe
                500                 505                 510

Lys Ser Ala Met Pro Glu Gly Tyr Val Gln Glu Arg Thr Ile Phe Phe
            515                 520                 525

Lys Asp Asp Gly Asn Tyr Lys Thr Arg Ala Glu Val Lys Phe Glu Gly
        530                 535                 540

Asp Thr Leu Val Asn Arg Ile Glu Leu Lys Gly Ile Asp Phe Lys Glu
545                 550                 555                 560

Asp Gly Asn Ile Leu Gly His Lys Leu Glu Tyr Asn Tyr Ile Ser His
                565                 570                 575

Asn Val Tyr Ile Thr Ala Asp Lys Gln Lys Asn Gly Ile Lys Ala Asn
                580                 585                 590

Phe Lys Ile Arg His Asn Ile Glu Asp Gly Ser Val Gln Leu Ala Asp
            595                 600                 605

His Tyr Gln Gln Asn Thr Pro Ile Gly Asp Gly Pro Val Leu Leu Pro
        610                 615                 620

Asp Asn His Tyr Leu Ser Thr Gln Ser Ala Leu Ser Lys Asp Pro Asn
625                 630                 635                 640
```

```
Glu Lys Arg Asp His Met Val Leu Leu Glu Phe Val Thr Ala Ala Gly
            645                 650                 655

Ile Thr Leu Gly Met Asp Glu Leu Gly Arg Ser Arg Leu Gln Leu Pro
            660                 665                 670

Pro Leu Glu Arg Leu Thr Leu Asp
            675             680

<210> SEQ ID NO 33
<211> LENGTH: 2067
<212> TYPE: DNA
<213> ORGANISM: Artificial Sequence
<220> FEATURE:
<223> OTHER INFORMATION: A FRET biosensor of ERK

<400> SEQUENCE: 33
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct ctatgcacc accggcaagc tgcccgtgcc ctggcccacc     180
ctcgtgacca ccctgggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca ccgccgacaa gcagaagaac     480
ggcatcaagg ccaacttcaa gatccgccac aacatcgagg acggcggcgt gcagctcgcc     540
gaccactacc agcagaacac ccccatcggc gacggccccg tgctgctgcc cgacaaccac     600
tacctgagct accagtccgc cctgttcaaa gaccccaacg agaagcgcga tcacatggtc     660
ctgctggagt tcctgaccgc cgccgggatc actgagggca tgaacgagct gtacctcgag     720
atggcggacg aggagaagct gccgcccggc tgggagaagc gcatgagccg cagctcaggc     780
cgagtgtact acttcaacca catcactaac gccagccagt gggagcggcc cagcggcaac     840
agcagcagtg gtggcaaaaa cgggcagggg gagcctgcca ggggtaccag tgctggtggt     900
agtgctggtg gtagtgctgg tggtagtgct ggtggttc cggcagtgct     960
ggtggtagtg ctggtggtag taccagtgct ggtggtagtg ctggtggtag tgctggtggt    1020
agtgctggtg gtagtgctgg tggttccggc agtgctggtg gtagtgctgg tggtagtacc    1080
agtgctggtg gtagtgctgg tggtagtgct ggtggtagtg ctggtggtag tgctggtggt    1140
tccggcagtg ctggtggtag tgctggtggt agtaccagtg ctggtggtag tgctggtggt    1200
agtgctggtg gtagtgctgg tggtagtgct ggtggttccg gaccagatgt ccctagaact    1260
ccagtggata aagcaaagct gtcattccaa tttccgggcg gccgcatggt gagcaagggc    1320
gaggagctgt tcaccggggt ggtgcccatc ctggtcgagc tggacggcga cgtaaacggc    1380
cacaagttca gcgtgtccgg cgagggcgag ggcgatgcca cctacggcaa gctgaccctg    1440
aagttcatct gcaccaccgg caagctgccc gtgccctggc ccaccctcgt gaccaccctg    1500
acctggggcg tgcagtgctt cagccgctac cccgaccaca tgaagcagca cgacttcttc    1560
aagtccgcca tgcccgaagg ctacgtccag gagcgcacca tcttcttcaa ggacgacggc    1620
aactacaaga cccgcgccga ggtgaagttc gagggcgaca ccctggtgaa ccgcatcgag    1680
ctgaagggca tcgacttcaa ggaggacggc aacatcctgg ggcacaagct ggagtacaac    1740
tacatcagcc acaacgtcta tatcaccgcc gacaagcaga agaacggcat caaggccaac    1800
```

-continued

```
ttcaagatcc gccacaacat cgaggacggc agcgtgcagc tcgccgacca ctaccagcag   1860
aacaccccca tcggcgacgg ccccgtgctg ctgcccgaca accactactt gagcacccag   1920
tccgccctga gcaaagaccc caacgagaag cgcgatcaca tggtcctgct ggagttcgtg   1980
accgccgccg ggatcactct cggcatggac gagctgggcc gctctagact gcagctgcct   2040
cctctggaac gcctgactct ggattaa                                      2067
```

<210> SEQ ID NO 34
<211> LENGTH: 688
<212> TYPE: PRT
<213> ORGANISM: Artificial Sequence
<220> FEATURE:
<223> OTHER INFORMATION: A FRET biosensor of ERK

<400> SEQUENCE: 34

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Leu
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Phe Lys Asp Pro Asn Glu Lys Arg Asp His Met Val Leu Leu Glu Phe
    210                 215                 220

Leu Thr Ala Ala Gly Ile Thr Glu Gly Met Asn Glu Leu Tyr Leu Glu
225                 230                 235                 240

Met Ala Asp Glu Glu Lys Leu Pro Pro Gly Trp Glu Lys Arg Met Ser
                245                 250                 255

Arg Ser Ser Gly Arg Val Tyr Tyr Phe Asn His Ile Thr Asn Ala Ser
            260                 265                 270

Gln Trp Glu Arg Pro Ser Gly Asn Ser Ser Gly Gly Lys Asn Gly
        275                 280                 285

Gln Gly Glu Pro Ala Arg Gly Thr Ser Ala Gly Gly Ser Ala Gly Gly
    290                 295                 300

Ser Ala Gly Gly Ser Ala Gly Gly Ser Ala Gly Gly Ser Gly Ser Ala
305                 310                 315                 320
```

Gly Gly Ser Ala Gly Gly Ser Thr Ser Ala Gly Gly Ser Ala Gly Gly
                    325                 330                 335

Ser Ala Gly Gly Ser Ala Gly Gly Ser Ala Gly Gly Ser Gly Ser Ala
                340                 345                 350

Gly Gly Ser Ala Gly Gly Ser Thr Ser Ala Gly Gly Ser Ala Gly Gly
                355                 360                 365

Ser Ala Gly Gly Ser Ala Gly Gly Ser Ala Gly Gly Ser Gly Ser Ala
                370                 375                 380

Gly Gly Ser Ala Gly Gly Ser Thr Ser Ala Gly Gly Ser Ala Gly Gly
385                 390                 395                 400

Ser Ala Gly Gly Ser Ala Gly Gly Ser Ala Gly Gly Ser Gly Pro Asp
                405                 410                 415

Val Pro Arg Thr Pro Val Asp Lys Ala Lys Leu Ser Phe Gln Phe Pro
                420                 425                 430

Gly Gly Arg Met Val Ser Lys Gly Glu Glu Leu Phe Thr Gly Val Val
                435                 440                 445

Pro Ile Leu Val Glu Leu Asp Gly Asp Val Asn Gly His Lys Phe Ser
                450                 455                 460

Val Ser Gly Glu Gly Glu Gly Asp Ala Thr Tyr Gly Lys Leu Thr Leu
465                 470                 475                 480

Lys Phe Ile Cys Thr Thr Gly Lys Leu Pro Val Pro Trp Pro Thr Leu
                485                 490                 495

Val Thr Thr Leu Thr Trp Gly Val Gln Cys Phe Ser Arg Tyr Pro Asp
                500                 505                 510

His Met Lys Gln His Asp Phe Phe Lys Ser Ala Met Pro Glu Gly Tyr
                515                 520                 525

Val Gln Glu Arg Thr Ile Phe Phe Lys Asp Asp Gly Asn Tyr Lys Thr
                530                 535                 540

Arg Ala Glu Val Lys Phe Glu Gly Asp Thr Leu Val Asn Arg Ile Glu
545                 550                 555                 560

Leu Lys Gly Ile Asp Phe Lys Glu Asp Gly Asn Ile Leu Gly His Lys
                565                 570                 575

Leu Glu Tyr Asn Tyr Ile Ser His Asn Val Tyr Ile Thr Ala Asp Lys
                580                 585                 590

Gln Lys Asn Gly Ile Lys Ala Asn Phe Lys Ile Arg His Asn Ile Glu
                595                 600                 605

Asp Gly Ser Val Gln Leu Ala Asp His Tyr Gln Gln Asn Thr Pro Ile
                610                 615                 620

Gly Asp Gly Pro Val Leu Leu Pro Asp Asn His Tyr Leu Ser Thr Gln
625                 630                 635                 640

Ser Ala Leu Ser Lys Asp Pro Asn Glu Lys Arg Asp His Met Val Leu
                645                 650                 655

Leu Glu Phe Val Thr Ala Ala Gly Ile Thr Leu Gly Met Asp Glu Leu
                660                 665                 670

Gly Arg Ser Arg Leu Gln Leu Pro Pro Leu Glu Arg Leu Thr Leu Asp
                675                 680                 685

<210> SEQ ID NO 35
<211> LENGTH: 2292
<212> TYPE: DNA
<213> ORGANISM: Artificial Sequence
<220> FEATURE:
<223> OTHER INFORMATION: A FRET biosensor of tyrosine kinases

<400> SEQUENCE: 35

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagct tctatgcacc accggcaagc tgcccgtgcc ctggcccacc   180
ctcgtgacca ccctgggcta cggcctgcag tgcttcgccc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca ccgccgacaa gcagaagaac   480
ggcatcaagg ccaacttcaa gatccgccac aacatcgagg acggcggcgt gcagctcgcc   540
gaccactacc agcagaacac ccccatcggc gacggccccg tgctgctgcc cgacaaccac   600
tacctgagct accagtccgc cctgttcaaa gaccccaacg agaagcgcga tcacatggtc   660
ctgctggagt tcgtgaccgc cgccgggatc actgagggca tgaacgagct gtacctcgag   720
aagttttctc aagaacagat cggcgaaaac attgtgtgca gggtcatttg taccacgggt   780
caaattccca tccgagattt gtcagctgat atttcacaag tgcttaagga aaaacgatcc   840
ataaagaaag tttggacatt tggtagaaac ccagcctgtg actatcattt aggaaacatt   900
tcaagactgt caaataagca tttccaaata ctactaggag aagacggtaa ccttttattg   960
aatgacattt ccactaatgg gacctggtta aatgggcaaa aagtcgagaa gaacagcaat  1020
cagttactgt cccaaggtga tgaaataacc gttggtgtag gcgtggaatc agatattta   1080
tctctggtca ttttcataaa cgacaaattt aagcagtgcc tggagcagaa caaagttgat  1140
cgcggtacca gtgctggtgg tagtgctggt ggtagtgctg gtggtagtgc tggtggtagt  1200
gctggtggtt ccggcagtgc tggtggtagt gctggtggta gtaccagtgc tggtggtagt  1260
gctggtggta gtgctggtgg tagtgctggt ggtagtgctg gtggttccgg cagtgctggt  1320
ggtagtgctg gtggtagtac cagtgctggt ggtagtgctg gtggtagtgc tggtggtagt  1380
gctggtggta gtgctggtgg ttccggcagt gctggtggta gtgctggtgg tagtaccagt  1440
gctggtggta gtgctggtgg tagtgctggt ggtagtgctg gtggtagtgc tggtggttcc  1500
ggattgaggc gcgcgacgct ggttgacggc ggccgcatgg tgagcaaggg cgaggagctg  1560
ttcaccgggg tggtgcccat cctggtcgag ctggacggcg acgtaaacgg ccacaggttc  1620
agcgtgtccg gcgagggcga gggcgatgcc acctacggca agctgaccct gaagttcatc  1680
tgcaccaccg gcaagctgcc cgtgccctgg cccaccctcg tgaccaccct gacctggggc  1740
gtgcagtgct tcagccgcta ccccgaccac atgaagcagc acgacttctt caagtccgcc  1800
atgcccgaag gctacgtcca ggagcgtacc atcttcttca aggacgacgg caactacaag  1860
acccgcgccg aggtgaagtt cgagggcgac accctggtga accgcatcga gctgaagggc  1920
atcggcttca aggaggacgg caacatcctg ggcacaagc tagagtacaa ctacatcagc  1980
cacaacgtct atatcaccgc cgacaagcag aagaacggca tcaaggccca cttcaagatc  2040
cgccacaaca tcgaggacgg cggcgtgcag ctcgccgacc actaccagca gaacaccccc  2100
atcggcgacg gccccgtgct gctgcccgac aaccactacc tgagcaccca gtccgccctg  2160
agcaaagacc ccaacgagaa gcgcgatcac atggtcctgc tggagttcgt gaccgccgcc  2220
gggatcactc tcggcatgga cgagctgtct agactgcagc tgcctcctct ggaacgcctg  2280
actctggatt aa                                                      2292
```

<210> SEQ ID NO 36
<211> LENGTH: 763
<212> TYPE: PRT
<213> ORGANISM: Artificial Sequence
<220> FEATURE:
<223> OTHER INFORMATION: A FRET biosensor of tyrosine kinases

<400> SEQUENCE: 36

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Leu
        35                  40                  45

Cys Thr Thr Gly Lys Leu Pro Val Pro Trp Pro Thr Leu Val Thr Thr
50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Phe Lys Asp Pro Asn Glu Lys Arg Asp His Met Val Leu Leu Glu Phe
210                 215                 220

Leu Thr Ala Ala Gly Ile Thr Glu Gly Met Asn Glu Leu Tyr Leu Glu
225                 230                 235                 240

Lys Phe Ser Gln Glu Gln Ile Gly Glu Asn Ile Val Cys Arg Val Ile
                245                 250                 255

Cys Thr Thr Gly Gln Ile Pro Ile Arg Asp Leu Ser Ala Asp Ile Ser
            260                 265                 270

Gln Val Leu Lys Glu Lys Arg Ser Ile Lys Val Trp Thr Phe Gly
        275                 280                 285

Arg Asn Pro Ala Cys Asp Tyr His Leu Gly Asn Ile Ser Arg Leu Ser
290                 295                 300

Asn Lys His Phe Gln Ile Leu Leu Gly Glu Asp Gly Asn Leu Leu Leu
305                 310                 315                 320

Asn Asp Ile Ser Thr Asn Gly Thr Trp Leu Asn Gly Gln Lys Val Glu
                325                 330                 335

Lys Asn Ser Asn Gln Leu Leu Ser Gln Gly Asp Glu Ile Thr Val Gly
            340                 345                 350

Val Gly Val Glu Ser Asp Ile Leu Ser Leu Val Ile Phe Ile Asn Asp
        355                 360                 365
```

```
Lys Phe Lys Gln Cys Leu Glu Gln Asn Lys Val Asp Arg Gly Thr Ser
    370                 375                 380

Ala Gly Gly Ser Ala Gly Gly Ser Ala Gly Gly Ser Ala Gly Gly Ser
385                 390                 395                 400

Ala Gly Gly Ser Gly Ser Ala Gly Gly Ser Ala Gly Gly Ser Thr Ser
                405                 410                 415

Ala Gly Gly Ser Ala Gly Gly Ser Ala Gly Gly Ser Ala Gly Gly Ser
            420                 425                 430

Ala Gly Gly Ser Gly Ser Ala Gly Gly Ser Ala Gly Gly Ser Thr Ser
            435                 440                 445

Ala Gly Gly Ser Ala Gly Gly Ser Ala Gly Gly Ser Ala Gly Gly Ser
450                 455                 460

Ala Gly Gly Ser Gly Ser Ala Gly Gly Ser Ala Gly Gly Ser Thr Ser
465                 470                 475                 480

Ala Gly Gly Ser Ala Gly Gly Ser Ala Gly Gly Ser Ala Gly Gly Ser
                485                 490                 495

Ala Gly Gly Ser Gly Leu Arg Arg Ala Thr Leu Val Asp Gly Gly Arg
            500                 505                 510

Met Val Ser Lys Gly Glu Glu Leu Phe Thr Gly Val Val Pro Ile Leu
            515                 520                 525

Val Glu Leu Asp Gly Asp Val Asn Gly His Arg Phe Ser Val Ser Gly
        530                 535                 540

Glu Gly Glu Gly Asp Ala Thr Tyr Gly Lys Leu Thr Leu Lys Phe Ile
545                 550                 555                 560

Cys Thr Thr Gly Lys Leu Pro Val Pro Trp Pro Thr Leu Val Thr Thr
                565                 570                 575

Leu Thr Trp Gly Val Gln Cys Phe Ser Arg Tyr Pro Asp His Met Lys
            580                 585                 590

Gln His Asp Phe Phe Lys Ser Ala Met Pro Glu Gly Tyr Val Gln Glu
        595                 600                 605

Arg Thr Ile Phe Phe Lys Asp Asp Gly Asn Tyr Lys Thr Arg Ala Glu
    610                 615                 620

Val Lys Phe Glu Gly Asp Thr Leu Val Asn Arg Ile Glu Leu Lys Gly
625                 630                 635                 640

Ile Gly Phe Lys Glu Asp Gly Asn Ile Leu Gly His Lys Leu Glu Tyr
                645                 650                 655

Asn Tyr Ile Ser His Asn Val Tyr Ile Thr Ala Asp Lys Gln Lys Asn
            660                 665                 670

Gly Ile Lys Ala His Phe Lys Ile Arg His Asn Ile Glu Asp Gly Gly
        675                 680                 685

Val Gln Leu Ala Asp His Tyr Gln Gln Asn Thr Pro Ile Gly Asp Gly
    690                 695                 700

Pro Val Leu Leu Pro Asp Asn His Tyr Leu Ser Thr Gln Ser Ala Leu
705                 710                 715                 720

Ser Lys Asp Pro Asn Glu Lys Arg Asp His Met Val Leu Leu Glu Phe
                725                 730                 735

Val Thr Ala Ala Gly Ile Thr Leu Gly Met Asp Glu Leu Ser Arg Leu
            740                 745                 750

Gln Leu Pro Pro Leu Glu Arg Leu Thr Leu Asp
        755                 760

<210> SEQ ID NO 37
<211> LENGTH: 2292
<212> TYPE: DNA
```

<213> ORGANISM: Artificial Sequence
<220> FEATURE:
<223> OTHER INFORMATION: A FRET biosensor of Rac1

<400> SEQUENCE: 37

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct ctatatgcac accggcaagc tgcccgtgcc ctggcccacc     180
ctcgtgacca ccctgggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca ccgccgacaa gcagaagaac     480
ggcatcaagg ccaacttcaa gatccgccac aacatcgagg acggcggcgt gcagctcgcc     540
gaccactacc agcagaacac ccccatcggc gacggccccg tgctgctgcc cgacaaccac     600
tacctgagct accagtccgc cctgttcaaa gaccccaacg agaagcgcga tcacatggtc     660
ctgctggagt tcgtgaccgc cgccgggatc actgagggca tgaacgagct gtacctcgag     720
aagttttctc aagaacagat cggcgaaaac attgtgtgca gggtcatttg taccacgggt     780
caaattccca tccgagattt gtcagctgat atttcacaag tgcttaagga aaacgatcc      840
ataaagaaag tttggacatt tggtagaaac ccagcctgtg actatcattt aggaaacatt     900
tcaagactgt caaataagca tttccaaata ctactaggag aagacggtaa cctttttattg    960
aatgacattt ccactaatgg gacctggtta aatgggcaaa agtcgagaa gaacagcaat     1020
cagttactgt cccaaggtga tgaaataacc gttggtgtag gcgtggaatc agatattta     1080
tctctggtca ttttcataaa cgacaaattt aagcagtgcc tggagcagaa caaagttgat     1140
cgcggtacca gtgctggtgg tagtgctggt ggtagtgctg gtggtagtgc tggtggtagt     1200
gctggtggtt ccggcagtgc tggtggtagt gctggtggta gtaccagtgc tggtggtagt     1260
gctggtggta gtgctggtgg tagtgctggt ggtagtgctg gtggttccgg cagtgctggt     1320
ggtagtgctg gtggtagtac cagtgctggt ggtagtgctg gtggtagtgc tggtggtagt     1380
gctggtggta gtgctggtgg ttccggcagt gctggtggta gtgctggtgg tagtaccagt     1440
gctggtggta gtgctggtgg tagtgctggt ggtagtgctg gtggtagtgc tggtggttcc     1500
ggattgaggc gcgcgacgct ggttgacggg ggccgcatgg tgagcaaggg cgaggagctg     1560
ttcaccgggg tggtgcccat cctggtcgag ctggacggcg acgtaaacgg ccacaggttc     1620
agcgtgtccg gcgagggcga gggcgatgcc acctacggca gctgaccct gaagttcatc     1680
tgcaccaccg gcaagctgcc cgtgccctgg cccaccctcg tgaccaccct gacctggggc     1740
gtgcagtgct tcagccgcta cccccgaccac atgaagcagc acgacttctt caagtccgcc     1800
atgcccgaag gctacgtcca ggagcgtacc atcttcttca aggacgacgg caactacaag     1860
acccgcgccg aggtgaagtt cgagggcgac accctggtga accgcatcga gctgaagggc     1920
atcggcttca ggaggacgg caacatcctg ggcacaagc tagagtacaa ctacatcagc     1980
cacaacgtct atatcaccgc cgacaagcag aagaacggca tcaaggccca cttcaagatc     2040
cgccacaaca tcgaggacgg cggcgtgcag ctcgccgacc actaccagca gaacacccc     2100
atcggcgacg gccccgtgct gctgcccgac aaccactacc tgagcaccca gtccgccctg     2160
agcaaagacc ccaacgagaa gcgcgatcac atggtcctgc tggagttcgt gaccgccgcc     2220
```

```
gggatcactc tcggcatgga cgagctgtct agactgcagc tgcctcctct ggaacgcctg    2280
actctggatt aa                                                         2292
```

<210> SEQ ID NO 38
<211> LENGTH: 763
<212> TYPE: PRT
<213> ORGANISM: Artificial Sequence
<220> FEATURE:
<223> OTHER INFORMATION: A FRET biosensor of Rac1

<400> SEQUENCE: 38

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Leu
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Phe Lys Asp Pro Asn Glu Lys Arg Asp His Met Val Leu Leu Glu Phe
    210                 215                 220

Leu Thr Ala Ala Gly Ile Thr Glu Gly Met Asn Glu Leu Tyr Leu Glu
225                 230                 235                 240

Lys Phe Ser Gln Glu Gln Ile Gly Glu Asn Ile Val Cys Arg Val Ile
                245                 250                 255

Cys Thr Thr Gly Gln Ile Pro Ile Arg Asp Leu Ser Ala Asp Ile Ser
            260                 265                 270

Gln Val Leu Lys Glu Lys Arg Ser Ile Lys Val Trp Thr Phe Gly
        275                 280                 285

Arg Asn Pro Ala Cys Asp Tyr His Leu Gly Asn Ile Ser Arg Leu Ser
    290                 295                 300

Asn Lys His Phe Gln Ile Leu Leu Gly Glu Gly Asn Leu Leu Leu
305                 310                 315                 320

Asn Asp Ile Ser Thr Asn Gly Thr Trp Leu Asn Gly Gln Lys Val Glu
                325                 330                 335

Lys Asn Ser Asn Gln Leu Leu Ser Gln Gly Asp Glu Ile Thr Val Gly
```

-continued

```
               340                 345                 350
Val Gly Val Glu Ser Asp Ile Leu Ser Leu Val Ile Phe Ile Asn Asp
            355                 360                 365
Lys Phe Lys Gln Cys Leu Glu Gln Asn Lys Val Asp Arg Gly Thr Ser
        370                 375                 380
Ala Gly Gly Ser Ala Gly Gly Ser Ala Gly Gly Ser Ala Gly Gly Ser
385                 390                 395                 400
Ala Gly Gly Ser Gly Ser Ala Gly Gly Ser Ala Gly Gly Ser Thr Ser
                405                 410                 415
Ala Gly Gly Ser Ala Gly Gly Ser Ala Gly Gly Ser Ala Gly Gly Ser
            420                 425                 430
Ala Gly Gly Ser Gly Ser Ala Gly Gly Ser Ala Gly Gly Ser Thr Ser
        435                 440                 445
Ala Gly Gly Ser Ala Gly Gly Ser Ala Gly Gly Ser Ala Gly Gly Ser
    450                 455                 460
Ala Gly Gly Ser Gly Ser Ala Gly Gly Ser Ala Gly Gly Ser Thr Ser
465                 470                 475                 480
Ala Gly Gly Ser Ala Gly Gly Ser Ala Gly Gly Ser Ala Gly Gly Ser
                485                 490                 495
Ala Gly Gly Ser Gly Leu Arg Arg Ala Thr Leu Val Asp Gly Gly Arg
            500                 505                 510
Met Val Ser Lys Gly Glu Glu Leu Phe Thr Gly Val Val Pro Ile Leu
        515                 520                 525
Val Glu Leu Asp Gly Asp Val Asn Gly His Arg Phe Ser Val Ser Gly
    530                 535                 540
Glu Gly Glu Gly Asp Ala Thr Tyr Gly Lys Leu Thr Leu Lys Phe Ile
545                 550                 555                 560
Cys Thr Thr Gly Lys Leu Pro Val Pro Trp Pro Thr Leu Val Thr Thr
                565                 570                 575
Leu Thr Trp Gly Val Gln Cys Phe Ser Arg Tyr Pro Asp His Met Lys
            580                 585                 590
Gln His Asp Phe Phe Lys Ser Ala Met Pro Glu Gly Tyr Val Gln Glu
        595                 600                 605
Arg Thr Ile Phe Phe Lys Asp Asp Gly Asn Tyr Lys Thr Arg Ala Glu
    610                 615                 620
Val Lys Phe Glu Gly Asp Thr Leu Val Asn Arg Ile Glu Leu Lys Gly
625                 630                 635                 640
Ile Gly Phe Lys Glu Asp Gly Asn Ile Leu Gly His Lys Leu Glu Tyr
                645                 650                 655
Asn Tyr Ile Ser His Asn Val Tyr Ile Thr Ala Asp Lys Gln Lys Asn
            660                 665                 670
Gly Ile Lys Ala His Phe Lys Ile Arg His Asn Ile Glu Asp Gly Gly
        675                 680                 685
Val Gln Leu Ala Asp His Tyr Gln Gln Asn Thr Pro Ile Gly Asp Gly
    690                 695                 700
Pro Val Leu Leu Pro Asp Asn His Tyr Leu Ser Thr Gln Ser Ala Leu
705                 710                 715                 720
Ser Lys Asp Pro Asn Glu Lys Arg Asp His Met Val Leu Leu Glu Phe
                725                 730                 735
Val Thr Ala Ala Gly Ile Thr Leu Gly Met Asp Glu Leu Ser Arg Leu
            740                 745                 750
Gln Leu Pro Pro Leu Glu Arg Leu Thr Leu Asp
        755                 760
```

<210> SEQ ID NO 39
<211> LENGTH: 2316
<212> TYPE: DNA
<213> ORGANISM: Artificial Sequence
<220> FEATURE:
<223> OTHER INFORMATION: A FRET biosensor of Rac1

<400> SEQUENCE: 39

| | | | | | |
|---|---|---|---|---|---|
| atggtgagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagct | tctatgcacc | accggcaagc | tgcccgtgcc | ctggcccacc | 180 |
| ctcgtgacca | ccctgggcta | cggcctgcag | tgcttcgccc | gctaccccga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggagg | acggcaacat | cctggggcac | 420 |
| aagctggagt | acaactacaa | cagccacaac | gtctatatca | ccgccgacaa | gcagaagaac | 480 |
| ggcatcaagg | ccaacttcaa | gatccgccac | aacatcgagg | acggcggcgt | gcagctcgcc | 540 |
| gaccactacc | agcagaacac | ccccatcggc | gacggccccg | tgctgctgcc | cgacaaccac | 600 |
| tacctgagct | accagtccgc | cctgttcaaa | gaccccaacg | agaagcgcga | tcacatggtc | 660 |
| ctgctggagt | tcctgaccgc | cgccgggatc | actgagggca | tgaacgagct | gtacctcgag | 720 |
| aaagagaaag | agcggccaga | gatttctctc | ccttcagatt | ttgaacacac | aattcatgtc | 780 |
| ggttttgatg | ctgtcacagg | ggagtttacg | ggaatgccag | agcagtgggc | ccgcttgctt | 840 |
| cagacatcaa | atatcactaa | gtcggagcag | aagaaaaacc | cgcaggctgt | tctggatgtg | 900 |
| ttggagtttt | acaactcgaa | gaagacatcc | aacagccaga | aatacatgag | ctttacagat | 960 |
| aagtcagctt | ccgaggtgg | aaccggtggt | ggaggtacca | tgcaggccat | caagtgtgtg | 1020 |
| gtggtgggag | acggagctgt | aggtaaaact | tgcctactga | tcagttacac | aaccaatgca | 1080 |
| tttcctggag | aatatatccc | tactgtcttt | gacaattatt | ctgccaatgt | tatggtagat | 1140 |
| ggaaaaccgg | tgaatctggg | cttatgggat | acagctggaa | agaagatta | tgacagatta | 1200 |
| cgccccctat | cctatccgca | aacagatgtg | ttcttaattt | gcttttcct | tgtgagtcct | 1260 |
| gcatcatttg | aaaatgtccg | tgcaaagtgg | tatcctgagg | tgcggcacca | ctgtcccaac | 1320 |
| actcccatca | tcctagtggg | aactaaaact | gatcttaggg | atgataaaga | cacgatcgag | 1380 |
| aaactgaagg | agaagaagct | gactcccatc | acctatccgc | agggtctagc | catggctaag | 1440 |
| gagattggtg | ctgtaaaata | cctggagtgc | tcggcgctca | cacagcgagg | cctcaagaca | 1500 |
| gtgtttgacg | aagcgatccg | agcagtccgc | ggccgcatgg | tgagcaaggg | cgaggagctg | 1560 |
| ttcaccgggg | tggtgcccat | cctggtcgag | ctggacggcg | acgtaaacgg | ccacaggttc | 1620 |
| agcgtgtccg | gcgagggcga | gggcgatgcc | acctacggca | agctgaccct | gaagttcatc | 1680 |
| tgcaccaccg | gcaagctgcc | cgtgccctgg | cccaccctcg | tgaccaccct | gacctgggc | 1740 |
| gtgcagtgct | tcagccgcta | ccccgaccac | atgaagcagc | acgacttctt | caagtccgcc | 1800 |
| atgcccgaag | gctacgtcca | ggagcgtacc | atcttcttca | aggacgacgg | caactacaag | 1860 |
| acccgcgccg | aggtgaagtt | cgagggcgac | accctggtga | accgcatcga | gctgaagggc | 1920 |
| atcggcttca | aggaggacgg | caacatcctg | gggcacaagc | tagagtacaa | ctacatcagc | 1980 |
| cacaacgtct | atatcaccgc | cgacaagcag | aagaacggca | tcaaggccca | cttcaagatc | 2040 |

-continued

```
cgccacaaca tcgaggacgg cggcgtgcag ctcgccgacc actaccagca gaacaccccc    2100
atcggcgacg gccccgtgct gctgcccgac aaccactacc tgagcaccca gtccgccctg    2160
agcaaagacc ccaacgagaa gcgcgatcac atggtcctgc tggagttcgt gaccgccgcc    2220
gggatcactc tcggcatgga cgagctgtct agaaagatga gcaaagatgg taaaagaag    2280 aaaaagaagt caaagacaaa gtgtgtaatt atgtaa                              2316

<210> SEQ ID NO 40
<211> LENGTH: 771
<212> TYPE: PRT
<213> ORGANISM: Artificial Sequence
<220> FEATURE:
<223> OTHER INFORMATION: A FRET biosensor of Rac1

<400> SEQUENCE: 40

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Leu Leu
            35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Phe Lys Asp Pro Asn Glu Lys Arg Asp His Met Val Leu Leu Glu Phe
    210                 215                 220

Leu Thr Ala Ala Gly Ile Thr Glu Gly Met Asn Glu Leu Tyr Leu Glu
225                 230                 235                 240

Lys Glu Lys Glu Arg Pro Glu Ile Ser Leu Pro Ser Asp Phe Glu His
                245                 250                 255

Thr Ile His Val Gly Phe Asp Ala Val Thr Gly Glu Phe Thr Gly Met
            260                 265                 270

Pro Glu Gln Trp Ala Arg Leu Leu Gln Thr Ser Asn Ile Thr Lys Ser
        275                 280                 285

Glu Gln Lys Lys Asn Pro Gln Ala Val Leu Asp Val Leu Glu Phe Tyr
    290                 295                 300

Asn Ser Lys Lys Thr Ser Asn Ser Gln Lys Tyr Met Ser Phe Thr Asp
305                 310                 315                 320
```

```
Lys Ser Ala Ser Gly Gly Thr Gly Gly Gly Thr Met Gln Ala
            325                 330             335

Ile Lys Cys Val Val Gly Asp Gly Ala Val Gly Lys Thr Cys Leu
            340                 345             350

Leu Ile Ser Tyr Thr Thr Asn Ala Phe Pro Gly Glu Tyr Ile Pro Thr
            355                 360             365

Val Phe Asp Asn Tyr Ser Ala Asn Val Met Val Asp Gly Lys Pro Val
370             375                     380

Asn Leu Gly Leu Trp Asp Thr Ala Gly Gln Glu Asp Tyr Asp Arg Leu
385                 390                 395                 400

Arg Pro Leu Ser Tyr Pro Gln Thr Asp Val Phe Leu Ile Cys Phe Ser
                405                 410                 415

Leu Val Ser Pro Ala Ser Phe Glu Asn Val Arg Ala Lys Trp Tyr Pro
                420                 425             430

Glu Val Arg His His Cys Pro Asn Thr Pro Ile Ile Leu Val Gly Thr
                435                 440                 445

Lys Leu Asp Leu Arg Asp Asp Lys Asp Thr Ile Glu Lys Leu Lys Glu
                450                 455                 460

Lys Lys Leu Thr Pro Ile Thr Tyr Pro Gln Gly Leu Ala Met Ala Lys
465                 470                 475                 480

Glu Ile Gly Ala Val Lys Tyr Leu Glu Cys Ser Ala Leu Thr Gln Arg
                485                 490                 495

Gly Leu Lys Thr Val Phe Asp Glu Ala Ile Arg Ala Val Arg Gly Arg
                500                 505             510

Met Val Ser Lys Gly Glu Glu Leu Phe Thr Gly Val Val Pro Ile Leu
                515                 520                 525

Val Glu Leu Asp Gly Asp Val Asn Gly His Arg Phe Ser Val Ser Gly
                530                 535             540

Glu Gly Glu Gly Asp Ala Thr Tyr Gly Lys Leu Thr Leu Lys Phe Ile
545                 550                 555                 560

Cys Thr Thr Gly Lys Leu Pro Val Pro Trp Pro Thr Leu Val Thr Thr
                565                 570                 575

Leu Thr Trp Gly Val Gln Cys Phe Ser Arg Tyr Pro Asp His Met Lys
                580                 585                 590

Gln His Asp Phe Phe Lys Ser Ala Met Pro Glu Gly Tyr Val Gln Glu
                595                 600                 605

Arg Thr Ile Phe Phe Lys Asp Asp Gly Asn Tyr Lys Thr Arg Ala Glu
                610                 615                 620

Val Lys Phe Glu Gly Asp Thr Leu Val Asn Arg Ile Glu Leu Lys Gly
625                 630                 635                 640

Ile Gly Phe Lys Glu Asp Gly Asn Ile Leu Gly His Lys Leu Glu Tyr
                645                 650                 655

Asn Tyr Ile Ser His Asn Val Tyr Ile Thr Ala Asp Lys Gln Lys Asn
                660                 665                 670

Gly Ile Lys Ala His Phe Lys Ile Arg His Asn Ile Glu Asp Gly Gly
                675                 680                 685

Val Gln Leu Ala Asp His Tyr Gln Gln Asn Thr Pro Ile Gly Asp Gly
                690                 695                 700

Pro Val Leu Leu Pro Asp Asn His Tyr Leu Ser Thr Gln Ser Ala Leu
705                 710                 715                 720

Ser Lys Asp Pro Asn Glu Lys Arg Asp His Met Val Leu Leu Glu Phe
                725                 730                 735
```

Val Thr Ala Ala Gly Ile Thr Leu Gly Met Asp Glu Leu Ser Arg Lys
                740                 745                 750

Met Ser Lys Asp Gly Lys Lys Lys Lys Ser Lys Thr Lys Cys
            755                 760                 765

Val Ile Met
    770

<210> SEQ ID NO 41
<211> LENGTH: 2646
<212> TYPE: DNA
<213> ORGANISM: Artificial Sequence
<220> FEATURE:
<223> OTHER INFORMATION: A FRET biosensor of Cdc42

<400> SEQUENCE: 41

| | | | |
|---|---|---|---|
| atggtgagca | agggcgagga | gctgttcacc | ggggtggtgc ccatcctggt cgagctggac | 60 |
| ggcgacgtaa | acggccacaa | gttcagcgtg | tccggcgagg gcgagggcga tgccacctac | 120 |
| ggcaagctga | ccctgaagct | ctatgcacc | accggcaagc tgcccgtgcc ctggcccacc | 180 |
| ctcgtgacca | ccctgggcta | cggcctgcag | tgcttcgccc gctaccccga ccacatgaag | 240 |
| cagcacgact | tcttcaagtc | cgccatgccc | gaaggctacg tccaggagcg caccatcttc | 300 |
| ttcaaggacg | acggcaacta | caagacccgc | gccgaggtga agttcgaggg cgacaccctg | 360 |
| gtgaaccgca | tcgagctgaa | gggcatcgac | ttcaaggagg acggcaacat cctggggcac | 420 |
| aagctggagt | acaactacaa | cagccacaac | gtctatatca ccgccgacaa gcagaagaac | 480 |
| ggcatcaagg | ccaacttcaa | gatccgccac | aacatcgagg acggcggcgt gcagctcgcc | 540 |
| gaccactacc | agcagaacac | ccccatcggc | gacggccccg tgctgctgcc cgacaaccac | 600 |
| tacctgagct | accagtccgc | cctgttcaaa | gaccccaacg agaagcgcga tcacatggtc | 660 |
| ctgctggagt | tcctgaccgc | cgccgggatc | actgagggca tgaacgagct gtacctcgag | 720 |
| aaagagaaag | agcggccaga | gatttctctc | ccttcagatt ttgaacacac aattcatgtc | 780 |
| ggttttgatg | ctgtcacagg | ggagtttacg | ggaatgccag agcagtgggc ccgcttgctt | 840 |
| cagacatcaa | atatcactaa | gtcggagcag | aagaaaaacc cgcaggctgt tctggatgtg | 900 |
| ttggagtttt | acaactcgaa | gaagacatcc | aacagccaga atacatgag ctttacagat | 960 |
| aagtcagctt | ccggaggaac | cagtgctggt | ggtagtgctg gtggtagtgc tggtggtagt | 1020 |
| gctggtggta | gtgctggtgg | ttccggcagt | gctggtggta gtgctggtgg tagtaccagt | 1080 |
| gctggtggta | gtgctggtgg | tagtgctggt | ggtagtgctg gtggtagtgc tggtggttcc | 1140 |
| ggcagtgctg | gtggtagtgc | tggtggtagt | accagtgctg gtggtagtgc tggtggtagt | 1200 |
| gctggtggta | gtgctggtgg | tagtgctggt | ggttccggca gtgctggtgg tagtgctggt | 1260 |
| ggtagtacca | gtgctggtgg | tagtgctggt | ggtagtgctg gtggtagtgc tggtggtagt | 1320 |
| gctggtggta | cccagacaat | taagtgtgtt | gttgtgggcg atggtgctgt tggtaaaaca | 1380 |
| tgtctcctga | tatcctacac | aacaaacaaa | tttccatcgg aatatgtacc gactgttttt | 1440 |
| gacaactatg | cagtcacagt | tatgattggt | ggagaaccat atactcttgg acttttgat | 1500 |
| actgcagggc | aagaggatta | tgacagatta | cgaccgctga gttatccaca aacagatgta | 1560 |
| tttctagtct | gttttttcagt | ggtctctcca | tcttcatttg aaaacgtgaa agaaaagtgg | 1620 |
| gtgcctgaga | taactcacca | ctgtccaaag | actcctttct tgcttgttgg gactcaaatt | 1680 |
| gatctcagag | atgaccctc | tactattgag | aaacttgcca agaacaaaca gaagcctatc | 1740 |
| actccagaga | ctgctgaaaa | gctggcccgt | gacctgaagg ctgtcaagta tgtggagtgt | 1800 |

```
tctgcactta cacagagagg tctgaagaat gtgtttgatg aggctatcct agctgccggc    1860
ggccgcatgg tgagcaaggg cgaggagctg ttcaccgggg tggtgcccat cctggtcgag    1920
ctggacggcg acgtaaacgg ccacaagttc agcgtgtccg gcgagggcga gggcgatgcc    1980
acctacggca agctgaccct gaagttcatc tgcaccaccg gcaagctgcc cgtgccctgg    2040
cccaccctcg tgaccaccct gtcctggggc gtgcagtgct tcgcccgcta ccccgaccac    2100
atgaagcagc acgacttctt caagtccgcc atgcccgaag ctacgtcca ggagcgcacc     2160 atcttcttca aggacgacgg caactacaag acccgcgccg aggtgaagtt cgagggcgac    2220
accctggtga accgcatcga gctgaagggc atcgacttca aggaggacgg caacatcctg    2280
gggcacaagc tggagtacaa ctacatcagc gggaacgtct atatcaccgc cgacaagcag    2340
aagaacggca tcaaggccaa cttcaagatc cgccacaaca tcgaggacgg cggcgtgcag    2400
ctcgccgacc actaccagca gaacaccccc atcggcgacg gccccgtgct gctgcccgac    2460
aaccactacc tgagcaccca gtccgcctta agcaaagacc ccaacgagaa gcgcgatcac    2520
atggtcctgc tggagttctt gaccgccgcc gggatcactc tcggcatgga cgagctgtct    2580
agaaagatga gcaaagatgg taaaaagaag aaaaagaagt caaagacaaa gtgtgtaatt    2640
atgtaa                                                               2646
```

<210> SEQ ID NO 42
<211> LENGTH: 881
<212> TYPE: PRT
<213> ORGANISM: Artificial Sequence
<220> FEATURE:
<223> OTHER INFORMATION: A FRET biosensor of Cdc42

<400> SEQUENCE: 42

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Leu Leu
            35                  40                  45

Cys Thr Thr Gly Lys Leu Pro Val Pro Trp Pro Thr Leu Val Thr Thr
50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

-continued

```
Phe Lys Asp Pro Asn Glu Lys Arg Asp His Met Val Leu Leu Glu Phe
210                 215                 220
Leu Thr Ala Ala Gly Ile Thr Glu Gly Met Asn Glu Leu Tyr Leu Glu
225                 230                 235                 240
Lys Glu Lys Glu Arg Pro Glu Ile Ser Leu Pro Ser Asp Phe Glu His
                245                 250                 255
Thr Ile His Val Gly Phe Asp Ala Val Thr Gly Glu Phe Thr Gly Met
                260                 265                 270
Pro Glu Gln Trp Ala Arg Leu Leu Gln Thr Ser Asn Ile Thr Lys Ser
            275                 280                 285
Glu Gln Lys Lys Asn Pro Gln Ala Val Leu Asp Val Leu Glu Phe Tyr
290                 295                 300
Asn Ser Lys Lys Thr Ser Asn Ser Gln Lys Tyr Met Ser Phe Thr Asp
305                 310                 315                 320
Lys Ser Ala Ser Gly Gly Thr Ser Ala Gly Gly Ser Ala Gly Gly Ser
                325                 330                 335
Ala Gly Gly Ser Ala Gly Gly Ser Ala Gly Gly Ser Gly Ser Ala Gly
                340                 345                 350
Gly Ser Ala Gly Gly Ser Thr Ser Ala Gly Gly Ser Ala Gly Gly Ser
            355                 360                 365
Ala Gly Gly Ser Ala Gly Gly Ser Ala Gly Gly Ser Gly Ser Ala Gly
            370                 375                 380
Gly Ser Ala Gly Gly Ser Thr Ser Ala Gly Gly Ser Ala Gly Gly Ser
385                 390                 395                 400
Ala Gly Gly Ser Ala Gly Gly Ser Ala Gly Gly Ser Gly Ser Ala Gly
                405                 410                 415
Gly Ser Ala Gly Gly Ser Thr Ser Ala Gly Gly Ser Ala Gly Gly Ser
            420                 425                 430
Ala Gly Gly Ser Ala Gly Gly Ser Ala Gly Gly Thr Gln Thr Ile Lys
            435                 440                 445
Cys Val Val Gly Asp Gly Ala Val Gly Lys Thr Cys Leu Leu Ile
        450                 455                 460
Ser Tyr Thr Thr Asn Lys Phe Pro Ser Glu Tyr Val Pro Thr Val Phe
465                 470                 475                 480
Asp Asn Tyr Ala Val Thr Val Met Ile Gly Gly Glu Pro Tyr Thr Leu
                485                 490                 495
Gly Leu Phe Asp Thr Ala Gly Gln Glu Asp Tyr Asp Arg Leu Arg Pro
            500                 505                 510
Leu Ser Tyr Pro Gln Thr Asp Val Phe Leu Val Cys Phe Ser Val Val
            515                 520                 525
Ser Pro Ser Ser Phe Glu Asn Val Lys Glu Lys Trp Val Pro Glu Ile
530                 535                 540
Thr His His Cys Pro Lys Thr Pro Phe Leu Leu Val Gly Thr Gln Ile
545                 550                 555                 560
Asp Leu Arg Asp Asp Pro Ser Thr Ile Glu Lys Leu Ala Lys Asn Lys
                565                 570                 575
Gln Lys Pro Ile Thr Pro Glu Thr Ala Glu Lys Leu Ala Arg Asp Leu
            580                 585                 590
Lys Ala Val Lys Tyr Val Glu Cys Ser Ala Leu Thr Gln Arg Gly Leu
            595                 600                 605
Lys Asn Val Phe Asp Glu Ala Ile Leu Ala Ala Gly Gly Arg Met Val
            610                 615                 620
Ser Lys Gly Glu Glu Leu Phe Thr Gly Val Val Pro Ile Leu Val Glu
```

Leu Asp Gly Asp Val Asn Gly His Lys Phe Ser Val Ser Gly Glu Gly
625                 630                 635                 640
            645                 650                 655

Glu Gly Asp Ala Thr Tyr Gly Lys Leu Thr Leu Lys Phe Ile Cys Thr
            660                 665                 670

Thr Gly Lys Leu Pro Val Pro Trp Pro Thr Leu Val Thr Thr Leu Ser
            675                 680                 685

Trp Gly Val Gln Cys Phe Ala Arg Tyr Pro Asp His Met Lys Gln His
            690                 695                 700

Asp Phe Phe Lys Ser Ala Met Pro Glu Gly Tyr Val Gln Glu Arg Thr
705                 710                 715                 720

Ile Phe Phe Lys Asp Asp Gly Asn Tyr Lys Thr Arg Ala Glu Val Lys
            725                 730                 735

Phe Glu Gly Asp Thr Leu Val Asn Arg Ile Glu Leu Lys Gly Ile Asp
            740                 745                 750

Phe Lys Glu Asp Gly Asn Ile Leu Gly His Lys Leu Glu Tyr Asn Tyr
            755                 760                 765

Ile Ser Gly Asn Val Tyr Ile Thr Ala Asp Lys Gln Lys Asn Gly Ile
            770                 775                 780

Lys Ala Asn Phe Lys Ile Arg His Asn Ile Glu Asp Gly Gly Val Gln
785                 790                 795                 800

Leu Ala Asp His Tyr Gln Gln Asn Thr Pro Ile Gly Asp Gly Pro Val
            805                 810                 815

Leu Leu Pro Asp Asn His Tyr Leu Ser Thr Gln Ser Ala Leu Ser Lys
            820                 825                 830

Asp Pro Asn Glu Lys Arg Asp His Met Val Leu Leu Glu Phe Leu Thr
            835                 840                 845

Ala Ala Gly Ile Thr Leu Gly Met Asp Glu Leu Ser Arg Lys Met Ser
            850                 855                 860

Lys Asp Gly Lys Lys Lys Lys Lys Ser Lys Thr Lys Cys Val Ile
865                 870                 875                 880

Met

<210> SEQ ID NO 43
<211> LENGTH: 2634
<212> TYPE: DNA
<213> ORGANISM: Artificial Sequence
<220> FEATURE:
<223> OTHER INFORMATION: A FRET biosensor of HRas

<400> SEQUENCE: 43
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct tctatgcacc accggcaagc tgcccgtgcc ctggcccacc     180
ctcgtgacca ccctgggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctgggcac      420 aagctggagt acaactacaa cagccacaac gtctatatca ccgccgacaa gcagaagaac     480
ggcatcaagg ccaacttcaa gatccgccac aacatcgagg acggcggcgt gcagctcgcc     540
gaccactacc agcagaacac ccccatcggc gacggccccg tgctgctgcc cgacaaccac     600

```
tacctgagct accagtccgc cctgttcaaa gaccccaacg agaagcgcga tcacatggtc    660
ctgctggagt tcctgaccgc cgccgggatc actgagggca tgaacgagct gtacctcgag    720
atgacggaat ataagctggt ggtggtgggc gccggcggtg tgggcaagag tgcgctgacc    780
atccagctga tccagaacca ttttgtggac gaatacgacc ccactatcga ggattcctac    840
cggaagcagg tggtcattga tggggagacg tgcctgttgg acatcctgga taccgccggc    900
caggaggagt acagcgccat gcgggaccag tacatgcgca ccggggaggg cttcctgtgt    960
gtgtttgcca tcaacaacac caagtctttt gaggacatcc accagtacag ggagcagatc   1020
aaacgggtga aggactcgga tgacgtgccc atggtgctgg tggggaacaa gtgtgacctg   1080
gctgcacgca ctgtggaatc tcggcaggct caggacctcg cccgaagcta cggcatcccc   1140
tacatcgaga cctcggccaa gacccggcag ggagtggagg atgccttcta cacgttggtg   1200
cgtgagatcc ggcagcacaa gctgcggaag ctgaacggct ccgaggaaac cagtgctggt   1260
ggtagtgctg gtggtagtgc tggtggtagt gctggtggta gtgctggtgg ttccggcagt   1320
gctggtggta gtgctggtgg tagtaccagt gctggtggta gtgctggtgg tagtgctggt   1380
ggtagtgctg gtggtagtgc tggtggttcc ggcagtgctg gtggtagtgc tggtggtagt   1440
accagtgctg gtggtagtgc tggtggtagt gctggtggta gtgctggtgg tagtgctggt   1500
ggttccggca gtgctggtgg tagtgctggt ggtagtacca gtgctggtgg tagtgctggt   1560
ggtagtgctg gtggtagtgc tggtggtagt gctggtggta ccccttctaa gacaagcaac   1620
actatccgtg ttttcttgcc gaacaagcaa agaacagtgg tcaatgtgcg aaatggaatg   1680
agcttgcatg actgccttat gaaagcactc aaggtgaggg gcctgcaacc agagagctgt   1740
gcagtgttca gacttctcca cgaacacaaa ggtaaaaaag cacgcttaga ttggaatact   1800
gaagctgcgc ttttgattgg agaagaactt cacgtagatt tcctgggcgg ccgcatggtg   1860
agcaagggcg aggagctgtt caccggggtg gtgcccatcc tggtcgagct ggacggcgac   1920
gtaaacggcc acaagttcag cgtgtccggc gagggcgagg gcgatgccac ctacggcaag   1980
ctgaccctga agttcatctg caccaccggc aagctgcccg tgccctggcc caccctcgtg   2040
accaccctgt cctggggcgt gcagtgcttc gcccgctacc ccgaccacat gaagcagcac   2100
gacttcttca gtccgccatg cccgaaggc tacgtccagg agcgcaccat cttcttcaag   2160
gacgacggca actacaagac ccgcgccgag gtgaagttcg agggcgacac cctggtgaac   2220
cgcatcgagc tgaagggcat cgacttcaag gaggacggca acatcctggg gcacaagctg   2280
gagtacaact acatcagcgg gaacgtctat atcaccgccg acaagcagaa gaacggcatc   2340
aaggccaact tcaagatccg ccacaacatc gaggacggcg cgtgcagct cgccgaccac   2400
taccagcaga cacccccat cggcgacggc cccgtgctgc tgcccgacaa ccactacctg   2460
agcacccagt ccgccttaag caaagacccc aacgagaagc gcgatcacat ggtcctgctg   2520
gagttcttga ccgccgccgg gatcactctc ggcatggacg agctgtctag aaagatgagc   2580
aaagatggta aaagaagaa aaagaagtca agacaaagt gtgtaattat gtaa            2634
```

<210> SEQ ID NO 44
<211> LENGTH: 877
<212> TYPE: PRT
<213> ORGANISM: Artificial Sequence
<220> FEATURE:
<223> OTHER INFORMATION: A FRET biosensor of HRas

<400> SEQUENCE: 44

Met Val Ser Lys Gly Glu Glu Leu Phe Thr Gly Val Val Pro Ile Leu

-continued

```
1               5                   10                  15
Val Glu Leu Asp Gly Asp Val Asn Gly His Lys Phe Ser Val Ser Gly
                20                  25                  30
Glu Gly Glu Gly Asp Ala Thr Tyr Gly Lys Leu Thr Leu Lys Leu Leu
                35                  40                  45
Cys Thr Thr Gly Lys Leu Pro Val Pro Trp Pro Thr Leu Val Thr Thr
            50                  55                  60
Leu Gly Tyr Gly Leu Gln Cys Phe Ala Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
                100                 105                 110
Val Lys Phe Glu Gly Asp Thr Leu Val Asn Arg Ile Glu Leu Lys Gly
                115                 120                 125
Ile Asp Phe Lys Glu Asp Gly Asn Ile Leu Gly His Lys Leu Glu Tyr
            130                 135                 140
Asn Tyr Asn Ser His Asn Val Tyr Ile Thr Ala Asp Lys Gln Lys Asn
145                 150                 155                 160
Gly Ile Lys Ala Asn Phe Lys Ile Arg His Asn Ile Glu Asp Gly Gly
                165                 170                 175
Val Gln Leu Ala Asp His Tyr Gln Gln Asn Thr Pro Ile Gly Asp Gly
                180                 185                 190
Pro Val Leu Leu Pro Asp Asn His Tyr Leu Ser Tyr Gln Ser Ala Leu
                195                 200                 205
Phe Lys Asp Pro Asn Glu Lys Arg Asp His Met Val Leu Leu Glu Phe
            210                 215                 220
Leu Thr Ala Ala Gly Ile Thr Glu Gly Met Asn Glu Leu Tyr Leu Glu
225                 230                 235                 240
Met Thr Glu Tyr Lys Leu Val Val Val Gly Ala Gly Gly Val Gly Lys
                245                 250                 255
Ser Ala Leu Thr Ile Gln Leu Ile Gln Asn His Phe Val Asp Glu Tyr
                260                 265                 270
Asp Pro Thr Ile Glu Asp Ser Tyr Arg Lys Gln Val Ile Asp Gly
            275                 280                 285
Glu Thr Cys Leu Leu Asp Ile Leu Asp Thr Ala Gly Gln Glu Glu Tyr
            290                 295                 300
Ser Ala Met Arg Asp Gln Tyr Met Arg Thr Gly Glu Gly Phe Leu Cys
305                 310                 315                 320
Val Phe Ala Ile Asn Asn Thr Lys Ser Phe Glu Asp Ile His Gln Tyr
                325                 330                 335
Arg Glu Gln Ile Lys Arg Val Lys Asp Ser Asp Val Pro Met Val
                340                 345                 350
Leu Val Gly Asn Lys Cys Asp Leu Ala Ala Arg Thr Val Glu Ser Arg
                355                 360                 365
Gln Ala Gln Asp Leu Ala Arg Ser Tyr Gly Ile Pro Tyr Ile Glu Thr
            370                 375                 380
Ser Ala Lys Thr Arg Gln Gly Val Glu Asp Ala Phe Tyr Thr Leu Val
385                 390                 395                 400
Arg Glu Ile Arg Gln His Lys Leu Arg Lys Leu Asn Gly Ser Gly Gly
                405                 410                 415
Thr Ser Ala Gly Gly Ser Ala Gly Gly Ser Ala Gly Ser Ala Gly
            420                 425                 430
```

```
Gly Ser Ala Gly Gly Ser Gly Ser Ala Gly Gly Ser
            435                 440             445

Thr Ser Ala Gly Gly Ser Ala Gly Gly Ser Ala Gly
        450             455             460

Gly Ser Ala Gly Gly Ser Gly Ser Ala Gly Gly Ser
465             470             475             480

Thr Ser Ala Gly Gly Ser Ala Gly Gly Ser Ala Gly
            485             490             495

Gly Ser Ala Gly Gly Ser Gly Ser Ala Gly Gly Ser
                500             505         510

Thr Ser Ala Gly Gly Ser Ala Gly Gly Ser Ala Gly
        515             520             525

Gly Ser Ala Gly Gly Thr Pro Ser Lys Thr Ser Asn Thr Ile Arg Val
        530             535                 540

Phe Leu Pro Asn Lys Gln Arg Thr Val Val Asn Val Arg Asn Gly Met
545             550             555             560

Ser Leu His Asp Cys Leu Met Lys Ala Leu Lys Val Arg Gly Leu Gln
            565             570             575

Pro Glu Ser Cys Ala Val Phe Arg Leu Leu His Glu His Lys Gly Lys
        580             585             590

Lys Ala Arg Leu Asp Trp Asn Thr Glu Ala Ala Ser Leu Ile Gly Glu
            595             600             605

Glu Leu His Val Asp Phe Leu Gly Arg Met Val Ser Lys Gly Glu
610             615             620

Glu Leu Phe Thr Gly Val Val Pro Ile Leu Val Glu Leu Asp Gly Asp
625             630             635             640

Val Asn Gly His Lys Phe Ser Val Ser Gly Glu Gly Glu Gly Asp Ala
            645             650             655

Thr Tyr Gly Lys Leu Thr Leu Lys Phe Ile Cys Thr Thr Gly Lys Leu
            660             665             670

Pro Val Pro Trp Pro Thr Leu Val Thr Thr Leu Ser Trp Gly Val Gln
        675             680             685

Cys Phe Ala Arg Tyr Pro Asp His Met Lys Gln His Asp Phe Phe Lys
        690             695             700

Ser Ala Met Pro Glu Gly Tyr Val Gln Glu Arg Thr Ile Phe Phe Lys
705             710             715             720

Asp Asp Gly Asn Tyr Lys Thr Arg Ala Glu Val Lys Phe Glu Gly Asp
            725             730             735

Thr Leu Val Asn Arg Ile Glu Leu Lys Gly Ile Asp Phe Lys Glu Asp
            740             745             750

Gly Asn Ile Leu Gly His Lys Leu Glu Tyr Asn Tyr Ile Ser Gly Asn
            755             760             765

Val Tyr Ile Thr Ala Asp Lys Gln Lys Asn Gly Ile Lys Ala Asn Phe
        770             775             780

Lys Ile Arg His Asn Ile Glu Asp Gly Gly Val Gln Leu Ala Asp His
785             790             795             800

Tyr Gln Gln Asn Thr Pro Ile Gly Asp Gly Pro Val Leu Leu Pro Asp
            805             810             815

Asn His Tyr Leu Ser Thr Gln Ser Ala Leu Ser Lys Asp Pro Asn Glu
            820             825             830

Lys Arg Asp His Met Val Leu Leu Glu Phe Leu Thr Ala Ala Gly Ile
            835             840             845
```

```
Thr Leu Gly Met Asp Glu Leu Ser Arg Lys Met Ser Lys Asp Gly Lys
    850                 855                 860

Lys Lys Lys Lys Lys Ser Lys Thr Lys Cys Val Ile Met
865                 870                 875

<210> SEQ ID NO 45
<211> LENGTH: 134
<212> TYPE: PRT
<213> ORGANISM: Artificial Sequence
<220> FEATURE:
<223> OTHER INFORMATION: synthetic linker

<400> SEQUENCE: 45

Glu Ala Ala Ala Arg Glu Ala Ala Ala Arg Glu Ala Ala Ala Arg Gly
1               5                   10                  15

Gly Glu Ala Ala Ala Arg Glu Ala Ala Ala Arg Glu Ala Ala Ala Arg
            20                  25                  30

Gly Gly Glu Ala Ala Ala Arg Glu Ala Ala Ala Arg Glu Ala Ala Ala
        35                  40                  45

Arg Gly Gly Glu Ala Ala Ala Arg Glu Ala Ala Ala Arg Glu Ala Ala
    50                  55                  60

Ala Arg Gly Gly Glu Ala Ala Ala Arg Glu Ala Ala Ala Arg Glu Ala
65                  70                  75                  80

Ala Ala Arg Gly Gly Glu Ala Ala Ala Arg Glu Ala Ala Ala Arg Glu
                85                  90                  95

Ala Ala Ala Arg Gly Gly Glu Ala Ala Ala Arg Glu Ala Ala Ala Arg
            100                 105                 110

Glu Ala Ala Ala Arg Gly Gly Glu Ala Ala Ala Arg Glu Ala Ala Ala
        115                 120                 125

Arg Glu Ala Ala Ala Arg
    130

<210> SEQ ID NO 46
<211> LENGTH: 124
<212> TYPE: PRT
<213> ORGANISM: Artificial Sequence
<220> FEATURE:
<223> OTHER INFORMATION: synthetic linker

<400> SEQUENCE: 46

Glu Ala Ala Ala Arg Glu Ala Ala Ala Arg Glu Ala Ala Ala Arg Glu
1               5                   10                  15

Ala Ala Ala Arg Glu Ala Ala Ala Arg Glu Ala Ala Ala Arg Gly Gly
            20                  25                  30

Glu Ala Ala Ala Arg Glu Ala Ala Ala Arg Glu Ala Ala Ala Arg Glu
        35                  40                  45

Ala Ala Ala Arg Glu Ala Ala Ala Arg Glu Ala Ala Ala Arg Gly Gly
    50                  55                  60

Glu Ala Ala Ala Arg Glu Ala Ala Ala Arg Glu Ala Ala Ala Arg Glu
65                  70                  75                  80

Ala Ala Ala Arg Glu Ala Ala Ala Arg Glu Ala Ala Ala Arg Gly Gly
                85                  90                  95

Glu Ala Ala Ala Arg Glu Ala Ala Ala Arg Glu Ala Ala Ala Arg Ala
            100                 105                 110

Ala Arg Glu Ala Ala Ala Arg Glu Ala Ala Ala Arg
        115                 120

<210> SEQ ID NO 47
```

<211> LENGTH: 2352
<212> TYPE: DNA
<213> ORGANISM: Artificial Sequence
<220> FEATURE:
<223> OTHER INFORMATION: 3676NES

<400> SEQUENCE: 47

| | | | | | |
|---|---|---|---|---|---|
| atggtgagca | agggcgagga | gctgttcacc | ggggtggtgc | ccatcctggt | cgagctggac | 60 |
| ggcgacgtaa | acggccacaa | gttcagcgtg | tccggcgagg | gcgagggcga | tgccacctac | 120 |
| ggcaagctga | ccctgaagct | tctatgcacc | accggcaagc | tgcccgtgcc | ctggcccacc | 180 |
| ctcgtgacca | ccctgggcta | cggcctgcag | tgcttcgccc | gctaccccga | ccacatgaag | 240 |
| cagcacgact | tcttcaagtc | cgccatgccc | gaaggctacg | tccaggagcg | caccatcttc | 300 |
| ttcaaggacg | acggcaacta | caagacccgc | gccgaggtga | agttcgaggg | cgacaccctg | 360 |
| gtgaaccgca | tcgagctgaa | gggcatcgac | ttcaaggagg | acggcaacat | cctggggcac | 420 |
| aagctggagt | acaactacaa | cagccacaac | gtctatatca | ccgccgacaa | gcagaagaac | 480 |
| ggcatcaagg | ccaacttcaa | gatccgccac | aacatcgagg | acggcggcgt | gcagctcgcc | 540 |
| gaccactacc | agcagaacac | ccccatcggc | gacggccccg | tgctgctgcc | cgacaaccac | 600 |
| tacctgagct | accagtccgc | cctgttcaaa | gaccccaacg | agaagcgcga | tcacatggtc | 660 |
| ctgctggagt | tcctgaccgc | cgccgggatc | actgagggca | tgaacgagct | gtacctcgag | 720 |
| aagttttctc | aagaacagat | cggcgaaaac | attgtgtgca | gggtcatttg | taccacgggt | 780 |
| caaattccca | tccgagattt | gtcagctgat | atttcacaag | tgcttaagga | aaaacgatcc | 840 |
| ataaagaaag | tttggacatt | tggtagaaac | ccagcctgtg | actatcattt | aggaaacatt | 900 |
| tcaagactgt | caaataagca | tttccaaata | ctactaggag | aagacggtaa | cctttttattg | 960 |
| aatgacattt | ccactaatgg | gacctggtta | aatgggcaaa | agtcgagaa | gaacagcaat | 1020 |
| cagttactgt | cccaaggtga | tgaaataacc | gttggtgtag | gcgtggaatc | agatattta | 1080 |
| tctctggtca | ttttcataaa | cgacaaattt | aagcagtgcc | tggagcagaa | caagttgat | 1140 |
| cgcggtaccg | aggcagcagc | aagagaggca | gcagcaaggg | aggcagcagc | aagaggggga | 1200 |
| gaggcagcag | caagggaagc | cgcagcaaga | gaggcagcag | ctaggggcgg | agaggcagca | 1260 |
| gctcgggaag | cagcagctag | agaggcagca | gctaggggag | gagaagcagc | cgctcgcgag | 1320 |
| gcagcagccc | gggaggcagc | agctcggggg | gagaggcag | ccgctagaga | agcagccgct | 1380 |
| agggaggcag | ccgctcgcgg | cggggaagca | gccgcccggg | aggcagccgc | tagggaagca | 1440 |
| gccgctcgcg | gcggcgaggc | cgctgcccgg | gaagccgccg | ccagagaggc | gcagccaga | 1500 |
| ggaggagaag | cagcagcaag | agaggcagcc | gcaagggaag | cagcagcaag | gtccggattg | 1560 |
| aggcgcgcga | cgctggttga | cggcggccgc | atggtgagca | agggcgagga | gctgttcacc | 1620 |
| ggggtggtgc | ccatcctggt | cgagctggac | ggcgacgtaa | acggccacaa | gttcagcgtg | 1680 |
| tccggcgagg | gcgagggcga | tgccacctac | ggcaagctga | ccctgaagtt | catctgcacc | 1740 |
| accggcaagc | tgcccgtgcc | ctggcccacc | ctcgtgacca | ccctgacctg | gggcgtgcag | 1800 |
| tgcttcagcc | gctaccccga | ccacatgaag | cagcacgact | tcttcaagtc | cgccatgccc | 1860 |
| gaaggctacg | tccaggagcg | caccatcttc | ttcaaggacg | acggcaacta | caagacccgc | 1920 |
| gccgaggtga | agttcgaggg | cgacaccctg | gtgaaccgca | tcgagctgaa | gggcatcgac | 1980 |
| ttcaaggagg | acggcaacat | cctggggcac | aagctggagt | acaactacat | cagccacaac | 2040 |
| gtctatatca | ccgccgacaa | gcagaagaac | ggcatcaagg | ccaacttcaa | gatccgccac | 2100 |
| aacatcgagg | acggcagcgt | gcagctcgcc | gaccactacc | agcagaacac | ccccatcggc | 2160 |

```
gacggccccg tgctgctgcc cgacaaccac tacttgagca cccagtccgc cctgagcaaa    2220
gaccccaacg agaagcgcga tcacatggtc ctgctggagt tcgtgaccgc cgccgggatc    2280
actctcggca tggacgagct gggccgctct agactgcagc tgcctcctct ggaacgcctg    2340
actctggatt aa                                                        2352
```

```
<210> SEQ ID NO 48
<211> LENGTH: 783
<212> TYPE: PRT
<213> ORGANISM: Artificial Sequence
<220> FEATURE:
<223> OTHER INFORMATION: 3676NES

<400> SEQUENCE: 48
```

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Leu
        35                  40                  45

Cys Thr Thr Gly Lys Leu Pro Val Pro Trp Pro Thr Leu Val Thr Thr
50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Phe Lys Asp Pro Asn Glu Lys Arg Asp His Met Val Leu Leu Glu Phe
210                 215                 220

Leu Thr Ala Ala Gly Ile Thr Glu Gly Met Asn Glu Leu Tyr Leu Glu
225                 230                 235                 240

Lys Phe Ser Gln Glu Gln Ile Gly Glu Asn Ile Val Cys Arg Val Ile
                245                 250                 255

Cys Thr Thr Gly Gln Ile Pro Ile Arg Asp Leu Ser Ala Asp Ile Ser
            260                 265                 270

Gln Val Leu Lys Glu Lys Arg Ser Ile Lys Lys Val Trp Thr Phe Gly
        275                 280                 285

Arg Asn Pro Ala Cys Asp Tyr His Leu Gly Asn Ile Ser Arg Leu Ser
290                 295                 300

Asn Lys His Phe Gln Ile Leu Leu Gly Glu Asp Gly Asn Leu Leu
305                 310                 315                 320

-continued

```
Asn Asp Ile Ser Thr Asn Gly Thr Trp Leu Asn Gly Gln Lys Val Glu
            325                 330                 335
Lys Asn Ser Asn Gln Leu Leu Ser Gln Gly Asp Glu Ile Thr Val Gly
            340                 345                 350
Val Gly Val Glu Ser Asp Ile Leu Ser Leu Val Ile Phe Ile Asn Asp
            355                 360                 365
Lys Phe Lys Gln Cys Leu Glu Gln Asn Lys Val Asp Arg Gly Thr Glu
370                 375                 380
Ala Ala Ala Arg Glu Ala Ala Arg Glu Ala Ala Arg Gly Gly
385                 390                 395                 400
Glu Ala Ala Ala Arg Glu Ala Ala Arg Glu Ala Ala Arg Gly
                    405                 410                 415
Gly Glu Ala Ala Ala Arg Glu Ala Ala Arg Glu Ala Ala Arg
                420                 425                 430
Gly Gly Glu Ala Ala Ala Arg Glu Ala Ala Arg Glu Ala Ala Ala
            435                 440                 445
Arg Gly Gly Glu Ala Ala Ala Arg Glu Ala Ala Arg Glu Ala Ala
    450                 455                 460
Ala Arg Gly Gly Glu Ala Ala Ala Arg Glu Ala Ala Arg Glu Ala
465                 470                 475                 480
Ala Ala Arg Gly Gly Glu Ala Ala Arg Glu Ala Ala Arg Glu
            485                 490                 495
Ala Ala Ala Arg Gly Gly Glu Ala Ala Arg Glu Ala Ala Arg
                500                 505                 510
Glu Ala Ala Ala Arg Ser Gly Leu Arg Arg Ala Thr Leu Val Asp Gly
            515                 520                 525
Gly Arg Met Val Ser Lys Gly Glu Leu Phe Thr Gly Val Val Pro
    530                 535                 540
Ile Leu Val Glu Leu Asp Gly Asp Val Asn Gly His Lys Phe Ser Val
545                 550                 555                 560
Ser Gly Glu Gly Glu Gly Asp Ala Thr Tyr Gly Lys Leu Thr Leu Lys
            565                 570                 575
Phe Ile Cys Thr Thr Gly Lys Leu Pro Val Pro Trp Pro Thr Leu Val
            580                 585                 590
Thr Thr Leu Thr Trp Gly Val Gln Cys Phe Ser Arg Tyr Pro Asp His
            595                 600                 605
Met Lys Gln His Asp Phe Phe Lys Ser Ala Met Pro Glu Gly Tyr Val
    610                 615                 620
Gln Glu Arg Thr Ile Phe Phe Lys Asp Asp Gly Asn Tyr Lys Thr Arg
625                 630                 635                 640
Ala Glu Val Lys Phe Glu Gly Asp Thr Leu Val Asn Arg Ile Glu Leu
            645                 650                 655
Lys Gly Ile Asp Phe Lys Glu Asp Gly Asn Ile Leu Gly His Lys Leu
            660                 665                 670
Glu Tyr Asn Tyr Ile Ser His Asn Val Tyr Ile Thr Ala Asp Lys Gln
            675                 680                 685
Lys Asn Gly Ile Lys Ala Asn Phe Lys Ile Arg His Asn Ile Glu Asp
    690                 695                 700
Gly Ser Val Gln Leu Ala Asp His Tyr Gln Gln Asn Thr Pro Ile Gly
705                 710                 715                 720
Asp Gly Pro Val Leu Leu Pro Asp Asn His Tyr Leu Ser Thr Gln Ser
            725                 730                 735
Ala Leu Ser Lys Asp Pro Asn Glu Lys Arg Asp His Met Val Leu Leu
```

```
            740                 745                 750
Glu Phe Val Thr Ala Ala Gly Ile Thr Leu Gly Met Asp Glu Leu Gly
        755                 760                 765

Arg Ser Arg Leu Gln Leu Pro Pro Leu Glu Arg Leu Thr Leu Asp
        770                 775                 780

<210> SEQ ID NO 49
<211> LENGTH: 2322
<212> TYPE: DNA
<213> ORGANISM: Artificial Sequence
<220> FEATURE:
<223> OTHER INFORMATION: 3677NES

<400> SEQUENCE: 49
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct ctatgcacc accggcaagc tgcccgtgcc ctggcccacc     180
ctcgtgacca ccctgggcta cggcctgcag tgcttcgccc gctacccga ccacatgaag     240
cagcacgact tcttcaagtc cgccatgccc gaaggctacg tccaggagcg caccatcttc     300
ttcaaggaca cggcaacta aagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca ccgccgacaa gcagaagaac     480
ggcatcaagg ccaacttcaa gatccgccac aacatcgagg acggcggcgt gcagctcgcc     540
gaccactacc agcagaacac ccccatcggc gacggccccg tgctgctgcc cgacaaccac     600
tacctgagct accagtccgc cctgttcaaa gaccccaacg agaagcgcga tcacatggtc     660
ctgctggagt tcctgaccgc cgccgggatc actgagggca tgaacgagct gtacctcgag     720
aagtttttctc aagaacagat cggcgaaaac attgtgtgca gggtcatttg taccacgggt     780
caaattccca tccgagattt gtcagctgat atttcacaag tgcttaagga aaacgatcc     840
ataagaaag tttggacatt tggtagaaac ccagcctgtg actatcattt aggaaacatt     900
tcaagactgt caaataagca tttccaaata ctactaggag aagacggtaa cctttttattg     960
aatgacattt ccactaatgg gacctggtta atgggcaaa aagtcgagaa gaacagcaat    1020
cagttactgt cccaaggtga tgaaataacc gttggtgtag gcgtggaatc agatattttta    1080
tctctggtca ttttcataaa cgacaaatt aagcagtgcc tggagcagaa caaagttgat    1140
cgcggtaccg aagccgcagc aagggaagca gccgctcggg aagccgccgc tcggaggca    1200
gcagcacggg aagcagcagc cagagaagcc gccgcacgag gaggagaggc agctgcacgg    1260
gaagcagctg caagagaggc cgctgcaagg gaagcagctg cacgcgaggc agctgcacga    1320
gaagcagctg cacgggagg cgaagcagct gcaagagaag cagctgcaag ggaggcagct    1380
gcacgcgaag cagctgcacg agaggctgcc gcaagggaag ctgccgctcg cggggcgag    1440
gccgccgcca gagaggccgc cgccagagaa gcagcagcca gagcagcaag agaagccgca    1500
gcacgggaag cagcagcaag gtccggattg aggcgcgcga cgctggttga cggcggccgc    1560
atggtgagca agggcgagga gctgttcacc ggggtggtgc ccatcctggt cgagctggac    1620
ggcgacgtaa acggccacaa gttcagcgtg tccggcgagg gcgagggcga tgccacctac    1680
ggcaagctga ccctgaagtt catctgcacc accggcaagc tgcccgtgcc ctggcccacc    1740
ctcgtgacca ccctgacctg gggcgtgcag tgcttcagcc gctacccga ccacatgaag    1800
cagcacgact tcttcaagtc cgccatgccc gaaggctacg tccaggagcg caccatcttc    1860
```

```
ttcaaggacg acggcaacta caagacccgc gccgaggtga agttcgaggg cgacaccctg    1920
gtgaaccgca tcgagctgaa gggcatcgac ttcaaggagg acggcaacat cctgggccac    1980
aagctggagt acaactacat cagccacaac gtctatatca ccgccgacaa gcagaagaac    2040
ggcatcaagg ccaacttcaa gatccgccac aacatcgagg acggcagcgt gcagctcgcc    2100
gaccactacc agcagaacac ccccatcggc gacggccccg tgctgctgcc cgacaaccac    2160
tacttgagca cccagtccgc cctgagcaaa gaccccaacg agaagcgcga tcacatggtc    2220
ctgctggagt tcgtgaccgc cgccgggatc actctcggca tggacgagct gggccgctct    2280
agactgcagc tgcctcctct ggaacgcctg actctggatt aa                       2322
```

<210> SEQ ID NO 50
<211> LENGTH: 773
<212> TYPE: PRT
<213> ORGANISM: Artificial Sequence
<220> FEATURE:
<223> OTHER INFORMATION: 3677NES

<400> SEQUENCE: 50

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Leu Leu
            35                  40                  45

Cys Thr Thr Gly Lys Leu Pro Val Pro Trp Pro Thr Leu Val Thr Thr
50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Phe Lys Asp Pro Asn Glu Lys Arg Asp His Met Val Leu Leu Glu Phe
    210                 215                 220

Leu Thr Ala Ala Gly Ile Thr Glu Gly Met Asn Glu Leu Tyr Leu Glu
225                 230                 235                 240

Lys Phe Ser Gln Glu Gln Ile Gly Glu Asn Ile Val Cys Arg Val Ile
                245                 250                 255

Cys Thr Thr Gly Gln Ile Pro Ile Arg Asp Leu Ser Ala Asp Ile Ser
            260                 265                 270

Gln Val Leu Lys Glu Lys Arg Ser Ile Lys Lys Val Trp Thr Phe Gly
```

```
            275                 280                 285
Arg Asn Pro Ala Cys Asp Tyr His Leu Gly Asn Ile Ser Arg Leu Ser
    290                 295                 300

Asn Lys His Phe Gln Ile Leu Leu Gly Glu Asp Gly Asn Leu Leu Leu
305                 310                 315                 320

Asn Asp Ile Ser Thr Asn Gly Thr Trp Leu Asn Gly Gln Lys Val Glu
                325                 330                 335

Lys Asn Ser Asn Gln Leu Leu Ser Gln Gly Asp Glu Ile Thr Val Gly
            340                 345                 350

Val Gly Val Glu Ser Asp Ile Leu Ser Leu Val Ile Phe Ile Asn Asp
        355                 360                 365

Lys Phe Lys Gln Cys Leu Glu Gln Asn Lys Val Asp Arg Gly Thr Glu
    370                 375                 380

Ala Ala Ala Arg Glu Ala Ala Arg Glu Ala Ala Arg Glu Ala
385                 390                 395                 400

Ala Ala Arg Glu Ala Ala Arg Glu Ala Ala Arg Gly Gly Glu
                405                 410                 415

Ala Ala Ala Arg Glu Ala Ala Arg Glu Ala Ala Arg Glu Ala
            420                 425                 430

Ala Ala Arg Glu Ala Ala Arg Glu Ala Ala Arg Gly Gly Glu
        435                 440                 445

Ala Ala Ala Arg Glu Ala Ala Arg Glu Ala Ala Arg Glu Ala
    450                 455                 460

Ala Ala Arg Glu Ala Ala Arg Glu Ala Ala Arg Gly Gly Glu
465                 470                 475                 480

Ala Ala Ala Arg Glu Ala Ala Arg Glu Ala Ala Arg Ala Ala
                485                 490                 495

Arg Glu Ala Ala Ala Arg Glu Ala Ala Arg Ser Gly Leu Arg Arg
            500                 505                 510

Ala Thr Leu Val Asp Gly Gly Arg Met Val Ser Lys Gly Glu Glu Leu
        515                 520                 525

Phe Thr Gly Val Val Pro Ile Leu Val Glu Leu Asp Gly Asp Val Asn
    530                 535                 540

Gly His Lys Phe Ser Val Ser Gly Glu Gly Glu Gly Asp Ala Thr Tyr
545                 550                 555                 560

Gly Lys Leu Thr Leu Lys Phe Ile Cys Thr Thr Gly Lys Leu Pro Val
                565                 570                 575

Pro Trp Pro Thr Leu Val Thr Thr Leu Thr Trp Gly Val Gln Cys Phe
            580                 585                 590

Ser Arg Tyr Pro Asp His Met Lys Gln His Asp Phe Phe Lys Ser Ala
        595                 600                 605

Met Pro Glu Gly Tyr Val Gln Glu Arg Thr Ile Phe Phe Lys Asp Asp
    610                 615                 620

Gly Asn Tyr Lys Thr Arg Ala Glu Val Lys Phe Glu Gly Asp Thr Leu
625                 630                 635                 640

Val Asn Arg Ile Glu Leu Lys Gly Ile Asp Phe Lys Glu Asp Gly Asn
                645                 650                 655

Ile Leu Gly His Lys Leu Glu Tyr Asn Tyr Ile Ser His Asn Val Tyr
            660                 665                 670

Ile Thr Ala Asp Lys Gln Lys Asn Gly Ile Lys Ala Asn Phe Lys Ile
        675                 680                 685

Arg His Asn Ile Glu Asp Gly Ser Val Gln Leu Ala Asp His Tyr Gln
    690                 695                 700
```

```
Gln Asn Thr Pro Ile Gly Asp Gly Pro Val Leu Leu Pro Asp Asn His
705                 710                 715                 720

Tyr Leu Ser Thr Gln Ser Ala Leu Ser Lys Asp Pro Asn Glu Lys Arg
                725                 730                 735

Asp His Met Val Leu Leu Glu Phe Val Thr Ala Ala Gly Ile Thr Leu
            740                 745                 750

Gly Met Asp Glu Leu Gly Arg Ser Arg Leu Gln Leu Pro Pro Leu Glu
        755                 760                 765

Arg Leu Thr Leu Asp
    770
```